United States Patent
Deny et al.

(10) Patent No.: US 7,351,570 B2
(45) Date of Patent: Apr. 1, 2008

(54) HDV NUCLEIC ACID MOLECULES AND APPLICATIONS THEREOF

(75) Inventors: Paul Deny, Carrières sur Seine (FR); Nadjia Radjef, Créteil (FR); Patricia Huc-Anais, St-Martin (FR)

(73) Assignee: Assistance Publique-Hopitaux de Paris, Paris (FR)

( * ) Notice: Subject to any disclaimer, the term of this patent is extended or adjusted under 35 U.S.C. 154(b) by 0 days.

(21) Appl. No.: 10/489,864

(22) PCT Filed: Sep. 23, 2002

(86) PCT No.: PCT/FR02/03239

§ 371 (c)(1),
(2), (4) Date: Jan. 6, 2005

(87) PCT Pub. No.: WO03/027291

PCT Pub. Date: Apr. 3, 2003

(65) Prior Publication Data

US 2005/0107587 A1   May 19, 2005

(30) Foreign Application Priority Data

Sep. 24, 2001   (FR) .................................. 01 12285

(51) Int. Cl.
*C12N 7/00*   (2006.01)
*A61K 39/12*   (2006.01)
*A12K 39/29*   (2006.01)

(52) U.S. Cl. .................. 435/235.1; 530/826; 530/820; 530/806; 424/185.1; 424/186.1; 424/189.1

(58) Field of Classification Search ............. 536/23.72; 435/235.1
See application file for complete search history.

(56) References Cited

U.S. PATENT DOCUMENTS 5,932,219 A   8/1999   Houghton et al.

OTHER PUBLICATIONS

Chen et al. "Characterization and phylogenetic analysis of a novel hepatitis D virus strain discovered by restriction fragment length polymorphism analysis". J. Gen Virology, vol. 79(1998), pp. 1105-1113.*

Wu J-C et al "Characterization and phylogenetic analysis of a novel hepatitis D virus strain discovered by restriction fragment length polymorphism analysis" J Gen Virol. vol. 79 (1998) pp. 1105-1113.*

Cotrina M et al "Hepatitis delta genotypes in chronic delta infection in the northeast of Spain (Catalonia)" J Hepatol. vol. 28 (1998), pp. 971-977.*

Fumio Imazeki, et al., "Heterogeneity and evolution rates of delta virus RNA sequences", Journal of Virology, vol. 64, No. 11, pp. 5594-5599 1990.

Database Genban 'en ligne! P. Deny: "Hepatitis delta virus genotypes I and II cocirculate in an endemic area of yakutia, Russia", Database accession No. AJ309874 XP002196404 Abrege, Nov. 14, 2006.

Jaw-Ching Wu, et al. "Characterization and phylogenetic analysis of a novel hepatitis D virus strain discovered by restriction fragment length polymorphism analysis", Journal of General Virology, vol. 79, pp. 1105-1113 1998.

* cited by examiner

*Primary Examiner*—Bruce R. Campell
*Assistant Examiner*—Bo Peng
(74) *Attorney, Agent, or Firm*—Oblon, Spivak, McClelland, Maier & Neustadt, P.C.

(57) ABSTRACT

The invention concerns nucleic acid molecules derived from novel hepatitis D virus strains or isolates constituting genotypes different from known I, II and III genotypes, their fragments, corresponding proteins and their uses as diagnostic reagents. The invention also concerns a method for sensitive diagnosis of the hepatitis D virus (or delta hepatitis virus) and a method for epidemiologic monitoring of HDV-related infections.

5 Claims, 6 Drawing Sheets

Figure 1:
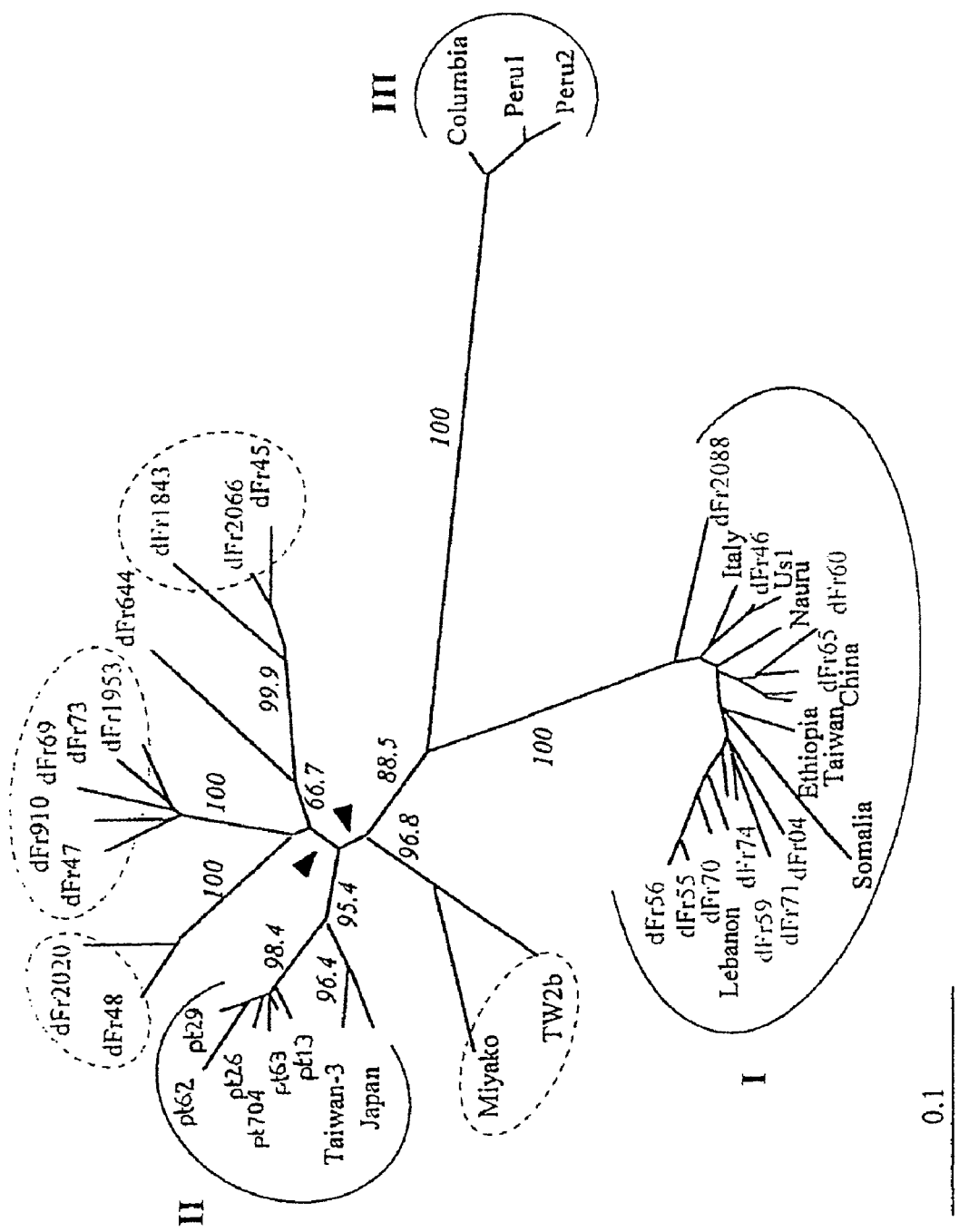

| Patients | | | | HDV Markers | | | | Liver | Treatment |
|---|---|---|---|---|---|---|---|---|---|
| | | | | | Anti-HD | | RNA | | |
| Anonymous/Patient No. | Sex | Age | Origin | HD-Ag | IgM | IgG | PCR1/2* | Anatomy Pathology | Medical-Surgical |
| dFr45 | F | 43 | Cameroon | - | + | + | -/+ | HCA | IFN x 3 9M 12 months |
| dFr47 | F | 38 | Guinea | - | + | + | -/+ | cirrhosis | NT |
| dFr48 | F | 40 | Poland (time spent in Cameroon) | - | + | + | -/+ | cirrhosis | IFN x 3 5M 6 months |
| dFr73 | M | 32 | Ivory Coast | - | + | + | -/+ | HCA | IFN x 3 10M 12 months |
| dFr644 | F | 30 | Congo | - | + | + | -/+ | cirrhosis | Transplantation 09/00 |
| dFr910 | F | 32 | Mali | - | + | + | -/+ | HCA | IFN x 3 3M 3 months |

FIGURE 3

```
                        1                                                  50
 1   TW2b       MSQPDSRRPRRG-REEQLGKWIDARRRKEELERDLRKVNKTIKRLEEDNPWLGNVRGIIRK-DKD
 2   Miyako    ...S.A..V...-...T......G........KE...I..NL.............I......-...
 3   Taiwan-3  ...SE..KS...T...T.ER..TT..KA....K....AR....K...E......IL......-G..
 4   Japan     ...SET..G...T...T.E...T....A....K...TR....K...E......IV......-G..
 5   pt62      ...SE..KS...G..DI.E..VST.KKA........AR.......D......IL......-G..
 6   pt26      ....E..KG...G...I.E...ST..KA........AR......DE......IL......-G..
 7   dFr910    ...SE..KKA...G...I.E..VQ..KDS.D..KK...TKR...K..DE......IL......-G..
 8   dFr47     ...SEQ.K....G..DV.E....Q..KDA.D..KR...AKR.A.K..DE......IL......-G..
 9   dFr73     ...SEQKKS...G...T.E...Q..KDA.D..KR...TKR......DE......L......-G..
10   dFr644    ...S.AK.E...G..DV.S...VE..KDL.D..KRI..TRRN.....DE......IL......-G.A
11   dFr45     ..HA.TK.S.K.-...T.S..DK..EDA.....R...TK....K..D.......IK...G.-VGT
12   dFr48     .GPAEQK.-K..G...I.E..VEL.KNR.D.......TQ.GL.K..D.......II.....-G..
13   Ethiopia  ..RTE.KK-N..G..DA.EQ.VNG...I.....D...AK.K..K..D.......IK..LG.K...
14   Italy     ..RSE.RK-N..G...I.EQ.VAG.KKL.....D...TK.KL.KI.DE......IK..LG.K...
15   Somalia   ..RSEQKK-N..G..DT.E..VNE.KKA...KE...AK.K..K...E......IK..LG.K...
16   Peru      ...TVA.LTSKE-...I.EQ.VEE.KNRRK..KD..RA..K..K..DE.......V.LL.R-K..
                *.  . :    **: * :*    *.  ..**: :*: .:    *::*:.*****: *:: :

100
 1   GEGAPPAKRARTDQMEVDSGPRKRKHPGGFTEQERRDRRRRKALENKKKQLSSGGKNLSREEEEELRRLTEEDERR
 2   ....................................................V..........K........
 3   .........S............TG..P.RS...DK..E............R.........S.......V...E.
 4   .........P............G..P.KS...DK..E..............A...I..K..........D...E.
 5   ......................KP.KS...DK..Q........Q...N...A...S..K..........I..DE.
 6   ......................M..P.KS...DK..E..............R....A...............
 7   ....................TRA.D..D...K.............N...A...S........K........
 8   ....................TRA.D..DK................A...S..K.......K........
 9   ..............R........SRA.D..DK..Q..........NA.:.S..K........G.........
10   ...................G..KSRK....DE................K..E...G......V...K.
11   ........P...R.......G..KSNK....DE...A............A...S..K........K..AD..Q.
12   ......T.K...........GKP.KS...DE..................AA...........G...G..Q.
13   ....................PLR...DK..Q..................A...H.......K.........
14   ....................PLR...DK..Q..................A.......K................
15   .........P......I......KPLR....DK..E.P............A......K........AR...E.
16   ED........P.QET.......GRKPKAR...D.................AG...H..Q........ARD.DE.
      ;****:*:.*  :  **:***.  :   .**:**.  *****:**:;** .*** **.***.** ;*:  :*:.*

196                                         215
 1   ERRVAGPRVGDVNPLDGGPRGAPGGGFVPSMHDIPESPFTRRGDGLDVRGAQEFPZVSPQPPPPRLPLLE-CTPQ
 2   ..................E.A...........T.EGV.....S........I..T.G..ZVD.GR.S...-....
 3   K...........V...SG...........Q.EGV.....A.T.E...I..N.G..WVH.S...QQ.....-....
 4   K...........SR...............Q.AGV.....S.T.E...I..T.G..ZV..S..QQ......-....
 5   Q..............PG.S..........Q.TGV.....S.T.E...I..DRG..WVN.A...GQ......-....
 6   ................PG.S..........Q.TGV.......T.E...I..T.G..WVN.V...GQ......-....
 7   ................PE............Q.L.V.....S.T.S......N.Q..WVD.G.R........-....
 8   ................PGTS..........Q.LGV.....S.T.E......N.QY.WVN.G.R........-....
 9   ................PQ............Q.LNV.....T.E...I..N.Q..WV..GA.S........-....
10   ...A...QD.G...PG.S............R.LGV........I..D.Q..WGQRP.......-....
11   A..I............PE...........QLLGV.....S.T.E...I..DRQ..WGPSPT........-....
12   K..T............PG.D..........T.LHV.....S.T.E......T.Q..WGNTP.R........-....
13   ...A.....P..G....E..Q.........QGV.....H.E......TGG..ZDILF.SD.PFSPQS-.R..
14   ........P..G.I..E...S.........LQGV.....S.T.E...I..NRG..WDILF.AD.PFSPQS-.R..
15   S..I...SA.G....E...S..........QG......H...E....T.TGG..ZDILF.SD.PFSPQS-.R..
16   ...T.....P.G...M..P...........LQGV.....S.T.E.I.I..T.Q..WYGFT....GYYWVPG.TQ.
      ** ***  * * *      *********** :  :***** * *.*:*: *    :*              * *
```

FIGURE 6

SEQUENCE LISTING

<160> NUMBER OF SEQ ID NOS: 83

<210> SEQ ID NO 1
<211> LENGTH: 1672
<212> TYPE: DNA
<213> ORGANISM: hepatitis D virus
<220> FEATURE:
<221> NAME/KEY: source
<222> LOCATION: (1)..(1672)
<223> OTHER INFORMATION: complete genomic sequence of dFR45

<400> SEQUENCE: 1

```
atgagccaag tccgacgaag agtccggaga tgggagagga gagagacccc cgaggaggca      60
aagtcgagag ggcggagaca ctctgaggag aggactccca agaggacaag aaggactcaa     120
gatccgggaa cgaatcccca aaacgccggt aaagctcttg gaatgaggaa aacgggcggg     180
atggtagaaa agagcgagcc tcccgattac gagattcccc tgaacttatt ggatctggag     240
actccgacct taagggtca aaggtaggac agggaggcaa tccaccagga gatttcggac      300
aactcacctc cagaggaccc cttcagcgaa cagaagagcc tgtcccggtc gaattgtccc     360
gtagcgatag gaggagatgc taggagtagg gagagaccgg tgcgagagag gcaagacaag     420
agagcagcgg ggctagcgag tggatgttcc gcccccgtt ggctccgagt gaggcttatc      480
ccggggaatt tggctawctt ccccaactag ccggtcccgg atcccttcc aratgaacgg      540 ggggactccg gcctctcggg gaatcggcgg ctccatggtg aaccccgca gccccccact     600 ccacactcct tccccccgcg gggccccca tccaaagatg gaactccacc cctcagggtt     660
cgcyatccta ccctttctt accttggcc ggcatggtcc cagcctcctc gctggcgccg      720
gctgggcaac attccgaggg gaccgtccct cggcaatggc gaatgggacc caagacctcc     780
aagattccca gagagaatct ggaggtgact gggcactccc tttgccatcc gagtggacgt      840
tcgtcctcct tcggatgccc aggtcggacc acggggaggt ggagatgcca tgccgacccg     900
aagaggaaag aaggattcgg acgcaaacct gtgagtggaa gttcgctctt tattgggggg      960
tacactcgag gagtggaagg cggggagggg gggtcggact aggtccctat ggaaactgtc     1020
ggtctcctcg gatgtcgagt ccctctcccg ttctggagaa gggggactcc gggacaccta     1080
gcagttgagg aacgaagccg ccccccgggcg ctcccctcgg tggtccctcg ggagggttca    1140 catcccaac ccgcgggccg gctattcttc ttgctctttg ctcgtcatcg gcggtcaact      1200
tcctgagttc ctcttcttcc tccttgctga gggactttcc tcctgcggac agctgcttct    1260
tcttgttctc gagggccttc cttcgtcggt gagcccgtct ctcctcgtcg gtgaagcctc    1320
ccttgttact cttttccct ggtccggagt cgacctccat ccgatctgtt cggggtctct    1380
```

-continued

```
tcgccggggg agctccctcc ccagtcccga cctttccaat tattcctttg atgtttccca      1440
gccagggatt gtcgtcctca agtttcttga tggtcttctt tgtcttccgg agcctcctct      1500
cgagttcttc cgcgtcttcc cttgctttgw cccacttcga aagggtctcc tcccttccct      1560
tccgggatct cttcgtatcg gcgtggctca tctcggcaga ggcgggcgat cctcagttct      1620
cttactcttt tcttgaaaga ggagactgct ggacgctccg ccgtgtccga gc              1672
```

```
<210> SEQ ID NO 2
<211> LENGTH: 642
<212> TYPE: DNA
<213> ORGANISM: hepatitis D virus
<220> FEATURE:
<221> NAME/KEY: CDS
<222> LOCATION: (1)..(642)
<223> OTHER INFORMATION: cDNA of LHD

<400> SEQUENCE: 2
```

```
atg agc cac gcc gat acg aag aga tcc cgg aag gga agg gag gag acc        48
Met Ser His Ala Asp Thr Lys Arg Ser Arg Lys Gly Arg Glu Glu Thr
1               5                   10                  15 ctt tcg aag tgg gwc aaa gca agg gaa gac gcg gaa gaa ctc gag agg        96
Leu Ser Lys Trp Xaa Lys Ala Arg Glu Asp Ala Glu Glu Leu Glu Arg
            20                  25                  30 agg ctc cgg aag aca aag aag acc atc aag aaa ctt gag gac gac aat       144
Arg Leu Arg Lys Thr Lys Lys Thr Ile Lys Lys Leu Glu Asp Asp Asn
        35                  40                  45 ccc tgg ctg gga aac atc aaa gga ata att gga aag gtc ggg act ggg       192
Pro Trp Leu Gly Asn Ile Lys Gly Ile Ile Gly Lys Val Gly Thr Gly
50                  55                  60 gag gga gct ccc ccg gcg aag aga ccc cga aca gat cgg atg gag gtc       240
Glu Gly Ala Pro Pro Ala Lys Arg Pro Arg Thr Asp Arg Met Glu Val
65                  70                  75                  80 gac tcc gga cca ggg aaa aag agt aac aag gga ggc ttc acc gac gag       288
Asp Ser Gly Pro Gly Lys Lys Ser Asn Lys Gly Gly Phe Thr Asp Glu
                85                  90                  95 gag aga cgg gct cac cga cga agg aag gcc ctc gag aac aag aag aag       336
Glu Arg Arg Ala His Arg Arg Lys Ala Leu Glu Asn Lys Lys Lys
            100                 105                 110 cag ctg tcc gca gga gga aag tcc ctc agc aag gag gaa gaa gag gaa       384
Gln Leu Ser Ala Gly Gly Lys Ser Leu Ser Lys Glu Glu Glu Glu Glu
        115                 120                 125 ctc agg aag ttg acc gcc gat gac gag caa aga gca aga aga ata gcc       432
Leu Arg Lys Leu Thr Ala Asp Asp Glu Gln Arg Ala Arg Arg Ile Ala
130                 135                 140 ggc ccg cgg gtt ggg gat gtg aac cct ccc gag gga cca ccg agg gga       480
Gly Pro Arg Val Gly Asp Val Asn Pro Pro Glu Gly Pro Pro Arg Gly
145                 150                 155                 160 gcg ccc ggg ggc ggc ttc gtt cct caa ctg cta ggt gtc ccg gag tcc       528
Ala Pro Gly Gly Gly Phe Val Pro Gln Leu Leu Gly Val Pro Glu Ser
                165                 170                 175 ccc ttc tcc aga acg gga gag gga ctc gac atc cga gga gac cga cag       576
Pro Phe Ser Arg Thr Gly Glu Gly Leu Asp Ile Arg Gly Asp Arg Gln
            180                 185                 190 ttt cca tgg gga cct agt ccg acc ccc cct ccc cgc ctt cca ctc ctc       624
Phe Pro Trp Gly Pro Ser Pro Thr Pro Pro Pro Arg Leu Pro Leu Leu
        195                 200                 205 gag tgt acc ccc caa taa                                                642
Glu Cys Thr Pro Gln
210
```

```
<210> SEQ ID NO 3
<211> LENGTH: 213
<212> TYPE: PRT
<213> ORGANISM: hepatitis D virus
<220> FEATURE:
<221> NAME/KEY: misc_feature
<222> LOCATION: (21)..(21)
<223> OTHER INFORMATION: The 'Xaa' at location 21 stands for Asp, or
      Val.

<400> SEQUENCE: 3

Met Ser His Ala Asp Thr Lys Arg Ser Arg Lys Gly Arg Glu Glu Thr
1               5                   10                  15

Leu Ser Lys Trp Xaa Lys Ala Arg Glu Asp Ala Glu Glu Leu Glu Arg
                20                  25                  30

Arg Leu Arg Lys Thr Lys Lys Thr Ile Lys Lys Leu Glu Asp Asp Asn
            35                  40                  45

Pro Trp Leu Gly Asn Ile Lys Gly Ile Ile Gly Lys Val Gly Thr Gly
    50                  55                  60

Glu Gly Ala Pro Pro Ala Lys Arg Pro Arg Thr Asp Arg Met Glu Val
65                  70                  75                  80

Asp Ser Gly Pro Gly Lys Lys Ser Asn Lys Gly Phe Thr Asp Glu
                85                  90                  95

Glu Arg Arg Ala His Arg Arg Lys Ala Leu Glu Asn Lys Lys Lys
            100                 105                 110

Gln Leu Ser Ala Gly Gly Lys Ser Leu Ser Lys Glu Glu Glu Glu
        115                 120                 125

Leu Arg Lys Leu Thr Ala Asp Asp Glu Gln Arg Ala Arg Arg Ile Ala
130                 135                 140

Gly Pro Arg Val Gly Asp Val Asn Pro Glu Gly Pro Pro Arg Gly
145                 150                 155                 160

Ala Pro Gly Gly Gly Phe Val Pro Gln Leu Leu Gly Val Pro Glu Ser
                165                 170                 175

Pro Phe Ser Arg Thr Gly Glu Gly Leu Asp Ile Arg Gly Asp Arg Gln
            180                 185                 190

Phe Pro Trp Gly Pro Ser Pro Thr Pro Pro Arg Leu Pro Leu Leu
        195                 200                 205

Glu Cys Thr Pro Gln
    210

<210> SEQ ID NO 4
<211> LENGTH: 585
<212> TYPE: DNA
<213> ORGANISM: hepatitis D virus
<220> FEATURE:
<221> NAME/KEY: CDS
<222> LOCATION: (1)..(585)
<223> OTHER INFORMATION: cDNA of sHD

<400> SEQUENCE: 4 atg agc cac gcc gat acg aag aga tcc cgg aag gga agg gag gag acc    48
Met Ser His Ala Asp Thr Lys Arg Ser Arg Lys Gly Arg Glu Glu Thr
1               5                   10                  15 ctt tcg aag tgg gwc aaa gca agg gaa gac gcg gaa gaa ctc gag agg    96
Leu Ser Lys Trp Xaa Lys Ala Arg Glu Asp Ala Glu Glu Leu Glu Arg
                20                  25                  30 agg ctc cgg aag aca aag aag acc atc aag aaa ctt gag gac gac aat   144
Arg Leu Arg Lys Thr Lys Lys Thr Ile Lys Lys Leu Glu Asp Asp Asn
            35                  40                  45 ccc tgg ctg gga aac atc aaa gga ata att gga aag gtc ggg act ggg   192
```

```
Pro Trp Leu Gly Asn Ile Lys Gly Ile Ile Gly Lys Val Gly Thr Gly
        50                  55                  60 gag gga gct ccc ccg gcg aag aga ccc cga aca gat cgg atg gag gtc      240
Glu Gly Ala Pro Pro Ala Lys Arg Pro Arg Thr Asp Arg Met Glu Val
65                  70                  75                  80 gac tcc gga cca ggg aaa aag agt aac aag gga ggc ttc acc gac gag      288
Asp Ser Gly Pro Gly Lys Lys Ser Asn Lys Gly Gly Phe Thr Asp Glu
                    85                  90                  95 gag aga cgg gct cac cga cga agg aag gcc ctc gag aac aag aag aag      336
Glu Arg Arg Ala His Arg Arg Arg Lys Ala Leu Glu Asn Lys Lys Lys
                    100                 105                 110 cag ctg tcc gca gga gga aag tcc ctc agc aag gag gaa gaa gag gaa      384
Gln Leu Ser Ala Gly Gly Lys Ser Leu Ser Lys Glu Glu Glu Glu Glu
                    115                 120                 125 ctc agg aag ttg acc gcc gat gac gag caa aga gca aga aga ata gcc      432
Leu Arg Lys Leu Thr Ala Asp Asp Glu Gln Arg Ala Arg Arg Ile Ala
130                 135                 140 ggc ccg cgg gtt ggg gat gtg aac cct ccc gag gga cca ccg agg gga      480
Gly Pro Arg Val Gly Asp Val Asn Pro Pro Glu Gly Pro Pro Arg Gly
145                 150                 155                 160 gcg ccc ggg ggc ggc ttc gtt cct caa ctg cta ggt gtc ccg gag tcc      528
Ala Pro Gly Gly Gly Phe Val Pro Gln Leu Leu Gly Val Pro Glu Ser
                    165                 170                 175 ccc ttc tcc aga acg gga gag gga ctc gac atc cga gga gac cga cag      576
Pro Phe Ser Arg Thr Gly Glu Gly Leu Asp Ile Arg Gly Asp Arg Gln
                    180                 185                 190 ttt cca tag                                                          585
Phe Pro <210> SEQ ID NO 5
<211> LENGTH: 194
<212> TYPE: PRT
<213> ORGANISM: hepatitis D virus
<220> FEATURE:
<221> NAME/KEY: misc_feature
<222> LOCATION: (21)..(21)
<223> OTHER INFORMATION: The 'Xaa' at location 21 stands for Asp, or
      Val.

<400> SEQUENCE: 5

Met Ser His Ala Asp Thr Lys Arg Ser Arg Lys Gly Arg Glu Glu Thr
1               5                   10                  15

Leu Ser Lys Trp Xaa Lys Ala Arg Glu Asp Ala Glu Glu Leu Glu Arg
                20                  25                  30

Arg Leu Arg Lys Thr Lys Lys Thr Ile Lys Lys Leu Glu Asp Asp Asn
            35                  40                  45

Pro Trp Leu Gly Asn Ile Lys Gly Ile Ile Gly Lys Val Gly Thr Gly
        50                  55                  60

Glu Gly Ala Pro Pro Ala Lys Arg Pro Arg Thr Asp Arg Met Glu Val
65                  70                  75                  80

Asp Ser Gly Pro Gly Lys Lys Ser Asn Lys Gly Gly Phe Thr Asp Glu
                85                  90                  95

Glu Arg Arg Ala His Arg Arg Arg Lys Ala Leu Glu Asn Lys Lys Lys
                100                 105                 110

Gln Leu Ser Ala Gly Gly Lys Ser Leu Ser Lys Glu Glu Glu Glu Glu
                115                 120                 125

Leu Arg Lys Leu Thr Ala Asp Asp Glu Gln Arg Ala Arg Arg Ile Ala
130                 135                 140

Gly Pro Arg Val Gly Asp Val Asn Pro Pro Glu Gly Pro Pro Arg Gly
```

-continued

```
          145                 150                 155                 160
Ala Pro Gly Gly Gly Phe Val Pro Gln Leu Leu Gly Val Pro Glu Ser
                165                 170                 175
Pro Phe Ser Arg Thr Gly Glu Gly Leu Asp Ile Arg Gly Asp Arg Gln
            180                 185                 190
Phe Pro

<210> SEQ ID NO 6
<211> LENGTH: 1697
<212> TYPE: DNA
<213> ORGANISM: hepatitis D virus
<220> FEATURE:
<221> NAME/KEY: source
<222> LOCATION: (1)..(1697)
<223> OTHER INFORMATION: complete genomic sequence of dFR47
<220> FEATURE:
<221> NAME/KEY: misc_feature
<222> LOCATION: (278)..(278)
<223> OTHER INFORMATION: n is a, g, t, or c
<220> FEATURE:
<221> NAME/KEY: misc_feature
<222> LOCATION: (558)..(558)
<223> OTHER INFORMATION: n is a, g, t, or c
<220> FEATURE:
<221> NAME/KEY: misc_feature
<222> LOCATION: (595)..(595)
<223> OTHER INFORMATION: n is a, g, t, or c

<400> SEQUENCE: 6
atgggccacg yagccgacaa ggagccggag gaggagggggt tggaggtccc gaggaggact       60
cyaagcaaag aagggggagga atctcgaaaa agaactccca agaagaaccg agaacaaccy      120
caagaagagg aggtttccca aacgcyggtg gagcacccgg aacaaggaa acaggagaag       180 gatcggtaga aaagagcgag cctcccgatc cgaggggccc tggacacctc agctctggag      240
tcctccgacc cgtgaggttg aggttctccg cgcagggnag gcagccaccg ggagaaaacg      300
gagaaaccac ctccagagga cccctttcagc gaacagagaa gcgcactggg acgtcaggat      360
gagtccatag cgataggagg ggatgctagg agtcggcagc gaccgaagcg aggaaagaaa      420
gtaaagarag caacggggct agcgagtgga tgttccgcct ccccggagtc ccgagtgagg      480
cttatcccgg ggaaccccggc caagccccca aaatgtctgg ttcccacggg ctccacttcc      540
aaaaggagga gcgggggnac ttggaacgtg aggggaccag ttcagtccgt ggganttrcc      600
ccggacctcc ggttctccac actccttccc ccctgcgggc ttcccagtaa acggtaagaa      660 cccacccctcg gggtccgacg tcccacccctt tcttaccttg tggccggcat ggtcccagcc      720
tcctcgctgg cgccggctgg gcaacattcc grggggaccg tccctcggta atggcgaatg      780
ggrcccagaa ctctctctag gttcccagag agaaccgaga gaaaactggc tctccccttag      840 ccatccgagt ggacgttctg tcctccttcg gatgcccagg tcggaccgcg ggaggtgga      900 gatgccatgc cgaccgaag aggaaagaag gactcggacg cgaactcgtg agtggaaact      960 tattcctta ctggggagta cactcgagga gtggaaggcg gggaggccgg ggtcccgggy     1020
ytacccacgg gtactgctgg ttccccctca cgtccagtcc ctccccgtc ctggagaagg     1080 gagactcrgg aacacctagc atttgaggga caaagccgcc cccgggcgct ccctcggag     1140 atgttccggg tgggttcaca tccccaaccc gcgggccggc tactcttctt tctcttctct     1200
cgtcttcctc ggtcaacttc cggagttcct cttcctcctc cttgctragt gactttcctc     1260
ccgcgctcag ttgtttcttc ttgttctcga gggccttcct tcttcggtgg tcccgtctct     1320
ccttgtcggt gaagtctccc gcgcgagtcc tcttcctagg tccggagtcg acctccatcy     1380
```

-continued

```
gatccgtccg ggccctcttc gccgggggag ctccctcccc gtccttccct tttcttatta    1440
ttccgaggat gttccccagc cagggattct catcctcgag tytcttggcg gttctcttgg    1500
ccttccggag cctttctcg aggtcctccg cgtcttttct tgcttggatc catttctcga     1560
ggacatcctc ccttcctccc ctccggggtt tcctctgttc ggactggctc atcctcggag    1620
agggggcgac ggcgtctgtt ctctattctt ttttctctaa aagaggagac agcttgccgc    1680
ccgcccccag ccccggg                                                  1697

<210> SEQ ID NO 7
<211> LENGTH: 645
<212> TYPE: DNA
<213> ORGANISM: hepatitis D virus
<220> FEATURE:
<221> NAME/KEY: CDS
<222> LOCATION: (1)..(645)
<223> OTHER INFORMATION: cDNA of LHD

<400> SEQUENCE: 7 atg agc cag tcc gaa cag agg aaa ccc cgg agg gga gga agg gag gat        48
Met Ser Gln Ser Glu Gln Arg Lys Pro Arg Arg Gly Gly Arg Glu Asp
1               5                   10                  15 gtc ctc gag aaa tgg atc caa gca aga aaa gac gcg gag gac ctc gag        96
Val Leu Glu Lys Trp Ile Gln Ala Arg Lys Asp Ala Glu Asp Leu Glu
            20                  25                  30 aaa agg ctc cgg aag gcc aag aga acc gcc aag ara ctc gag gat gag       144
Lys Arg Leu Arg Lys Ala Lys Arg Thr Ala Lys Xaa Leu Glu Asp Glu
        35                  40                  45 aat ccc tgg ctg ggg aac atc ctc gga ata ata aga aaa ggg aag gac       192
Asn Pro Trp Leu Gly Asn Ile Leu Gly Ile Ile Arg Lys Gly Lys Asp
    50                  55                  60 ggg gag gga gct ccc ccg gcg aag agg gcc cgg acg gat crg atg gag       240
Gly Glu Gly Ala Pro Pro Ala Lys Arg Ala Arg Thr Asp Xaa Met Glu
65                  70                  75                  80 gtc gac tcc gga cct agg aag agg act cgc gcg gga gac ttc acc gac       288
Val Asp Ser Gly Pro Arg Lys Arg Thr Arg Ala Gly Asp Phe Thr Asp
                85                  90                  95 aag gag aga cgg gac cac cga aga agg aag gcc ctc gag aac aag aag       336
Lys Glu Arg Arg Asp His Arg Arg Lys Ala Leu Glu Asn Lys Lys
            100                 105                 110 aaa caa ctg agc gcg gga gga aag tca cty agc aag gag gag gaa gag       384
Lys Gln Leu Ser Ala Gly Gly Lys Ser Xaa Ser Lys Glu Glu Glu Glu
        115                 120                 125 gaa ctc cgg aag ttg acc gag gaa gac gag aga aga gaa aga aga gta       432
Glu Leu Arg Lys Leu Thr Glu Glu Asp Glu Arg Arg Glu Arg Arg Val
    130                 135                 140 gcc ggc ccg cgg gtt ggg gat gtg aac cca ccc gga aca tct ccg agg       480
Ala Gly Pro Arg Val Gly Asp Val Asn Pro Pro Gly Thr Ser Pro Arg
145                 150                 155                 160 gga gcg ccc ggg ggc ggc ttt gtc cct caa atg cta ggt gtt ccy gag       528
Gly Ala Pro Gly Gly Gly Phe Val Pro Gln Met Leu Gly Val Xaa Glu
                165                 170                 175 tct ccc ttc tcc agg acg ggg gag gga ctg gac gtg agg ggg aac cag       576
Ser Pro Phe Ser Arg Thr Gly Glu Gly Leu Asp Val Arg Gly Asn Gln
            180                 185                 190 cag tac ccg tgg gtg grc ccg gga ccc cgg cct ccc cgc ctt cca ctc       624
Gln Tyr Pro Trp Val Xaa Pro Gly Pro Arg Pro Pro Arg Leu Pro Leu
        195                 200                 205 ctc gag tgt act ccc cag taa                                           645
Leu Glu Cys Thr Pro Gln
```

-continued

```
                            210

<210> SEQ ID NO 8
<211> LENGTH: 214
<212> TYPE: PRT
<213> ORGANISM: hepatitis D virus
<220> FEATURE:
<221> NAME/KEY: misc_feature
<222> LOCATION: (44)..(44)
<223> OTHER INFORMATION: The 'Xaa' at location 44 stands for Arg, or
      Lys.
<220> FEATURE:
<221> NAME/KEY: misc_feature
<222> LOCATION: (78)..(78)
<223> OTHER INFORMATION: The 'Xaa' at location 78 stands for Arg, or
      Gln.
<220> FEATURE:
<221> NAME/KEY: misc_feature
<222> LOCATION: (122)..(122)
<223> OTHER INFORMATION: The 'Xaa' at location 122 stands for Leu.
<220> FEATURE:
<221> NAME/KEY: misc_feature
<222> LOCATION: (175)..(175)
<223> OTHER INFORMATION: The 'Xaa' at location 175 stands for Pro.
<220> FEATURE:
<221> NAME/KEY: misc_feature
<222> LOCATION: (198)..(198)
<223> OTHER INFORMATION: The 'Xaa' at location 198 stands for Gly, or
      Asp.

<400> SEQUENCE: 8

Met Ser Gln Ser Glu Gln Arg Lys Pro Arg Gly Gly Arg Glu Asp
1               5                   10                  15

Val Leu Glu Lys Trp Ile Gln Ala Arg Lys Asp Ala Glu Asp Leu Glu
            20                  25                  30

Lys Arg Leu Arg Lys Ala Lys Arg Thr Ala Lys Xaa Leu Glu Asp Glu
        35                  40                  45

Asn Pro Trp Leu Gly Asn Ile Leu Gly Ile Ile Arg Lys Gly Lys Asp
    50                  55                  60

Gly Glu Gly Ala Pro Pro Ala Lys Arg Ala Arg Thr Asp Xaa Met Glu
65                  70                  75                  80

Val Asp Ser Gly Pro Arg Lys Arg Thr Arg Ala Gly Asp Phe Thr Asp
                85                  90                  95

Lys Glu Arg Arg Asp His Arg Arg Arg Lys Ala Leu Glu Asn Lys Lys
            100                 105                 110

Lys Gln Leu Ser Ala Gly Gly Lys Ser Xaa Ser Lys Glu Glu Glu Glu
        115                 120                 125

Glu Leu Arg Lys Leu Thr Glu Glu Asp Glu Arg Arg Glu Arg Arg Val
    130                 135                 140

Ala Gly Pro Arg Val Gly Asp Val Asn Pro Gly Thr Ser Pro Arg
145                 150                 155                 160

Gly Ala Pro Gly Gly Gly Phe Val Pro Gln Met Leu Gly Val Xaa Glu
                165                 170                 175

Ser Pro Phe Ser Arg Thr Gly Glu Gly Leu Asp Val Arg Gly Asn Gln
            180                 185                 190

Gln Tyr Pro Trp Val Xaa Pro Gly Pro Arg Pro Arg Leu Pro Leu
        195                 200                 205

Leu Glu Cys Thr Pro Gln
    210

<210> SEQ ID NO 9
<211> LENGTH: 588
<212> TYPE: DNA
```

<213> ORGANISM: hepatitis D virus
<220> FEATURE:
<221> NAME/KEY: CDS
<222> LOCATION: (1)..(588)
<223> OTHER INFORMATION: cDNA of sHD

<400> SEQUENCE: 9

```
atg agc cag tcc gaa cag agg aaa ccc cgg agg gga gga agg gag gat      48
Met Ser Gln Ser Glu Gln Arg Lys Pro Arg Arg Gly Gly Arg Glu Asp
1               5                   10                  15 gtc ctc gag aaa tgg atc caa gca aga aaa gac gcg gag gac ctc gag      96
Val Leu Glu Lys Trp Ile Gln Ala Arg Lys Asp Ala Glu Asp Leu Glu
                20                  25                  30 aaa agg ctc cgg aag gcc aag aga acc gcc aag ara ctc gag gat gag     144
Lys Arg Leu Arg Lys Ala Lys Arg Thr Ala Lys Xaa Leu Glu Asp Glu
            35                  40                  45 aat ccc tgg ctg ggg aac atc ctc gga ata ata aga aaa ggg aag gac     192
Asn Pro Trp Leu Gly Asn Ile Leu Gly Ile Ile Arg Lys Gly Lys Asp
        50                  55                  60 ggg gag gga gct ccc ccg gcg aag agg gcc cgg acg gat crg atg gag     240
Gly Glu Gly Ala Pro Pro Ala Lys Arg Ala Arg Thr Asp Xaa Met Glu
65                  70                  75                  80 gtc gac tcc gga cct agg aag agg act cgc gcg gga gac ttc acc gac     288
Val Asp Ser Gly Pro Arg Lys Arg Thr Arg Ala Gly Asp Phe Thr Asp
                85                  90                  95 aag gag aga cgg gac cac cga aga agg aag gcc ctc gag aac aag aag     336
Lys Glu Arg Arg Asp His Arg Arg Lys Ala Leu Glu Asn Lys Lys
            100                 105                 110 aaa caa ctg agc gcg gga gga aag tca cty agc aag gag gag gaa gag     384
Lys Gln Leu Ser Ala Gly Gly Lys Ser Xaa Ser Lys Glu Glu Glu Glu
        115                 120                 125 gaa ctc cgg aag ttg acc gag gaa gac gag aga aga gaa aga aga gta     432
Glu Leu Arg Lys Leu Thr Glu Glu Asp Glu Arg Arg Glu Arg Arg Val
130                 135                 140 gcc ggc ccg cgg gtt ggg gat gtg aac cca ccc gga aca tct ccg agg     480
Ala Gly Pro Arg Val Gly Asp Val Asn Pro Pro Gly Thr Ser Pro Arg
145                 150                 155                 160 gga gcg ccc ggg ggc ggc ttt gtc cct caa atg cta ggt gtt ccy gag     528
Gly Ala Pro Gly Gly Gly Phe Val Pro Gln Met Leu Gly Val Xaa Glu
                165                 170                 175 tct ccc ttc tcc agg acg ggg gag gga ctg gac gtg agg ggg aac cag     576
Ser Pro Phe Ser Arg Thr Gly Glu Gly Leu Asp Val Arg Gly Asn Gln
            180                 185                 190 cag tac ccg tga                                                     588
Gln Tyr Pro
        195
```

<210> SEQ ID NO 10
<211> LENGTH: 195
<212> TYPE: PRT
<213> ORGANISM: hepatitis D virus
<220> FEATURE:
<221> NAME/KEY: misc_feature
<222> LOCATION: (44)..(44)
<223> OTHER INFORMATION: The 'Xaa' at location 44 stands for Arg, or
      Lys.
<220> FEATURE:
<221> NAME/KEY: misc_feature
<222> LOCATION: (78)..(78)
<223> OTHER INFORMATION: The 'Xaa' at location 78 stands for Arg, or
      Gln.
<220> FEATURE:
<221> NAME/KEY: misc_feature
<222> LOCATION: (122)..(122)
<223> OTHER INFORMATION: The 'Xaa' at location 122 stands for Leu.

<220> FEATURE:
<221> NAME/KEY: misc_feature
<222> LOCATION: (175)..(175)
<223> OTHER INFORMATION: The 'Xaa' at location 175 stands for Pro.

<400> SEQUENCE: 10

Met Ser Gln Ser Glu Gln Arg Lys Pro Arg Gly Gly Arg Glu Asp
1               5                   10                  15

Val Leu Glu Lys Trp Ile Gln Ala Arg Lys Asp Ala Glu Asp Leu Glu
            20                  25                  30

Lys Arg Leu Arg Lys Ala Lys Arg Thr Ala Lys Xaa Leu Glu Asp Glu
        35                  40                  45

Asn Pro Trp Leu Gly Asn Ile Leu Gly Ile Ile Arg Lys Gly Lys Asp
    50                  55                  60

Gly Glu Gly Ala Pro Pro Ala Lys Arg Ala Arg Thr Asp Xaa Met Glu
65                  70                  75                  80

Val Asp Ser Gly Pro Arg Lys Arg Thr Arg Ala Gly Asp Phe Thr Asp
                85                  90                  95

Lys Glu Arg Arg Asp His Arg Arg Lys Ala Leu Glu Asn Lys Lys
            100                 105                 110

Lys Gln Leu Ser Ala Gly Gly Lys Ser Xaa Ser Lys Glu Glu Glu Glu
        115                 120                 125

Glu Leu Arg Lys Leu Thr Glu Glu Asp Glu Arg Glu Arg Arg Val
    130                 135                 140

Ala Gly Pro Arg Val Gly Asp Val Asn Pro Pro Gly Thr Ser Pro Arg
145                 150                 155                 160

Gly Ala Pro Gly Gly Gly Phe Val Pro Gln Met Leu Gly Val Xaa Glu
                165                 170                 175

Ser Pro Phe Ser Arg Thr Gly Glu Gly Leu Asp Val Arg Gly Asn Gln
            180                 185                 190

Gln Tyr Pro
        195

<210> SEQ ID NO 11
<211> LENGTH: 1697
<212> TYPE: DNA
<213> ORGANISM: hepatitis D virus
<220> FEATURE:
<221> NAME/KEY: source
<222> LOCATION: (1)..(1697)
<223> OTHER INFORMATION: complete genomic sequence of dFr73
<220> FEATURE:
<221> NAME/KEY: misc_feature
<222> LOCATION: (363)..(363)
<223> OTHER INFORMATION: n is a, g, t, or c
<220> FEATURE:
<221> NAME/KEY: misc_feature
<222> LOCATION: (364)..(364)
<223> OTHER INFORMATION: n is a, g, t, or c
<220> FEATURE:
<221> NAME/KEY: misc_feature
<222> LOCATION: (649)..(649)
<223> OTHER INFORMATION: n is a, g, t, or c

<400> SEQUENCE: 11
atgggcctcg agccgacgaa gagccggaga gggaggggtc gggayccccg aggaggraac    60
caagcaaaga aggggagact cccgaggraa grtatctcct aagaagagtc gagaarattc   120
tcaagaggag gaggwatccc ctcaaagctg acggaactcc gggaacaagg aaayaggaga   180
aggaacggta gaaagagcg agcctcccga tccgagggc ccggacacct cggctctgga    240
gtcctccgac ctgtgaggtc gagaacctcc gcgcagggag acagccacca ggagaaggca   300

-continued

```
garaaaccac ctccagagga cccccttcagc gaacagagaa gcactctgag gcgtcrggag      360
agnntccata gcgataggag gagatgctag gagtgggcgg cgaccraagc gaggatcgaa      420
agtaaagaaa gcaacgggc tagcaggtgg atgttccgcc tccccagggt cccgagtgag       480
gcttatcccg gggaacccgg ctaagccccg aaatgtctgg ttccgccggc tccacttcca      540
aaaggaggag cggggggact tggarcgyaa ggggccagtt cagtccgtgg ggwttacccc      600
ggagctcccg ttctccacac tccttccccc cgcgggaccc ccaataatnt ggtaagaacc      660
cacccactgg ggtccgacgy tcctaccctt tcttacctgt ggccggcatg gtcccagcct      720
cctcgctggc gccggctggg caacattccg aggggaccgc tcctcggta atggcgaatg       780 ggacccagaw ctctctctag gttcccagag agaaccgaga gaaaactggc tctcccttag      840
ccatccgagt ggacgtctgt cctccttcgg atgcccaggt cggaccgcgg ggaggtggag      900
atgccatgcc gacccgaaga ggaaagaagg actcggacgc gaacccgtga gtggaacctt      960
attcctttat tggggagtac actcgaggag tggaaggcgg ggagacgggg ctcccgggct     1020
taccyacggg aactgctggt tccccttat gtccagtccc tctcccgtcc tggtgaaggr      1080
agactcggga acgttcagca tttgagggac aaagccgccc ccgggcgctc ccctcggagg     1140
tccctgtggt gggttcacat ccccaacccg cgggccggct actcttcttt ccttctctc     1200 gtcttcytcg gtcaacctcc cgagttcctc ttcttcctcc ttgctgagtg actttccycc     1260
cgcgttcagc tgtttcttct tgttctcgag ggccttcctt cttcggtggt cctgtctctc     1320
cttgtcggtg aagtctcccg cgcgagatct cttcctaggt ccggaatcga cctccatccg     1380
atccgtccgg gccctcttcg ccgggggagc tccctccccg tccttcccctt ttcttattat    1440 tccgaggacg ttccccagcc agggattttc gtcctcgagt ctcttgatgg ttctcttggt     1500
cttccggagc cttytctcga ggtcstccgc rtcttttctt gcttggaycc atttctcgag     1560
grtctcctcc cttcctcccc tccgggattt cttctgttcg gactggctca tcctcggata     1620 ggggggcgacg gcgtctgttc tctattttct tcgttctaag aagaggagay agcgtgccgc    1680
ccgcccccag ccccggg                                                     1697
```

<210> SEQ ID NO 12
<211> LENGTH: 645
<212> TYPE: DNA
<213> ORGANISM: hepatitis D virus
<220> FEATURE:
<221> NAME/KEY: CDS
<222> LOCATION: (1)..(645)
<223> OTHER INFORMATION: cDNA of LHD

<400> SEQUENCE: 12

```
atg agc cag tcc gaa cag aag aaa tcc cgg agg gga gga agg gag gag       48
Met Ser Gln Ser Glu Gln Lys Lys Ser Arg Arg Gly Gly Arg Glu Glu
1               5                   10                  15 ayc ctc gag aaa tgg rtc caa gca aga aaa gay gcg gas gac ctc gag       96
Xaa Leu Glu Lys Trp Xaa Gln Ala Arg Lys Asp Ala Xaa Asp Leu Glu
            20                  25                  30 ara agg ctc cgg aag acc aag aga acc atc aag aga ctc gag gac gaa     144
Xaa Arg Leu Arg Lys Thr Lys Arg Thr Ile Lys Arg Leu Glu Asp Glu
        35                  40                  45 aat ccc tgg ctg ggg aac gtc ctc gga ata ata aga aaa ggg aag gac     192
Asn Pro Trp Leu Gly Asn Val Leu Gly Ile Ile Arg Lys Gly Lys Asp
    50                  55                  60 ggg gag gga gct ccc ccg gcg aag agg gcc cgg acg gat cgg atg gag     240
Gly Glu Gly Ala Pro Pro Ala Lys Arg Ala Arg Thr Asp Arg Met Glu
```

```
                                                          -continued
65              70              75              80 gtc gat tcc gga cct agg aag aga tct cgc gcg gga gac ttc acc gac    288
Val Asp Ser Gly Pro Arg Lys Arg Ser Arg Ala Gly Asp Phe Thr Asp
                85              90              95 aag gag aga cag gac cac cga aga agg aag gcc ctc gag aac aag aag    336
Lys Glu Arg Gln Asp His Arg Arg Lys Ala Leu Glu Asn Lys Lys
            100             105             110 aaa cag ctg aac gcg ggr gga aag tca ctc agc aag gag gaa gaa gag    384
Lys Gln Leu Asn Ala Xaa Gly Lys Ser Leu Ser Lys Glu Glu Glu Glu
            115             120             125 gaa ctc ggg agg ttg acc gar gaa gac gag aga agg gaa aga aga gta    432
Glu Leu Gly Arg Leu Thr Glu Glu Asp Glu Arg Arg Glu Arg Arg Val
        130             135             140 gcc ggc ccg cgg gtt ggg gat gtg aac cca cca cag gga cct ccg agg    480
Ala Gly Pro Arg Val Gly Asp Val Asn Pro Pro Gln Gly Pro Pro Arg
145             150             155             160 gga gcg ccc ggg ggc ggc ttt gtc cct caa atg ctg aac gtt ccc gag    528
Gly Ala Pro Gly Gly Gly Phe Val Pro Gln Met Leu Asn Val Pro Glu
                165             170             175 tct ycc ttc acc agg acg gga gag gga ctg gac ata agg ggg aac cag    576
Ser Xaa Phe Thr Arg Thr Gly Glu Gly Leu Asp Ile Arg Gly Asn Gln
            180             185             190 cag ttc ccg tgg gta agc ccg gga gcc ccg tct ccc cgc ctt cca ctc    624
Gln Phe Pro Trp Val Ser Pro Gly Ala Pro Ser Pro Arg Leu Pro Leu
        195             200             205 ctc gag tgt act ccc caa taa                                        645
Leu Glu Cys Thr Pro Gln
    210
```

<210> SEQ ID NO 13
<211> LENGTH: 214
<212> TYPE: PRT
<213> ORGANISM: hepatitis D virus
<220> FEATURE:
<221> NAME/KEY: misc_feature
<222> LOCATION: (17)..(17)
<223> OTHER INFORMATION: The 'Xaa' at location 17 stands for Thr, or
      Ile.
<220> FEATURE:
<221> NAME/KEY: misc_feature
<222> LOCATION: (22)..(22)
<223> OTHER INFORMATION: The 'Xaa' at location 22 stands for Val, or
      Ile.
<220> FEATURE:
<221> NAME/KEY: misc_feature
<222> LOCATION: (29)..(29)
<223> OTHER INFORMATION: The 'Xaa' at location 29 stands for Glu, or
      Asp.
<220> FEATURE:
<221> NAME/KEY: misc_feature
<222> LOCATION: (33)..(33)
<223> OTHER INFORMATION: The 'Xaa' at location 33 stands for Arg, or
      Lys.
<220> FEATURE:
<221> NAME/KEY: misc_feature
<222> LOCATION: (118)..(118)
<223> OTHER INFORMATION: The 'Xaa' at location 118 stands for Gly.
<220> FEATURE:
<221> NAME/KEY: misc_feature
<222> LOCATION: (178)..(178)
<223> OTHER INFORMATION: The 'Xaa' at location 178 stands for Pro, or
      Ser.

<400> SEQUENCE: 13

Met Ser Gln Ser Glu Gln Lys Lys Ser Arg Arg Gly Gly Arg Glu Glu
1               5                   10                  15

Xaa Leu Glu Lys Trp Xaa Gln Ala Arg Lys Asp Ala Xaa Asp Leu Glu

-continued

```
                    20                  25                  30
    Xaa Arg Leu Arg Lys Thr Lys Arg Thr Ile Lys Arg Leu Glu Asp Glu
            35                  40                  45

Asn Pro Trp Leu Gly Asn Val Leu Gly Ile Ile Arg Lys Gly Lys Asp
        50                  55                  60

Gly Glu Gly Ala Pro Pro Ala Lys Arg Ala Arg Thr Asp Arg Met Glu
    65                  70                  75                  80

Val Asp Ser Gly Pro Arg Lys Arg Ser Arg Ala Gly Asp Phe Thr Asp
                    85                  90                  95

Lys Glu Arg Gln Asp His Arg Arg Lys Ala Leu Glu Asn Lys Lys
                100                 105                 110

Lys Gln Leu Asn Ala Xaa Gly Lys Ser Leu Ser Lys Glu Glu Glu
            115                 120                 125

Glu Leu Gly Arg Leu Thr Glu Glu Asp Glu Arg Arg Glu Arg Val
        130                 135                 140

Ala Gly Pro Arg Val Gly Asp Val Asn Pro Gln Gly Pro Pro Arg
    145                 150                 155                 160

Gly Ala Pro Gly Gly Gly Phe Val Pro Gln Met Leu Asn Val Pro Glu
                    165                 170                 175

Ser Xaa Phe Thr Arg Thr Gly Glu Gly Leu Asp Ile Arg Gly Asn Gln
                180                 185                 190

Gln Phe Pro Trp Val Ser Pro Gly Ala Pro Ser Pro Arg Leu Pro Leu
            195                 200                 205

Leu Glu Cys Thr Pro Gln
        210

<210> SEQ ID NO 14
<211> LENGTH: 588
<212> TYPE: DNA
<213> ORGANISM: hepatitis D virus
<220> FEATURE:
<221> NAME/KEY: CDS
<222> LOCATION: (1)..(588)
<223> OTHER INFORMATION: cDNA of sHD

<400> SEQUENCE: 14 atg agc cag tcc gaa cag aag aaa tcc cgg agg gga gga agg gag gag        48
Met Ser Gln Ser Glu Gln Lys Lys Ser Arg Arg Gly Gly Arg Glu Glu
1               5                   10                  15 ayc ctc gag aaa tgg rtc caa gca aga aaa gay gcg gas gac ctc gag        96
Xaa Leu Glu Lys Trp Xaa Gln Ala Arg Lys Asp Ala Xaa Asp Leu Glu
                20                  25                  30 ara agg ctc cgg aag acc aag aga acc atc aag aga ctc gag gac gaa       144
Xaa Arg Leu Arg Lys Thr Lys Arg Thr Ile Lys Arg Leu Glu Asp Glu
        35                  40                  45 aat ccc tgg ctg ggg aac gtc ctc gga ata ata aga aaa ggg aag gac       192
Asn Pro Trp Leu Gly Asn Val Leu Gly Ile Ile Arg Lys Gly Lys Asp
    50                  55                  60 ggg gag gga gct ccc ccg gcg aag agg gcc cgg acg gat cgg atg gag       240
Gly Glu Gly Ala Pro Pro Ala Lys Arg Ala Arg Thr Asp Arg Met Glu
65                  70                  75                  80 gtc gat tcc gga cct agg aag aga tct cgc gcg gga gac ttc acc gac       288
Val Asp Ser Gly Pro Arg Lys Arg Ser Arg Ala Gly Asp Phe Thr Asp
                85                  90                  95 aag gag aga cag gac cac cga aga agg aag gcc ctc gag aac aag aag       336
Lys Glu Arg Gln Asp His Arg Arg Arg Lys Ala Leu Glu Asn Lys Lys
            100                 105                 110 aaa cag ctg aac gcg ggr gga aag tca ctc agc aag gag gaa gaa gag       384
```

-continued

```
Lys Gln Leu Asn Ala Xaa Gly Lys Ser Leu Ser Lys Glu Glu Glu
            115                 120                 125 gaa ctc ggg agg ttg acc gar gaa gac gag aga agg gaa aga aga gta      432
Glu Leu Gly Arg Leu Thr Glu Glu Asp Glu Arg Arg Glu Arg Arg Val
        130                 135                 140 gcc ggc ccg cgg gtt ggg gat gtg aac cca cca cag gga cct ccg agg      480
Ala Gly Pro Arg Val Gly Asp Val Asn Pro Pro Gln Gly Pro Pro Arg
145                 150                 155                 160 gga gcg ccc ggg ggc ggc ttt gtc cct caa atg ctg aac gtt ccc gag      528
Gly Ala Pro Gly Gly Gly Phe Val Pro Gln Met Leu Asn Val Pro Glu
                165                 170                 175 tct ycc ttc acc agg acg gga gag gga ctg gac ata agg ggg aac cag      576
Ser Xaa Phe Thr Arg Thr Gly Glu Gly Leu Asp Ile Arg Gly Asn Gln
            180                 185                 190 cag ttc ccg tag                                                      588
Gln Phe Pro
        195

<210> SEQ ID NO 15
<211> LENGTH: 195
<212> TYPE: PRT
<213> ORGANISM: hepatitis D virus
<220> FEATURE:
<221> NAME/KEY: misc_feature
<222> LOCATION: (17)..(17)
<223> OTHER INFORMATION: The 'Xaa' at location 17 stands for Thr, or
      Ile.
<220> FEATURE:
<221> NAME/KEY: misc_feature
<222> LOCATION: (22)..(22)
<223> OTHER INFORMATION: The 'Xaa' at location 22 stands for Val, or
      Ile.
<220> FEATURE:
<221> NAME/KEY: misc_feature
<222> LOCATION: (29)..(29)
<223> OTHER INFORMATION: The 'Xaa' at location 29 stands for Glu, or
      Asp.
<220> FEATURE:
<221> NAME/KEY: misc_feature
<222> LOCATION: (33)..(33)
<223> OTHER INFORMATION: The 'Xaa' at location 33 stands for Arg, or
      Lys.
<220> FEATURE:
<221> NAME/KEY: misc_feature
<222> LOCATION: (118)..(118)
<223> OTHER INFORMATION: The 'Xaa' at location 118 stands for Gly.
<220> FEATURE:
<221> NAME/KEY: misc_feature
<222> LOCATION: (178)..(178)
<223> OTHER INFORMATION: The 'Xaa' at location 178 stands for Pro, or
      Ser.

<400> SEQUENCE: 15

Met Ser Gln Ser Glu Gln Lys Lys Ser Arg Arg Gly Gly Arg Glu Glu
1               5                   10                  15

Xaa Leu Glu Lys Trp Xaa Gln Ala Arg Lys Asp Ala Xaa Asp Leu Glu
            20                  25                  30

Xaa Arg Leu Arg Lys Thr Lys Arg Thr Ile Lys Arg Leu Glu Asp Glu
        35                  40                  45

Asn Pro Trp Leu Gly Asn Val Leu Gly Ile Ile Arg Lys Gly Lys Asp
    50                  55                  60

Gly Glu Gly Ala Pro Pro Ala Lys Arg Ala Arg Thr Asp Arg Met Glu
65                  70                  75                  80

Val Asp Ser Gly Pro Arg Lys Arg Ser Arg Ala Gly Asp Phe Thr Asp
                85                  90                  95

Lys Glu Arg Gln Asp His Arg Arg Arg Lys Ala Leu Glu Asn Lys Lys
```

-continued

```
                100                 105                 110
Lys Gln Leu Asn Ala Xaa Gly Lys Ser Leu Ser Lys Glu Glu Glu
            115                 120                 125

Glu Leu Gly Arg Leu Thr Glu Glu Asp Glu Arg Arg Glu Arg Arg Val
        130                 135                 140

Ala Gly Pro Arg Val Gly Asp Val Asn Pro Gln Gly Pro Pro Arg
145                 150                 155                 160

Gly Ala Pro Gly Gly Phe Val Pro Gln Met Leu Asn Val Pro Glu
                165                 170                 175

Ser Xaa Phe Thr Arg Thr Gly Glu Gly Leu Asp Ile Arg Gly Asn Gln
        180                 185                 190

Gln Phe Pro
        195
```

<210> SEQ ID NO 16
<211> LENGTH: 1697
<212> TYPE: DNA
<213> ORGANISM: hepatitis D virus
<220> FEATURE:
<221> NAME/KEY: source
<222> LOCATION: (1)..(1697)
<223> OTHER INFORMATION: complete genomic sequence of dFR910

<400> SEQUENCE: 16

```
atgggcctcc gtgccgacga agaatcggat cgataggaag tgggaggccc gagaggggct    60
ccaagcaaag agaggaggaa tcccggggaa aaattctccc aagaagagtc gagagtaatc   120
tcaagaagag gagatttccc agacgccggt ggagcaccag ggaacaagga acaggagag    180
gaacggtaga aaagagcgag cctcccgatc cgagggggcc ctggacccct cagctctgga   240
gtcctccgac ccgtgaggtc gaggatcccc gcgcagggag acagccaccc ggagaagaca   300
gagaaatcac ctccagagaa accctctcag cgaacaaaga ggcgctctga ggcgttgggg   360
cgagtccata gcgatgggag gggatgctag gagtcggcag cgaccgaagc gaggagaaaa   420
gtaaagaaag caacggggct agcaggtgga tgttccgcct cccgggaggt cccgagtgag   480
gcttatcccg gggaactcgg ctaagccccg aaatgtctag ttccactgtc tccacttcca   540
aagggaggag cgggtggacc tggaacatga ggggaccagt caatccgtgg gattgccccg   600
gacctccggy tctccacact ccttcccccc tgcgggcttc ccagtaaaat gaaagaaacc   660
cacccactgg ggtccgacgy cctcccccct tcttacctgt ggccggcatg gtcccagcct   720
ccyccgctgg ccggctggg caacattccg aggggaccgt ccctcggtaa tggcgaatgg   780
gacccagaac tctctccagg ttcccagaga gaaccgagag aaaactggct ctcccttagc   840
catccgagtg gacgttyygt cctccttcgg atgcccaggt cggaccgcgg ggaggtggag   900
aygccatgcc gacccgaaga aggaaagaag gactcggacg cgaacccgtg agtggaactc   960
tttatctttt actggggagt acactcgagg agtggaaggc ggggaggccg ggtcccggg   1020
tctacccacg ggaattgctg gtttccccctt acgtccagtc cacttcccgt cctggagaag  1080
ggagactcgg gaacatctag catttgaggg acaaagccgc cccgggcgc tccctcgga   1140
ggtccctcgg gtgggttcac atccccaacc cgcgggccgg ctactcttct ttcccttctc  1200
tcgtcttcct cggtcaactt ccggagttcc tcttcctcct ccctgctgag tgactttccc  1260
cccgcgctca gctgattctt cttgttctcg agggctttcc ttcttcggtg atcctttctc  1320
tcctggtcgt tgaagtctcc cgctcgggtc tcttcctag gtccggagtc gacctccatc   1380
tgatccgtcc gggccctttt cgccggggga gctccctccc cgtccttccc ttttcttatt   1440
```

```
attccaagga tgttccccag ccagggattt tcatcctcga gtttcttgat ggttctcttg    1500
gtcttccgga gcyttttctc gagatcctcc gagtcttttc ttgcttgcac ccacttctcg    1560
aggatctcct cccttcctcc tctccgagct ttcttcgatt cggactggct catcctcgga    1620 taggggggaga cggcttctgt tctcttattc ttccttttcg aagaggagac agcttgccgc    1680
ccctccccca ccccggg                                                   1697
```

```
<210> SEQ ID NO 17
<211> LENGTH: 645
<212> TYPE: DNA
<213> ORGANISM: hepatitis D virus
<220> FEATURE:
<221> NAME/KEY: CDS
<222> LOCATION: (1)..(645)
<223> OTHER INFORMATION: cDNA of LHD

<400> SEQUENCE: 17
```

| | | | | | | | | | | | | | | | | |
|---|---|---|---|---|---|---|---|---|---|---|---|---|---|---|---|---|
| atg | agc | cag | tcc | gaa | tcg | aag | aaa | gct | cgg | aga | gga | gga | agg | gag | gag | 48 |
| Met | Ser | Gln | Ser | Glu | Ser | Lys | Lys | Ala | Arg | Arg | Gly | Gly | Arg | Glu | Glu | |
| 1 | | | | 5 | | | | | 10 | | | | | 15 | | |

| atc | ctc | gag | aag | tgg | gtg | caa | gca | aga | aaa | gac | tcg | gag | gat | ctc | gag | 96 |
|---|---|---|---|---|---|---|---|---|---|---|---|---|---|---|---|---|
| Ile | Leu | Glu | Lys | Trp | Val | Gln | Ala | Arg | Lys | Asp | Ser | Glu | Asp | Leu | Glu | |
| | | | 20 | | | | | 25 | | | | | 30 | | | |

| aaa | arg | ctc | cgg | aag | acc | aag | aga | acc | atc | aag | aaa | ctc | gag | gat | gaa | 144 |
|---|---|---|---|---|---|---|---|---|---|---|---|---|---|---|---|---|
| Lys | Xaa | Leu | Arg | Lys | Thr | Lys | Arg | Thr | Ile | Lys | Lys | Leu | Glu | Asp | Glu | |
| | 35 | | | | | 40 | | | | | 45 | | | | | |

| aat | ccc | tgg | ctg | ggg | aac | atc | ctt | gga | ata | ata | aga | aaa | ggg | aag | gac | 192 |
|---|---|---|---|---|---|---|---|---|---|---|---|---|---|---|---|---|
| Asn | Pro | Trp | Leu | Gly | Asn | Ile | Leu | Gly | Ile | Ile | Arg | Lys | Gly | Lys | Asp | |
| 50 | | | | | 55 | | | | | 60 | | | | | | |

| ggg | gag | gga | gct | ccc | ccg | gcg | aaa | agg | gcc | cgg | acg | gat | cag | atg | gag | 240 |
|---|---|---|---|---|---|---|---|---|---|---|---|---|---|---|---|---|
| Gly | Glu | Gly | Ala | Pro | Pro | Ala | Lys | Arg | Ala | Arg | Thr | Asp | Gln | Met | Glu | |
| 65 | | | | 70 | | | | | 75 | | | | | 80 | | |

| gtc | gac | tcc | gga | cct | agg | aag | agg | acc | cga | gcg | gga | gac | ttc | acc | gac | 288 |
|---|---|---|---|---|---|---|---|---|---|---|---|---|---|---|---|---|
| Val | Asp | Ser | Gly | Pro | Arg | Lys | Arg | Thr | Arg | Ala | Gly | Asp | Phe | Thr | Asp | |
| | | | | 85 | | | | | 90 | | | | | 95 | | |

| cag | gag | aga | aag | gat | cac | cga | aga | agg | aaa | gcc | ctc | gag | aac | aag | aag | 336 |
|---|---|---|---|---|---|---|---|---|---|---|---|---|---|---|---|---|
| Gln | Glu | Arg | Lys | Asp | His | Arg | Arg | Arg | Lys | Ala | Leu | Glu | Asn | Lys | Lys | |
| | | | 100 | | | | | 105 | | | | | 110 | | | |

| aat | cag | ctg | agc | gcg | ggg | gga | aag | tca | ctc | agc | agg | gag | gag | gaa | gag | 384 |
|---|---|---|---|---|---|---|---|---|---|---|---|---|---|---|---|---|
| Asn | Gln | Leu | Ser | Ala | Gly | Gly | Lys | Ser | Leu | Ser | Arg | Glu | Glu | Glu | Glu | |
| | 115 | | | | | 120 | | | | | 125 | | | | | |

| gaa | ctc | cgg | aag | ttg | acc | gag | gaa | gac | gag | aga | agg | gaa | aga | aga | gta | 432 |
|---|---|---|---|---|---|---|---|---|---|---|---|---|---|---|---|---|
| Glu | Leu | Arg | Lys | Leu | Thr | Glu | Glu | Asp | Glu | Arg | Arg | Glu | Arg | Arg | Val | |
| 130 | | | | | 135 | | | | | 140 | | | | | | |

| gcc | ggc | ccg | cgg | gtt | ggg | gat | gtg | aac | cca | ccc | gag | gga | cct | ccg | agg | 480 |
|---|---|---|---|---|---|---|---|---|---|---|---|---|---|---|---|---|
| Ala | Gly | Pro | Arg | Val | Gly | Asp | Val | Asn | Pro | Pro | Glu | Gly | Pro | Pro | Arg | |
| 145 | | | | | 150 | | | | | 155 | | | | | 160 | |

| gga | gcg | ccc | ggg | ggc | ggc | ttt | gtc | cct | caa | atg | cta | gat | gtt | ccc | gag | 528 |
|---|---|---|---|---|---|---|---|---|---|---|---|---|---|---|---|---|
| Gly | Ala | Pro | Gly | Gly | Gly | Phe | Val | Pro | Gln | Met | Leu | Asp | Val | Pro | Glu | |
| | | | | 165 | | | | | 170 | | | | | 175 | | |

| tct | ccc | ttc | tcc | agg | acg | gga | agt | gga | ctg | gac | gta | agg | gga | aac | cag | 576 |
|---|---|---|---|---|---|---|---|---|---|---|---|---|---|---|---|---|
| Ser | Pro | Phe | Ser | Arg | Thr | Gly | Ser | Gly | Leu | Asp | Val | Arg | Gly | Asn | Gln | |
| | | | 180 | | | | | 185 | | | | | 190 | | | |

| caa | ttc | ccg | tgg | gtg | gac | ccg | gga | ccc | cgg | cct | ccc | gcc | ctt | cca | ctc | 624 |
|---|---|---|---|---|---|---|---|---|---|---|---|---|---|---|---|---|
| Gln | Phe | Pro | Trp | Val | Asp | Pro | Gly | Pro | Arg | Pro | Pro | Arg | Leu | Pro | Leu | |
| | 195 | | | | | 200 | | | | | 205 | | | | | |

| ctc | gag | tgt | act | ccc | cag | taa | | | | | | | | | | 645 |
|---|---|---|---|---|---|---|---|---|---|---|---|---|---|---|---|---|
| Leu | Glu | Cys | Thr | Pro | Gln | | | | | | | | | | | |
| | 210 | | | | | | | | | | | | | | | |

<210> SEQ ID NO 18
<211> LENGTH: 214
<212> TYPE: PRT
<213> ORGANISM: hepatitis D virus
<220> FEATURE:
<221> NAME/KEY: misc_feature
<222> LOCATION: (34)..(34)
<223> OTHER INFORMATION: The 'Xaa' at location 34 stands for Arg, or Lys.

<400> SEQUENCE: 18

```
Met Ser Gln Ser Glu Ser Lys Lys Ala Arg Arg Gly Gly Arg Glu Glu
1               5                   10                  15

Ile Leu Glu Lys Trp Val Gln Ala Arg Lys Asp Ser Glu Asp Leu Glu
            20                  25                  30

Lys Xaa Leu Arg Lys Thr Lys Arg Thr Ile Lys Lys Leu Glu Asp Glu
        35                  40                  45

Asn Pro Trp Leu Gly Asn Ile Leu Gly Ile Ile Arg Lys Gly Lys Asp
    50                  55                  60

Gly Glu Gly Ala Pro Pro Ala Lys Arg Ala Arg Thr Asp Gln Met Glu
65                  70                  75                  80

Val Asp Ser Gly Pro Arg Lys Arg Thr Arg Ala Gly Asp Phe Thr Asp
                85                  90                  95

Gln Glu Arg Lys Asp His Arg Arg Lys Ala Leu Glu Asn Lys Lys
            100                 105                 110

Asn Gln Leu Ser Ala Gly Gly Lys Ser Leu Ser Arg Glu Glu Glu Glu
        115                 120                 125

Glu Leu Arg Lys Leu Thr Glu Glu Asp Glu Arg Arg Glu Arg Arg Val
    130                 135                 140

Ala Gly Pro Arg Val Gly Asp Val Asn Pro Glu Gly Pro Pro Arg
145                 150                 155                 160

Gly Ala Pro Gly Gly Phe Val Pro Gln Met Leu Asp Val Pro Glu
                165                 170                 175

Ser Pro Phe Ser Arg Thr Gly Ser Gly Leu Asp Val Arg Gly Asn Gln
            180                 185                 190

Gln Phe Pro Trp Val Asp Pro Gly Pro Arg Pro Arg Leu Pro Leu
        195                 200                 205

Leu Glu Cys Thr Pro Gln
    210
```

<210> SEQ ID NO 19
<211> LENGTH: 588
<212> TYPE: DNA
<213> ORGANISM: hepatitis D virus
<220> FEATURE:
<221> NAME/KEY: CDS
<222> LOCATION: (1)..(588)
<223> OTHER INFORMATION: cDNA of sHD

<400> SEQUENCE: 19

```
atg agc cag tcc gaa tcg aag aaa gct cgg aga gga gga agg gag gag      48
Met Ser Gln Ser Glu Ser Lys Lys Ala Arg Arg Gly Gly Arg Glu Glu
1               5                   10                  15 atc ctc gag aag tgg gtg caa gca aga aaa gac tcg gag gat ctc gag      96
Ile Leu Glu Lys Trp Val Gln Ala Arg Lys Asp Ser Glu Asp Leu Glu
            20                  25                  30 aaa arg ctc cgg aag acc aag aga acc atc aag aaa ctc gag gat gaa     144
Lys Xaa Leu Arg Lys Thr Lys Arg Thr Ile Lys Lys Leu Glu Asp Glu
        35                  40                  45
```

```
aat ccc tgg ctg ggg aac atc ctt gga ata ata aga aaa ggg aag gac       192
Asn Pro Trp Leu Gly Asn Ile Leu Gly Ile Ile Arg Lys Gly Lys Asp
 50                  55                  60 ggg gag gga gct ccc ccg gcg aaa agg gcc cgg acg gat cag atg gag       240
Gly Glu Gly Ala Pro Pro Ala Lys Arg Ala Arg Thr Asp Gln Met Glu
 65                  70                  75                  80 gtc gac tcc gga cct agg aag agg acc cga gcg gga gac ttc acc gac       288
Val Asp Ser Gly Pro Arg Lys Arg Thr Arg Ala Gly Asp Phe Thr Asp
                 85                  90                  95 cag gag aga aag gat cac cga aga agg aaa gcc ctc gag aac aag aag       336
Gln Glu Arg Lys Asp His Arg Arg Arg Lys Ala Leu Glu Asn Lys Lys
                100                 105                 110 aat cag ctg agc gcg ggg gga aag tca ctc agc agg gag gag gaa gag       384
Asn Gln Leu Ser Ala Gly Gly Lys Ser Leu Ser Arg Glu Glu Glu Glu
            115                 120                 125 gaa ctc cgg aag ttg acc gag gaa gac gag aga agg gaa aga aga gta       432
Glu Leu Arg Lys Leu Thr Glu Glu Asp Glu Arg Arg Glu Arg Arg Val
130                 135                 140 gcc ggc ccg cgg gtt ggg gat gtg aac cca ccc gag gga cct ccg agg       480
Ala Gly Pro Arg Val Gly Asp Val Asn Pro Pro Glu Gly Pro Pro Arg
145                 150                 155                 160 gga gcg ccc ggg ggc ggc ttt gtc cct caa atg cta gat gtt ccc gag       528
Gly Ala Pro Gly Gly Gly Phe Val Pro Gln Met Leu Asp Val Pro Glu
                165                 170                 175 tct ccc ttc tcc agg acg gga agt gga ctg gac gta agg gga aac cag       576
Ser Pro Phe Ser Arg Thr Gly Ser Gly Leu Asp Val Arg Gly Asn Gln
                180                 185                 190 caa ttc ccg tga                                                       588
Gln Phe Pro
        195

<210> SEQ ID NO 20
<211> LENGTH: 195
<212> TYPE: PRT
<213> ORGANISM: hepatitis D virus
<220> FEATURE:
<221> NAME/KEY: misc_feature
<222> LOCATION: (34)..(34)
<223> OTHER INFORMATION: The 'Xaa' at location 34 stands for Arg, or
      Lys.

<400> SEQUENCE: 20

Met Ser Gln Ser Glu Ser Lys Lys Ala Arg Arg Gly Gly Arg Glu Glu
 1               5                   10                  15

Ile Leu Glu Lys Trp Val Gln Ala Arg Lys Asp Ser Glu Asp Leu Glu
                20                  25                  30

Lys Xaa Leu Arg Lys Thr Lys Arg Thr Ile Lys Lys Leu Glu Asp Glu
            35                  40                  45

Asn Pro Trp Leu Gly Asn Ile Leu Gly Ile Ile Arg Lys Gly Lys Asp
 50                  55                  60

Gly Glu Gly Ala Pro Pro Ala Lys Arg Ala Arg Thr Asp Gln Met Glu
 65                  70                  75                  80

Val Asp Ser Gly Pro Arg Lys Arg Thr Arg Ala Gly Asp Phe Thr Asp
                 85                  90                  95

Gln Glu Arg Lys Asp His Arg Arg Arg Lys Ala Leu Glu Asn Lys Lys
                100                 105                 110

Asn Gln Leu Ser Ala Gly Gly Lys Ser Leu Ser Arg Glu Glu Glu Glu
            115                 120                 125

Glu Leu Arg Lys Leu Thr Glu Glu Asp Glu Arg Arg Glu Arg Arg Val
130                 135                 140
```

```
Ala Gly Pro Arg Val Gly Asp Val Asn Pro Glu Gly Pro Pro Arg
145                 150                 155                 160

Gly Ala Pro Gly Gly Gly Phe Val Pro Gln Met Leu Asp Val Pro Glu
                165                 170                 175

Ser Pro Phe Ser Arg Thr Gly Ser Gly Leu Asp Val Arg Gly Asn Gln
            180                 185                 190

Gln Phe Pro
        195

<210> SEQ ID NO 21
<211> LENGTH: 1687
<212> TYPE: DNA
<213> ORGANISM: hepatitis D virus
<220> FEATURE:
<221> NAME/KEY: source
<222> LOCATION: (1)..(1687)
<223> OTHER INFORMATION: complete genomic sequence of dFr48

<400> SEQUENCE: 21
agtgggccac aagccggcgg agagatcgag gatttgggga ggagaggggga accgaggggg      60 gttcgaactc aagaagagaa gattttcgag gaaatactcc caagaagttc ccggagggat     120
ccaagagacg gaygactttc cccyattggt tgggaaaagt cccggaacca ggaaatggga     180
aagagacggt agaaaagagc gagcctccca gttttcgagt agtcccggac ctatctaaat     240
tggagtcatc cgaccgtatg gagaaaattt ccgacaagag gtgatccact gagggtttgc     300
ggaaaaatca cctccagagg accccttcag cgaacgaaag agactggaag ccccagagga     360
agaccatagc catggggaga gatgctagga gtgggggggcg accggaacga ggagaaaagt     420
aaagagagca acggggctag cgagtggatg ttccgcctcc ccggggagcc gagtgaggct     480
tatcccggag tgccgggcaa gtcccccccat gcccgttcca cggctcccctt ccagaagggc     540 gggggtggcc tggagcgtcg ggccccagca gtccgtggaa ttcaccctct taccgcttct     600
ccacactcct tcccccctgc gggctccccc cataagatga cgaggacccc actcatcggg     660
gtccgcagtc tcatccttc ttacctgatg gccggcatgg tcccagcctc ctcgctggcg     720
ccggctgggc aacattccga ggggaccgtc cctcggyaat ggcgaatggg acccagaact     780
ctctcagaat ctagggagat ctcccagatt cgagagaaaa ctggctctcc cttagccatc     840
cgagtggacg tctgtcctcc tacggatgcc caggtcggac cgcggggagg tggagatgcc     900
atgccgaccc gaagaggaaa gaaggactcg gacgcgaacc cgtgagtgga aacctcgttc     960
tttattgggg agtacactcg aggagtggaa ggcgggggagg gcgggagga gtgttacccy    1020 acggaactg ctgagtgccc ctgacgtcca gaccctcccc cgtccgggag aatggagatt    1080
cgggaacgtg aagcatggtg gggacgaagc cccctccggg cgctcccctc ggatctccgc    1140
cgggtgggtt cacatcccca acccgcgggc cggctgttct tcttttcctt tgctcgtctt    1200 cccccggtcag cctcccgagt tcctcttctt cttccctgct gaggttcttc cctccggcgg    1260
ccagttgctt cttcttgttc tcgagggcct tccttcgtcg gtgatcccgc ctctcctcgt    1320
cggtgaaacc cgacttgtgc ggctttcccc taggtccgga atcgacctcc atttgatccg    1380
tccgggcctt cttcgttggg ggtgctccct cccgtcctt tccctttctt atgattccga    1440
tgatattccc caaccaggga ttgtcatcct cgagtttctt gaggcccttc tgggtcttcc    1500
ggagcttcct ttcgagatcc tctcgatttt ttcttagttc cacccacttc tcgaggatct    1560
cttccctccc acctcgtttt ctcttctgct cggcggggcc catctcgact gggggcggc    1620
```

```
gtcctcagta ctctcttact ttctcaagaa aagaggagac tgctggtcgc ccgcccccgt    1680
gttcgag                                                              1687

<210> SEQ ID NO 22
<211> LENGTH: 642
<212> TYPE: DNA
<213> ORGANISM: hepatitis D virus
<220> FEATURE:
<221> NAME/KEY: CDS
<222> LOCATION: (1)..(642)
<223> OTHER INFORMATION: cDNA of LHD

<400> SEQUENCE: 22 atg ggc ccc gcc gag cag aag aga aaa cga ggt ggg agg gaa gag atc      48
Met Gly Pro Ala Glu Gln Lys Arg Lys Arg Gly Gly Arg Glu Glu Ile
1               5                   10                  15 ctc gag aag tgg gtg gaa cta aga aaa aat cga gag gat ctc gaa agg      96
Leu Glu Lys Trp Val Glu Leu Arg Lys Asn Arg Glu Asp Leu Glu Arg
                20                  25                  30 aag ctc cgg aag acc cag aag ggc ctc aag aaa ctc gag gat gac aat     144
Lys Leu Arg Lys Thr Gln Lys Gly Leu Lys Lys Leu Glu Asp Asp Asn
            35                  40                  45 ccc tgg ttg ggg aat atc atc gga atc ata aga aag gga aag gac ggg     192
Pro Trp Leu Gly Asn Ile Ile Gly Ile Ile Arg Lys Gly Lys Asp Gly
        50                  55                  60 gag gga gca ccc cca acg aag aag gcc cgg acg gat caa atg gag gtc     240
Glu Gly Ala Pro Pro Thr Lys Lys Ala Arg Thr Asp Gln Met Glu Val
65                  70                  75                  80 gat tcc gga cct agg gga aag ccg cac aag tcg ggt ttc acc gac gag     288
Asp Ser Gly Pro Arg Gly Lys Pro His Lys Ser Gly Phe Thr Asp Glu
                85                  90                  95 gag agg cgg gat cac cga cga agg aag gcc ctc gag aac aag aag aag     336
Glu Arg Arg Asp His Arg Arg Arg Lys Ala Leu Glu Asn Lys Lys Lys
                100                 105                 110 caa ctg gcc gcc gga ggg aag aac ctc agc agg gaa gaa gaa gag gaa     384
Gln Leu Ala Ala Gly Gly Lys Asn Leu Ser Arg Glu Glu Glu Glu Glu
            115                 120                 125 ctc ggg agg ctg acc ggg gaa gac gag caa agg aaa aga aga aca gcc     432
Leu Gly Arg Leu Thr Gly Glu Asp Glu Gln Arg Lys Arg Arg Thr Ala
        130                 135                 140 ggc ccg cgg gtt ggg gat gtg aac cca ccc gga gat ccg agg gga         480
Gly Pro Arg Val Gly Asp Val Asn Pro Pro Gly Asp Pro Arg Gly
145                 150                 155                 160 gcg ccc gga ggg ggc ttc gtc ccc acc atg ctt cac gtt ccc gaa tct     528
Ala Pro Gly Gly Gly Phe Val Pro Thr Met Leu His Val Pro Glu Ser
                165                 170                 175 cca ttc tcc cgg acg ggg gag ggt ctg gac gtc agg ggc act cag cag     576
Pro Phe Ser Arg Thr Gly Glu Gly Leu Asp Val Arg Gly Thr Gln Gln
            180                 185                 190 ttc ccg tgg ggt aac act cct ccc cgc cct ccc cgc ctt cca ctc ctc     624
Phe Pro Trp Gly Asn Thr Pro Pro Arg Pro Arg Leu Pro Leu Leu
        195                 200                 205 gag tgt act ccc caa taa                                             642
Glu Cys Thr Pro Gln
    210

<210> SEQ ID NO 23
<211> LENGTH: 213
<212> TYPE: PRT
<213> ORGANISM: hepatitis D virus

<400> SEQUENCE: 23
```

```
Met Gly Pro Ala Glu Gln Lys Arg Lys Arg Gly Gly Arg Glu Glu Ile
1               5                   10                  15

Leu Glu Lys Trp Val Glu Leu Arg Lys Asn Arg Glu Asp Leu Glu Arg
            20                  25                  30

Lys Leu Arg Lys Thr Gln Lys Gly Leu Lys Lys Leu Glu Asp Asp Asn
        35                  40                  45

Pro Trp Leu Gly Asn Ile Ile Gly Ile Ile Arg Lys Gly Lys Asp Gly
    50                  55                  60

Glu Gly Ala Pro Pro Thr Lys Lys Ala Arg Thr Asp Gln Met Glu Val
65              70                  75                  80

Asp Ser Gly Pro Arg Gly Lys Pro His Lys Ser Gly Phe Thr Asp Glu
                85                  90                  95

Glu Arg Arg Asp His Arg Arg Lys Ala Leu Glu Asn Lys Lys Lys
                100                 105                 110

Gln Leu Ala Ala Gly Gly Lys Asn Leu Ser Arg Glu Glu Glu Glu
            115                 120                 125

Leu Gly Arg Leu Thr Gly Glu Asp Glu Gln Arg Lys Arg Arg Thr Ala
    130                 135                 140

Gly Pro Arg Val Gly Asp Val Asn Pro Pro Gly Gly Asp Pro Arg Gly
145                 150                 155                 160

Ala Pro Gly Gly Gly Phe Val Pro Thr Met Leu His Val Pro Glu Ser
                165                 170                 175

Pro Phe Ser Arg Thr Gly Glu Gly Leu Asp Val Arg Gly Thr Gln Gln
            180                 185                 190

Phe Pro Trp Gly Asn Thr Pro Pro Arg Pro Pro Arg Leu Pro Leu Leu
        195                 200                 205

Glu Cys Thr Pro Gln
        210

<210> SEQ ID NO 24
<211> LENGTH: 585
<212> TYPE: DNA
<213> ORGANISM: hepatitis D virus
<220> FEATURE:
<221> NAME/KEY: CDS
<222> LOCATION: (1)..(585)
<223> OTHER INFORMATION: cDNA of sHD

<400> SEQUENCE: 24 atg ggc ccc gcc gag cag aag aga aaa cga ggt ggg agg gaa gag atc      48
Met Gly Pro Ala Glu Gln Lys Arg Lys Arg Gly Gly Arg Glu Glu Ile
1               5                   10                  15 ctc gag aag tgg gtg gaa cta aga aaa aat cga gag gat ctc gaa agg      96
Leu Glu Lys Trp Val Glu Leu Arg Lys Asn Arg Glu Asp Leu Glu Arg
            20                  25                  30 aag ctc cgg aag acc cag aag ggc ctc aag aaa ctc gag gat gac aat     144
Lys Leu Arg Lys Thr Gln Lys Gly Leu Lys Lys Leu Glu Asp Asp Asn
        35                  40                  45 ccc tgg ttg ggg aat atc atc gga atc ata aga aag gga aag gac ggg     192
Pro Trp Leu Gly Asn Ile Ile Gly Ile Ile Arg Lys Gly Lys Asp Gly
    50                  55                  60 gag gga gca ccc cca acg aag aag gcc cgg acg gat caa atg gag gtc     240
Glu Gly Ala Pro Pro Thr Lys Lys Ala Arg Thr Asp Gln Met Glu Val
65              70                  75                  80 gat tcc gga cct agg gga aag ccg cac aag tcg ggt ttc acc gac gag     288
Asp Ser Gly Pro Arg Gly Lys Pro His Lys Ser Gly Phe Thr Asp Glu
                85                  90                  95
```

```
gag agg cgg gat cac cga cga agg aag gcc ctc gag aac aag aag aag      336
Glu Arg Arg Asp His Arg Arg Arg Lys Ala Leu Glu Asn Lys Lys Lys
            100                 105                 110 caa ctg gcc gcc gga ggg aag aac ctc agc agg gaa gaa gag gaa          384
Gln Leu Ala Ala Gly Gly Lys Asn Leu Ser Arg Glu Glu Glu Glu
        115                 120                 125 ctc ggg agg ctg acc ggg gaa gac gag caa agg aaa aga aga aca gcc      432
Leu Gly Arg Leu Thr Gly Glu Asp Glu Gln Arg Lys Arg Arg Thr Ala
    130                 135                 140 ggc ccg cgg gtt ggg gat gtg aac cca ccc gga gat ccg agg gga          480
Gly Pro Arg Val Gly Asp Val Asn Pro Pro Gly Asp Pro Arg Gly
145                 150                 155                 160 gcg ccc gga ggg ggc ttc gtc ccc acc atg ctt cac gtt ccc gaa tct      528
Ala Pro Gly Gly Gly Phe Val Pro Thr Met Leu His Val Pro Glu Ser
                165                 170                 175 cca ttc tcc cgg acg ggg gag ggt ctg gac gtc agg ggc act cag cag      576
Pro Phe Ser Arg Thr Gly Glu Gly Leu Asp Val Arg Gly Thr Gln Gln
            180                 185                 190 ttc ccg tag                                                          585
Phe Pro
```

<210> SEQ ID NO 25
<211> LENGTH: 194
<212> TYPE: PRT
<213> ORGANISM: hepatitis D virus

<400> SEQUENCE: 25

Met Gly Pro Ala Glu Gln Lys Arg Lys Arg Gly Gly Arg Glu Glu Ile
1               5                   10                  15

Leu Glu Lys Trp Val Glu Leu Arg Lys Asn Arg Glu Asp Leu Glu Arg
            20                  25                  30

Lys Leu Arg Lys Thr Gln Lys Gly Leu Lys Lys Leu Glu Asp Asp Asn
        35                  40                  45

Pro Trp Leu Gly Asn Ile Ile Gly Ile Ile Arg Lys Gly Lys Asp Gly
    50                  55                  60

Glu Gly Ala Pro Pro Thr Lys Lys Ala Arg Thr Asp Gln Met Glu Val
65                  70                  75                  80

Asp Ser Gly Pro Arg Gly Lys Pro His Lys Ser Gly Phe Thr Asp Glu
                85                  90                  95

Glu Arg Arg Asp His Arg Arg Arg Lys Ala Leu Glu Asn Lys Lys Lys
            100                 105                 110

Gln Leu Ala Ala Gly Gly Lys Asn Leu Ser Arg Glu Glu Glu Glu Glu
        115                 120                 125

Leu Gly Arg Leu Thr Gly Glu Asp Glu Gln Arg Lys Arg Arg Thr Ala
    130                 135                 140

Gly Pro Arg Val Gly Asp Val Asn Pro Pro Gly Asp Pro Arg Gly
145                 150                 155                 160

Ala Pro Gly Gly Gly Phe Val Pro Thr Met Leu His Val Pro Glu Ser
                165                 170                 175

Pro Phe Ser Arg Thr Gly Glu Gly Leu Asp Val Arg Gly Thr Gln Gln
            180                 185                 190

Phe Pro

<210> SEQ ID NO 26
<211> LENGTH: 1680
<212> TYPE: DNA
<213> ORGANISM: hepatitis D virus
<220> FEATURE:

<210> SEQ ID NO 26
<211> LENGTH: 1680
<212> TYPE: DNA
<213> ORGANISM: homo sapiens
<220> FEATURE:
<221> NAME/KEY: source
<222> LOCATION: (1)..(1680)
<223> OTHER INFORMATION: complete genomic sequence of dFr644

<400> SEQUENCE: 26

| | | | | | |
|---|---|---|---|---|---|
| atgggccaag | agccgacgaa | gaggtcgaag | gaggagaagg | agtgagtccc | caaggggttc | 60 |
| gaagccaaag | agtggaaaca | ctcgaggaag | agggagtccc | aagagggcga | ggggagcttt | 120 |
| caggagggag | ggtgaatccc | cgagrcgctg | gagactcccg | gaatgaggaa | agtggggata | 180 |
| ggctaggtag | aaaagagcga | gcctcccaaa | tcgagattgc | cctgaaccta | tcragtttgg | 240 |
| agtcatccga | gcttagggtt | gaatgtagcg | cagagggagg | aagccaccag | gagccggaga | 300 |
| caagacacct | ccagaggacc | ccttcagcga | acagaagagt | ctgtccccag | atgagaagag | 360 |
| cgtagctaga | gggggagatg | ctgggagtag | ggggagatcg | aagcgaggag | gaaagtaaag | 420 |
| atggcaacgg | ggctagcagg | agggtgttcc | gccccccggc | ggggccgagt | gaggcttatc | 480 |
| ccggggaact | cggactggtc | ccggactgcc | ggctccaggg | gcccactcca | aaggaccgag | 540 |
| ggcaggactt | ggagcaccgg | gaattccgag | caactccatg | gtagactccg | tcccccttct | 600 |
| ccacactcct | tcccccgcg | ggccccccg | taaagtggag | aacccactc | cgcagggtcc | 660 |
| gcgccctcct | cccttttctta | cctgtggccg | gcatggtccc | agcctcctcg | cggcgccggc | 720 |
| cgggcaacat | tccgagggga | ccgtcccccg | gtaatgcag | atgggaccca | ggcttccccc | 780 |
| ggattccctc | atggggatcg | aggggagag | ctggcactcc | cttagccatc | cgagtggacg | 840 |
| tctgtcctcc | ttcggatgcc | caggtcggac | cacggggagg | tggagatgcc | atgccgaccc | 900 |
| gaagaggaaa | gaaggagacc | ggacgcaaac | ctgtgagtgg | aactctcdtc | ctttattggg | 960 |
| gggtacactc | gaggagtgga | aggcggggag | ggggggggcgg | tctttgtccc | tatggaaatt | 1020 |
| gctggtctcc | cctgatgtcc | agtccatccc | cgtgtctggt | gaatggagac | tccggaacac | 1080 |
| ctagcatcct | agggacaaat | ccgccccgg | gcgctcccct | cggacttcct | ccgggagggt | 1140 |
| tcacaccccc | atcctgcggg | ccggccgctc | ttctttctct | tttctcgtct | tcaacgatca | 1200 |
| acctcctgag | ttccccttct | tcctcctcgc | tgagcttctt | ccctccggag | gacagttgct | 1260 |
| tcttcttgtt | ctcgagggcc | ttccttcttc | ggtgatccct | cctctcctcg | tcggtgaatc | 1320 |
| ctcccttgcg | actcttcttc | cccggaccgg | agtcgacctc | catctgatct | gttcgggctc | 1380 |
| tcttcgctgg | gggagctccc | tcccctgcct | tcccctttct | tattattccg | aggatgttcc | 1440 |
| ccagccaggg | attttcatcc | tcgagtctct | tgatgttcct | cctcgtcttc | cggatcctct | 1500 |
| tttcgaggtc | ttccagatct | tttcttgctt | cgacccactt | tgagaggaca | tcctcccgtc | 1560 |
| ctccccttcg | ttctctcttc | gcatcggact | ggctcatctc | ggcgagggcg | gcgatcctca | 1620 |
| gtgctcttac | tctttacagt | agaaagagga | gactgctgga | tgccccgccc | gggcycgagc | 1680 |

<210> SEQ ID NO 27
<211> LENGTH: 645
<212> TYPE: DNA
<213> ORGANISM: hepatitis D virus
<220> FEATURE:
<221> NAME/KEY: CDS
<222> LOCATION: (1)..(645)
<223> OTHER INFORMATION: cDNA of LHD

<400> SEQUENCE: 27

```
atg agc cag tcc gat gcg aag aga gaa cga agg gga gga cgg gag gat        48
Met Ser Gln Ser Asp Ala Lys Arg Glu Arg Arg Gly Gly Arg Glu Asp
1               5                   10                  15 gtc ctc tca aag tgg gtc gaa gca aga aaa gat ctg gaa gac ctc gaa        96
```

-continued

```
Val Leu Ser Lys Trp Val Glu Ala Arg Lys Asp Leu Glu Asp Leu Glu
         20                  25                  30 aag agg atc cgg aag acg agg agg aac atc aag aga ctc gag gat gaa      144
Lys Arg Ile Arg Lys Thr Arg Arg Asn Ile Lys Arg Leu Glu Asp Glu
         35                  40                  45 aat ccc tgg ctg ggg aac atc ctc gga ata ata aga aag ggg aag gca      192
Asn Pro Trp Leu Gly Asn Ile Leu Gly Ile Ile Arg Lys Gly Lys Ala
 50                  55                  60 ggg gag gga gct ccc cca gcg aag aga gcc cga aca gat cag atg gag      240
Gly Glu Gly Ala Pro Pro Ala Lys Arg Ala Arg Thr Asp Gln Met Glu
 65                  70                  75                  80 gtc gac tcc ggt ccg ggg aag aag agt cgc aag gga gga ttc acc gac      288
Val Asp Ser Gly Pro Gly Lys Lys Ser Arg Lys Gly Gly Phe Thr Asp
                 85                  90                  95 gag gag agg agg gat cac cga aga agg aag gcc ctc gag aac aag aag      336
Glu Glu Arg Arg Asp His Arg Arg Arg Lys Ala Leu Glu Asn Lys Lys
                 100                 105                 110 aag caa ctg tcc tcc gga ggg aag aag ctc agc gag gag gaa gaa ggg      384
Lys Gln Leu Ser Ser Gly Gly Lys Lys Leu Ser Glu Glu Glu Glu Gly
         115                 120                 125 gaa ctc agg agg ttg atc gtt gaa gac gag aaa aga gaa aga aga gcg      432
Glu Leu Arg Arg Leu Ile Val Glu Asp Glu Lys Arg Glu Arg Arg Ala
 130                 135                 140 gcc ggc ccg cag gat ggg ggt gtg aac cct ccc gga gga agt ccg agg      480
Ala Gly Pro Gln Asp Gly Gly Val Asn Pro Pro Gly Gly Ser Pro Arg
145                 150                 155                 160 gga gcg ccc ggg ggc gga ttt gtc cct agg atg cta ggt gtt ccg gag      528
Gly Ala Pro Gly Gly Gly Phe Val Pro Arg Met Leu Gly Val Pro Glu
                 165                 170                 175 tct cca ttc acc aga cac ggg gat gga ctg gac atc agg gga gac cag      576
Ser Pro Phe Thr Arg His Gly Asp Gly Leu Asp Ile Arg Gly Asp Gln
                 180                 185                 190 caa ttt cca tgg gga caa aga ccg ccc ccc cct ccc cgc ctt cca ctc      624
Gln Phe Pro Trp Gly Gln Arg Pro Pro Pro Pro Arg Leu Pro Leu
         195                 200                 205 ctc gag tgt acc ccc caa taa                                          645
Leu Glu Cys Thr Pro Gln
         210
```

<210> SEQ ID NO 28
<211> LENGTH: 214
<212> TYPE: PRT
<213> ORGANISM: hepatitis D virus

<400> SEQUENCE: 28

```
Met Ser Gln Ser Asp Ala Lys Arg Glu Arg Arg Gly Gly Arg Glu Asp
 1               5                  10                  15

Val Leu Ser Lys Trp Val Glu Ala Arg Lys Asp Leu Glu Asp Leu Glu
         20                  25                  30

Lys Arg Ile Arg Lys Thr Arg Arg Asn Ile Lys Arg Leu Glu Asp Glu
         35                  40                  45

Asn Pro Trp Leu Gly Asn Ile Leu Gly Ile Ile Arg Lys Gly Lys Ala
 50                  55                  60

Gly Glu Gly Ala Pro Pro Ala Lys Arg Ala Arg Thr Asp Gln Met Glu
 65                  70                  75                  80

Val Asp Ser Gly Pro Gly Lys Lys Ser Arg Lys Gly Gly Phe Thr Asp
                 85                  90                  95

Glu Glu Arg Arg Asp His Arg Arg Arg Lys Ala Leu Glu Asn Lys Lys
                 100                 105                 110
```

```
              Lys Gln Leu Ser Ser Gly Gly Lys Lys Leu Ser Glu Glu Glu Gly
                          115                 120                 125

Glu Leu Arg Arg Leu Ile Val Glu Asp Glu Lys Arg Glu Arg Arg Ala
                      130                 135                 140

Ala Gly Pro Gln Asp Gly Gly Val Asn Pro Pro Gly Gly Ser Pro Arg
              145                 150                 155                 160

Gly Ala Pro Gly Gly Gly Phe Val Pro Arg Met Leu Gly Val Pro Glu
                              165                 170                 175

Ser Pro Phe Thr Arg His Gly Asp Gly Leu Asp Ile Arg Gly Asp Gln
                          180                 185                 190

Gln Phe Pro Trp Gly Gln Arg Pro Pro Pro Pro Arg Leu Pro Leu
                      195                 200                 205

Leu Glu Cys Thr Pro Gln
                  210

<210> SEQ ID NO 29
<211> LENGTH: 588
<212> TYPE: DNA
<213> ORGANISM: hepatitis D virus
<220> FEATURE:
<221> NAME/KEY: CDS
<222> LOCATION: (1)..(588)
<223> OTHER INFORMATION: cDNA of sHD

<400> SEQUENCE: 29 atg agc cag tcc gat gcg aag aga gaa cga agg gga gga cgg gag gat        48
Met Ser Gln Ser Asp Ala Lys Arg Glu Arg Arg Gly Gly Arg Glu Asp
1               5                   10                  15 gtc ctc tca aag tgg gtc gaa gca aga aaa gat ctg gaa gac ctc gaa        96
Val Leu Ser Lys Trp Val Glu Ala Arg Lys Asp Leu Glu Asp Leu Glu
                20                  25                  30 aag agg atc cgg aag acg agg agg aac atc aag aga ctc gag gat gaa       144
Lys Arg Ile Arg Lys Thr Arg Arg Asn Ile Lys Arg Leu Glu Asp Glu
            35                  40                  45 aat ccc tgg ctg ggg aac atc ctc gga ata ata aga aag ggg aag gca       192
Asn Pro Trp Leu Gly Asn Ile Leu Gly Ile Ile Arg Lys Gly Lys Ala
        50                  55                  60 ggg gag gga gct ccc cca gcg aag aga gcc cga aca gat cag atg gag       240
Gly Glu Gly Ala Pro Pro Ala Lys Arg Ala Arg Thr Asp Gln Met Glu
65                  70                  75                  80 gtc gac tcc ggt ccg ggg aag aag agt cgc aag gga gga ttc acc gac       288
Val Asp Ser Gly Pro Gly Lys Lys Ser Arg Lys Gly Gly Phe Thr Asp
                85                  90                  95 gag gag agg agg gat cac cga aga agg aag gcc ctc gag aac aag aag       336
Glu Glu Arg Arg Asp His Arg Arg Arg Lys Ala Leu Glu Asn Lys Lys
            100                 105                 110 aag caa ctg tcc tcc gga ggg aag aag ctc agc gag gag gaa gaa ggg       384
Lys Gln Leu Ser Ser Gly Gly Lys Lys Leu Ser Glu Glu Glu Glu Gly
        115                 120                 125 gaa ctc agg agg ttg atc gtt gaa gac gag aaa aga gaa aga aga gcg       432
Glu Leu Arg Arg Leu Ile Val Glu Asp Glu Lys Arg Glu Arg Arg Ala
                130                 135                 140 gcc ggc ccg cag gat ggg ggt gtg aac cct ccc gga gga agt ccg agg       480
Ala Gly Pro Gln Asp Gly Gly Val Asn Pro Pro Gly Gly Ser Pro Arg
145                 150                 155                 160 gga gcg ccc ggg ggc gga ttt gtc cct agg atg cta ggt gtt ccg gag       528
Gly Ala Pro Gly Gly Gly Phe Val Pro Arg Met Leu Gly Val Pro Glu
                165                 170                 175 tct cca ttc acc aga cac ggg gat gga ctg gac atc agg gga gac cag       576
```

```
Ser Pro Phe Thr Arg His Gly Asp Gly Leu Asp Ile Arg Gly Asp Gln
            180                 185                 190 caa ttt cca tag                                                        588
Gln Phe Pro
    195

<210> SEQ ID NO 30
<211> LENGTH: 195
<212> TYPE: PRT
<213> ORGANISM: hepatitis D virus

<400> SEQUENCE: 30

Met Ser Gln Ser Asp Ala Lys Arg Glu Arg Gly Gly Arg Glu Asp
1               5                   10                  15

Val Leu Ser Lys Trp Val Glu Ala Arg Lys Asp Leu Glu Asp Leu Glu
            20                  25                  30

Lys Arg Ile Arg Lys Thr Arg Arg Asn Ile Lys Arg Leu Glu Asp Glu
        35                  40                  45

Asn Pro Trp Leu Gly Asn Ile Leu Gly Ile Ile Arg Lys Gly Lys Ala
    50                  55                  60

Gly Glu Gly Ala Pro Pro Ala Lys Arg Ala Arg Thr Asp Gln Met Glu
65                  70                  75                  80

Val Asp Ser Gly Pro Gly Lys Lys Ser Arg Lys Gly Gly Phe Thr Asp
                85                  90                  95

Glu Glu Arg Arg Asp His Arg Arg Arg Lys Ala Leu Glu Asn Lys Lys
            100                 105                 110

Lys Gln Leu Ser Ser Gly Gly Lys Lys Leu Ser Glu Glu Glu Glu Gly
        115                 120                 125

Glu Leu Arg Arg Leu Ile Val Glu Asp Glu Lys Arg Glu Arg Arg Ala
    130                 135                 140

Ala Gly Pro Gln Asp Gly Gly Val Asn Pro Pro Gly Gly Ser Pro Arg
145                 150                 155                 160

Gly Ala Pro Gly Gly Gly Phe Val Pro Arg Met Leu Gly Val Pro Glu
                165                 170                 175

Ser Pro Phe Thr Arg His Gly Asp Gly Leu Asp Ile Arg Gly Asp Gln
            180                 185                 190

Gln Phe Pro
    195

<210> SEQ ID NO 31
<211> LENGTH: 25
<212> TYPE: DNA
<213> ORGANISM: hepatitis D virus

<400> SEQUENCE: 31
gaggaaagaa ggacgcgaga cgcaa                                             25

<210> SEQ ID NO 32
<211> LENGTH: 21
<212> TYPE: DNA
<213> ORGANISM: hepatitis D virus

<400> SEQUENCE: 32 acccccctcga aggtggatcg a                                                21

<210> SEQ ID NO 33
<211> LENGTH: 22
<212> TYPE: DNA
<213> ORGANISM: hepatitis D virus
```

```
<400> SEQUENCE: 33
catgccgacc cgaagaggaa ag                                          22

<210> SEQ ID NO 34
<211> LENGTH: 24
<212> TYPE: DNA
<213> ORGANISM: hepatitis D virus

<400> SEQUENCE: 34
gaaggaaggc cctcgagaac aaga                                        24

<210> SEQ ID NO 35
<211> LENGTH: 24
<212> TYPE: DNA
<213> ORGANISM: hepatitis D virus

<400> SEQUENCE: 35
ctccagagga ccccttcagc gaac                                        24

<210> SEQ ID NO 36
<211> LENGTH: 24
<212> TYPE: DNA
<213> ORGANISM: hepatitis D virus

<400> SEQUENCE: 36
cccgcgggtt ggggatgtga accc                                        24

<210> SEQ ID NO 37
<211> LENGTH: 23
<212> TYPE: DNA
<213> ORGANISM: hepatitis D virus

<400> SEQUENCE: 37
gtacactcga ggagtggaag gcg                                         23

<210> SEQ ID NO 38
<211> LENGTH: 21
<212> TYPE: DNA
<213> ORGANISM: hepatitis D virus

<400> SEQUENCE: 38
tctgttcgct gaagggtcc t                                            21

<210> SEQ ID NO 39
<211> LENGTH: 22
<212> TYPE: DNA
<213> ORGANISM: hepatitis D virus

<400> SEQUENCE: 39
ccagaggacc ccttcagcga ac                                          22

<210> SEQ ID NO 40
<211> LENGTH: 20
<212> TYPE: DNA
<213> ORGANISM: hepatitis D virus

<400> SEQUENCE: 40
aacaccctcc tgctagcccc                                             20

<210> SEQ ID NO 41
<211> LENGTH: 22
<212> TYPE: DNA
```

```
<213> ORGANISM: hepatitis D virus

<400> SEQUENCE: 41
ccggagttcc tcttcctcct cc                                              22

<210> SEQ ID NO 42
<211> LENGTH: 23
<212> TYPE: DNA
<213> ORGANISM: hepatitis D virus

<400> SEQUENCE: 42
gttcgcgtcc gagtccttct ttc                                             23

<210> SEQ ID NO 43
<211> LENGTH: 20
<212> TYPE: DNA
<213> ORGANISM: hepatitis D virus

<400> SEQUENCE: 43
gagctttctt cgattcggac                                                 20

<210> SEQ ID NO 44
<211> LENGTH: 20
<212> TYPE: DNA
<213> ORGANISM: hepatitis D virus

<400> SEQUENCE: 44
gactggtccc ctcatgttcc                                                 20

<210> SEQ ID NO 45
<211> LENGTH: 22
<212> TYPE: DNA
<213> ORGANISM: hepatitis D virus

<400> SEQUENCE: 45
gttcgctgaa ggggtcctct gg                                              22

<210> SEQ ID NO 46
<211> LENGTH: 24
<212> TYPE: DNA
<213> ORGANISM: hepatitis D virus

<400> SEQUENCE: 46
tcatcctcga gtctcttgat ggtc                                            24

<210> SEQ ID NO 47
<211> LENGTH: 20
<212> TYPE: DNA
<213> ORGANISM: hepatitis D virus

<400> SEQUENCE: 47
aacatccact cgctagcccc                                                 20

<210> SEQ ID NO 48
<211> LENGTH: 396
<212> TYPE: DNA
<213> ORGANISM: hepatitis D virus

<400> SEQUENCE: 48
catgccgacc cgaagaggaa agaaggattc ggacgcaaac ctgtgagtgg aagttcgctc      60
tttattgggg ggtacactcg aggagtggaa ggcggggagg gggggtcgga ctaggtccct     120
atggaaactg tcggtctcct cggatgtcga gtccctctcc cgttctggag aagggggact     180
```

-continued

```
ccgggacacc tagcagttga ggaacgaagc cgcccccggg cgctcccctc ggtggtccct    240
cgggagggtt cacatcccca acccgcgggc cggctattct tcttgctctt tgctcgtcat    300
cggcggtcaa cttcctgagt tcctcttctt cctccttgct gagggacttt cctcctgcgg    360
acagctgctt cttcttgttc tcgagggcct ccttc                               396
```

<210> SEQ ID NO 49
<211> LENGTH: 397
<212> TYPE: DNA
<213> ORGANISM: hepatitis D virus

<400> SEQUENCE: 49

```
catgccgacc cgaagaggaa agaaggactc ggacgcgaac tcgtgagtgg aaacttattc    60
ctttactggg gagtacactc gaggagtgga aggcggggag gccgggtcc  cgggyytacc    120 cacgggtact gctggttccc cctcacgtcc agtccctccc ccgtcctgga aagggagac    180 tcrggaacac ctagcatttg agggacaaag ccgcccccgg gcgctcccct cggagatgtt    240
ccgggtgggt tcacatcccc aacccgcggg ccggctactc ttctttctct tctctcgtct    300
tcctcggtca acttccggag ttcctcttcc tcctccttgc tragtgactt cctcccgcg    360 ctcagttgtt tcttcttgtt ctcgagggcc ttccttc                             397
```

<210> SEQ ID NO 50
<211> LENGTH: 397
<212> TYPE: DNA
<213> ORGANISM: hepatitis D virus

<400> SEQUENCE: 50

```
catgccgacc cgaagaggaa agaaggactc ggacgcgaac ccgtgagtgg aaacctcgtt    60
ctttattggg gagtacactc gaggagtgga aggcggggag ggcggggagg agtgttaccc    120
yacgggaact gctgagtgcc cctgacgtcc agaccctccc ccgtccggga aatggagat    180 tcgggaacgt gaagcatggt ggggacgaag ccccctccgg gcgctcccct cggatctccg    240
ccgggtgggt tcacatcccc aacccgcggg ccggctgttc ttcttttcct ttgctcgtct    300
tccccggtca gcctcccgag ttcctcttct tctccctgc tgaggttctt ccctccggcg    360
gccagttgct tcttcttgtt ctcgagggcc ttccttc                             397
```

<210> SEQ ID NO 51
<211> LENGTH: 410
<212> TYPE: DNA
<213> ORGANISM: hepatitis D virus

<400> SEQUENCE: 51

```
aygccatgcc gacccgaaga aggaaagaag gactcggacg cgaacccgtg agtggaactc    60
tttatctttt actggggagt acactcgagg agtggaaggc ggggaggccg ggtcccggg    120 tctacccacg ggaattgctg gtttcccctt acgtccagtc cacttccccgt cctggagaag   180 ggagactcgg gaacatctag catttgaggg acaaagccgc cccgggcgc tcccctcgga    240 ggtccctcgg gtgggttcac atccccaacc cgcgggccgg ctactcttct ttcccttctc    300
tcgtcttcct cggtcaactt ccggagttcc tcttcctcct cctgctgag tgactttccc    360 cccgcgctca gctgattctt cttgttctcg agggcttttcc ttcttcggtg              410
```

<210> SEQ ID NO 52
<211> LENGTH: 397
<212> TYPE: DNA

```
<213> ORGANISM: hepatitis D virus

<400> SEQUENCE: 52
catgccgacc cgaagaggaa agaaggactc ggacgcgaac ccgtgagtgg aaccttattc      60
ctttattggg gagtacactc gaggagtgga aggcggggag acggggctcc cgggcttacc     120
yacgggaact gctggttccc ccttatgtcc agtccctctc ccgtcctggt gaaggragac     180
tcgggaacgt tcagcatttg agggacaaag ccgcccccgg gcgctcccct cggaggtccc     240
tgtggtgggt tcacatcccc aacccgcggg ccggctactc ttctttccct tctctcgtct     300
tcytcggtca acctcccgag ttcctcttct tcctccttgc tgagtgactt tccycccgcg     360
ttcagctgtt tcttcttgtt ctcgagggcc ttccttc                              397

<210> SEQ ID NO 53
<211> LENGTH: 399
<212> TYPE: DNA
<213> ORGANISM: hepatitis D virus

<400> SEQUENCE: 53
catgccgacc cgaagaagga aagaaggact cggacgcgaa cccgtgagtg gaactcttta      60
tcttttactg gggagtacac tcgaggagtg aaggcgggg aggccggggt cccgggtcta     120
cccacgggaa ttgctggttt ccccttacgt ccagtccact tcccgtcctg agaagggag     180
actcgggaac atctagcatt tgagggacaa agccgccccc gggcgctccc ctcggaggtc     240
cctcgggtgg gttcacatcc ccaacccgcg ggccggctac tcttctttcc cttctctcgt     300
cttcctcggt caacttccgg agttcctctt cctcctccct gctgagtgac tttccccccg     360
cgctcagctg attcttcttg ttctcgaggg cttttccttc                            399

<210> SEQ ID NO 54
<211> LENGTH: 397
<212> TYPE: DNA
<213> ORGANISM: hepatitis D virus

<400> SEQUENCE: 54
catgccgacc cgaagaggaa agaaggattc ggacgcaaac ctgtgagtgg aaattctctt      60
ctttattggg gagtacactc gaggagtgga aggcggggag gggggtcgg actaggaacc     120
tatgggaact gctggtttcc tcggatgtcc agtccatccc ccgtcctgga gaatggtgac     180
tccgggactc ctagcagttg aggaacgaag ccgcccccgg gcgctcccct cgaaggcgcg     240
gggggagggt tcacatcccc aacccgcggg ccggctgttc ttcttgctct tttctcgtcc     300
tcgacggtca gcctcgcgag ttcctcttct tcttccttgc cgaggttctt tcctcccgcg     360
gagagttgct tcctccttgtt ctcgagggcc ttccttc                             397

<210> SEQ ID NO 55
<211> LENGTH: 397
<212> TYPE: DNA
<213> ORGANISM: hepatitis D virus

<400> SEQUENCE: 55
catgccgacc cgaagaggaa agaaggactc ggacgcgaac tcgtgagtgg aaccttaatc      60
ctttattggg gagtacactc gaggagtgga aggcggggag gccggggtcc cgagcttacc     120
tacgggaact gctggtttcc tcttatgtcc agtccctctc ccgtcctaga aagggagac     180
tcgggaacgc ccagcatttg agggacaaag ccgcccccgg gcgctcccct cggaggttcc     240
tcgggwgggt tcacatcccc aacccgcggg ccggctactc ttctttccct tctctcgtct     300
```
tcctcggtca acttccggag ttcctcttcc tcctccctgc tgaggttctt tcctcccgcg    360
gagagttgct tcctcttgtt ctcgagggcc ttccttc                             397

<210> SEQ ID NO 56
<211> LENGTH: 397
<212> TYPE: DNA
<213> ORGANISM: hepatitis D virus

<400> SEQUENCE: 56
catgccgacc cgaagaggaa agaaggactc ggacgcgaac tcgtgagtgg acacctcgtt    60
ctttattggg gagtacactc gaggagtgga aggcggggag ggcggggagg agtgttaccc    120
tatggaaact gctggttwcc cctcacgtcc agaccttctc ccgtccggga gaatggagat    180
tcgggaacga gatgcatggt tgggacgaag cccctccgg gcgctcccct cggacttccc    240
tcgggtgggt tcacatcccc aaccgcgggg ccggctattc ttcttttcct ttgctcgtca    300
tccctggtca gcctcaggag ttcctcttct tcttccttgc tgaggttctt tcctcccgcg    360
gagagttgct tcctcttgtt ctcgagggcc ttccttc                             397

<210> SEQ ID NO 57
<211> LENGTH: 396
<212> TYPE: DNA
<213> ORGANISM: hepatitis D virus

<400> SEQUENCE: 57
catgccgacc cgaagaggaa agaaggattc ggacgcaaac ctgtgagtgg aagctttctc    60
tttattgggg ggtacactcg aggagtggaa ggcggggagg ggggtcgga ctaggtcccy    120 atggaaactg ccggtttcct cggacgtcga gtccctctcc cgttctggag aaggggact    180 ccgggactcc tagcagttga ggaacgaagc cgccccggg cgctcccctc ggtggtccct    240
cgggagggtt cacatcccca acctgcgggc cggctactct tcttgctctt tgctcgtctt    300
cgacggtcaa cctctcgagt tcctcttcct cctccttgct gaggttcttt cctcccgcgg    360
agagttgctt cctcttgttc tcgagggcct tccttc                              396

<210> SEQ ID NO 58
<211> LENGTH: 398
<212> TYPE: DNA
<213> ORGANISM: hepatitis D virus

<400> SEQUENCE: 58
catgccgacc cgaagaggaa agaaggagac cggacgcaaa cctgtgagtg gaactctcdt    60
cctttattgg gggtacact cgaggagtgg aaggcgggga ggggggggcg gtctttgtcc    120
ctatggaaat tgctggtctc ccctgatgtc cagtccatcc ccgtgtctgg tgaatggaga    180
ctccggaaca cctagcatcc tagggacaaa tccgccccg ggcgctcccc tcggacttcc    240
tccgggaggg ttcacacccc catcctgcgg gccggccgct cttctttctc ttttctcgtc    300
ttcaacgatc aacctcctga gttccccttc ttcctcctcg ctgagcttct tccctccgga    360
ggacagttgc ttcttcttgt tctcgagggc cttccttc                            398

<210> SEQ ID NO 59
<211> LENGTH: 10
<212> TYPE: PRT
<213> ORGANISM: hepatitis D virus

<400> SEQUENCE: 59

-continued

Arg Leu Pro Leu Leu Glu Cys Thr Pro Gln
1               5                   10

<210> SEQ ID NO 60
<211> LENGTH: 9
<212> TYPE: PRT
<213> ORGANISM: hepatitis D virus

<400> SEQUENCE: 60

Trp Gly Pro Ser Pro Thr Pro Pro Pro
1               5

<210> SEQ ID NO 61
<211> LENGTH: 9
<212> TYPE: PRT
<213> ORGANISM: hepatitis D virus
<220> FEATURE:
<221> NAME/KEY: misc_feature
<222> LOCATION: (3)..(3)
<223> OTHER INFORMATION: Xaa is any amino acid

<400> SEQUENCE: 61

Trp Val Xaa Pro Gly Pro Arg Pro Pro
1               5

<210> SEQ ID NO 62
<211> LENGTH: 9
<212> TYPE: PRT
<213> ORGANISM: hepatitis D virus

<400> SEQUENCE: 62

Trp Val Ser Pro Gly Ala Pro Ser Pro
1               5

<210> SEQ ID NO 63
<211> LENGTH: 9
<212> TYPE: PRT
<213> ORGANISM: hepatitis D virus

<400> SEQUENCE: 63

Trp Val Asp Pro Gly Pro Arg Pro Pro
1               5

<210> SEQ ID NO 64
<211> LENGTH: 9
<212> TYPE: PRT
<213> ORGANISM: hepatitis D virus

<400> SEQUENCE: 64

Trp Gly Asn Thr Pro Pro Arg Pro Pro
1               5

<210> SEQ ID NO 65
<211> LENGTH: 9
<212> TYPE: PRT
<213> ORGANISM: hepatitis D virus

<400> SEQUENCE: 65

Trp Gly Gln Arg Pro Pro Pro Pro Pro
1               5

<210> SEQ ID NO 66
<211> LENGTH: 1685
<212> TYPE: DNA
<213> ORGANISM: hepatitis D virus
<220> FEATURE:

<210> SEQ ID NO 66
<211> LENGTH: 1685
<212> TYPE: DNA
<213> ORGANISM: hepatitis D virus
<220> FEATURE:
<221> NAME/KEY: source
<222> LOCATION: (1)..(1685)
<223> OTHER INFORMATION: complete genomic sequence of Pt26

<400> SEQUENCE: 66

```
atgggccgca taccgagcga aggataccgg taagggggaga ggaggaatcc cgaggggatc      60
gcccactaaa gagtagagga attctcggaa agctctccca agaagaacca gaatccctca     120
agagagagga gaatccccat gacgctgaaa gagacttccg ggtaaccaag tcaaggagaa     180
ggaacggtag aaaagagcga gcctctcgat acgaaagggc cgcgagccta tcgagtttgg     240
agtcatccgg gccgaagggt tgagacgcac ccacagacgg gagcctccag gagggtttga     300
ggagaactca cctccagagg accccttcag cgaacagagg agtctctacc tcggaggaga     360
aagaccgtag cgatgggga gatgctagga gtaggcggcg accgaagcga ggaggaaagc     420
aaagaaagcc acggggctag cgagtggatg ttccgcccca aggggagccg agtgaggctt     480
atcccgggga actcggtaat tcgccccgaa atgaggactc cggggtcccc ttccgaagga     540
acggagggg gtgactagga atcaggatcc agtggatccg tgggaattat cccgttccac     600
ccccgcggca cactccttcc ccctgcggg cccccccata agatggcagg aacccactca     660
ttggggtccg ctgttccatt cttttcttac cttgtggccgg catggtccca gcctcctcgc     720
tggcgccggc tgggcaacat tccgaggggga ccgtccctcg gtaatggcga atgggaccca     780
gaactctctc tagattccca gagagaatcg agagaaaact ggctctccct tagccatccg     840
agtaggacgt ctgtcctcct acggatgccc aggtcggacc gcggggaggt ggagatgcca     900
tgccgacccg aagaggaaag aagaacacgg acgcgaaccc gtaagtggaa ccctgatcct     960
ttattggggg gtacactcga ggagtggaag gcgctgcccg ggggggaaccg gatttaccta    1020
cgggaatccc tgggttcctc tgatgtccag tccctctccc gtccgagtga agggagactc    1080
cggaactcca gtcatttgag ggacgaatcc gcccccgggc gctcccctcg gacttcctcc    1140
aggagggttc acatccccaa cccgcgggcc ggctactctt ctttcccttc tctcgtcttc    1200
ctcggtcaac ctcctgagtt cctcttcttc ctccctgctg aggttctttc ctcccgcgga    1260
gagttgcttc ctcttgttct cgagggcctt ccttctgcgg tgatcctccc tctccttgtc    1320
ggtgaacccg ctcttgtgag gcctcttcat aggtccggag tcgacctcca tctgatctgt    1380
tcgggccctc ttcgccgggg gagctccctc cccgtccttc ccttttctta tgattcccag    1440
gatgttcccc agccagggat tttcatcctc gagtctcttg atggtctttc tggccttccg    1500
gaggtctctc tcgagctcct ctgcctttct tcttgtggaa atccacttt cgaggatttc    1560
ttccccttcct ccccctccggc ccttcctcga ctcgggttgg ctcatcctcg gcgagggcga    1620
cggtcctcag ttctctctat tcttttcttga aagaggagac tgctggacca aacgcccgag    1680
ccggg                                                                1685
```

<210> SEQ ID NO 67
<211> LENGTH: 1688
<212> TYPE: DNA
<213> ORGANISM: hepatitis D virus
<220> FEATURE:
<221> NAME/KEY: source
<222> LOCATION: (1)..(1688)
<223> OTHER INFORMATION: complete genomic sequence of Pt62

<400> SEQUENCE: 67

```
atgggccgca agccgaacga aggattccgg taagggggaga ggaagaatcc cgaagggggtt      60
ccccactaaa gagtggaaga attctcggga agcttctccc aagaagaacc agaatccccc     120
```

```
aagagagaga atggatcccc atgacgctgg aagagactcc gggtaaccaa gtcaaggaga      180
aggaacggta gaaaagagcg agcctctcga tacgaaaggg ccgcgaccta tcaagtttgg      240
agtcatccgg gccaaagggt tgaaaaatcc cacagacggg agccaccagg agggatctag      300
gagaatccac ctccagagga ccccccctcaa tgaacagaag actctctacc tcggaggaaa     360
aagaccatag cgataggaag agatgctagg agtaggcggc gaccaaagcg aggaagaaag      420
taaagaaagc aacggggcta gcgagtggat gttccgcccc aaggggagcc gagtgaggct      480
tatcccgggg aactcggcgt atcgtcccga aatgaggagc ccggatcccc ttccaaaaag      540
acggagaggg ggtgactagg aatcgggctc cggtggatcc gtgggaccag cccgctccac      600
ctccgcggca cactccttcc ccctgcggg ccccccata agatggcagg aacccactca       660
ttggggtccg ctgttccatt ctttcttacc ttgtggccgg catggtccca gcctcctcgc      720
tggcgccggc tgggcaacat tccgagggga ccgtccctcg gtaatggcga atgggaccca     780
gaactctctc tagattccca gagagaatcg agagaaaact ggctctcccct tagccatccg    840 agtaggacgt ctgtcctcct acggatgccc aggtcggacc gcgaggaggt ggagatgcca     900
tgccgacccg aagaggaaag aagaacacgg acgcgaaccc gtaagtggaa ccctgatcct     960
ttattggggg gtacactcga ggagtggaag gcgctgcccg gggggagccg gattgaccta     1020
cgggaatccc cggtcgcctc tgatgtccag tccctccccc gtccgagaga agggagattc     1080
cggaactcca gtcatttgag ggacgaagcc gcccccgggc gctcccctcg gacttcctcc     1140
aggagggttc acatccccaa cccgcgggcc ggctactctt ctttgtcttt cgtcgtcttc     1200
aatggtcaac ctcctgagtt cctcttcttc ttccttgctg aggctctttc ccccgcgga      1260 gagttggttc ttcttgttct ggagggcctt ccttctgcgg tggtcctgcc tctccttgtc     1320
ggtgaacccg ctcttgtgag gtttcttcct aggtccggag tcgacctcca tctgatctgt    1380
tcgggccctc ttcgccgggg gagctccctc cccgtccttc cctttcctta tgattcccag     1440
gatgttcccc agccagggat tgtcatcctc gagtctcttg atggtctttc tggccttccg     1500
gaggtctctc tcgagctctt ccgccttttt tcttgtggat acccactttt cgaggatatc     1560
ttcccttcct ccccctccgg cttttcctcga ttcggattgg ctcatcctcg acgagggcga    1620
cggtcctcag ttctctctat tctttccttt tgaaagagga gactgctggt ccaaacgccc     1680
gagtcggg                                                              1688
```

<210> SEQ ID NO 68
<211> LENGTH: 214
<212> TYPE: PRT
<213> ORGANISM: Hepatitis D virus

<400> SEQUENCE: 68

```
Met Ser Gln Pro Asp Ser Arg Arg Pro Arg Gly Arg Glu Glu Gln
1               5                   10                  15

Leu Gly Lys Trp Ile Asp Ala Arg Arg Arg Lys Glu Glu Leu Glu Arg
                20                  25                  30

Asp Leu Arg Lys Val Asn Lys Thr Ile Lys Arg Leu Glu Glu Asp Asn
            35                  40                  45

Pro Trp Leu Gly Asn Val Arg Gly Ile Ile Arg Lys Asp Lys Asp Gly
        50                  55                  60

Glu Gly Ala Pro Pro Ala Lys Arg Ala Arg Thr Asp Gln Met Glu Val
65                  70                  75                  80

Asp Ser Gly Pro Arg Lys Arg Lys His Pro Gly Gly Phe Thr Glu Gln
```

-continued

Glu Arg Arg Asp His Arg Arg Lys Ala Leu Glu Asn Lys Lys
            85                  90                  95
            100                 105                 110

Gln Leu Ser Ser Gly Gly Lys Asn Leu Ser Arg Glu Glu Glu Glu
            115                 120                 125

Leu Arg Arg Leu Thr Glu Glu Asp Glu Arg Arg Glu Arg Val Ala
            130                 135             140

Gly Pro Arg Val Gly Asp Val Asn Pro Leu Asp Gly Pro Arg Gly
145             150                 155                 160

Ala Pro Gly Gly Gly Phe Val Pro Ser Met His Asp Ile Pro Glu Ser
                165                 170                 175

Pro Phe Thr Arg Arg Gly Asp Gly Leu Asp Val Arg Ala Gly Ala Gln
            180                 185                 190

Glu Phe Pro Glx Val Ser Pro Gln Pro Pro Pro Arg Leu Pro Leu
            195                 200                 205

Leu Glu Cys Thr Pro Gln
            210

<210> SEQ ID NO 69
<211> LENGTH: 214
<212> TYPE: PRT
<213> ORGANISM: Hepatitis D virus

<400> SEQUENCE: 69

Met Ser Gln Ser Asp Ala Arg Arg Val Arg Arg Gly Arg Glu Glu Thr
1               5                   10                  15

Leu Gly Lys Trp Ile Asp Gly Arg Arg Lys Glu Glu Leu Glu Lys
            20                  25                  30

Glu Leu Arg Lys Ile Asn Lys Asn Leu Lys Arg Leu Glu Glu Asp Asn
            35                  40                  45

Pro Trp Leu Gly Asn Ile Arg Gly Ile Ile Arg Lys Asp Lys Asp Gly
        50                  55                  60

Glu Gly Ala Pro Pro Ala Lys Arg Ala Arg Thr Asp Gln Met Glu Val
65                  70                  75                  80

Asp Ser Gly Pro Arg Lys Arg His Pro Gly Gly Phe Thr Glu Gln
            85                  90                  95

Glu Arg Arg Asp His Arg Arg Lys Ala Leu Glu Asn Lys Lys
            100                 105                 110

Gln Leu Ser Ser Gly Gly Lys Val Leu Ser Arg Glu Glu Glu Glu
            115                 120                 125

Leu Arg Lys Leu Thr Glu Glu Asp Glu Arg Arg Glu Arg Val Ala
            130                 135             140

Gly Pro Arg Val Gly Asp Val Asn Pro Leu Glu Gly Ala Pro Arg Gly
145             150                 155                 160

Ala Pro Gly Gly Gly Phe Val Pro Thr Met Glu Gly Val Pro Glu Ser
                165                 170                 175

Pro Phe Ser Arg Arg Gly Asp Gly Leu Asp Ile Arg Ala Gly Thr Gln
            180                 185                 190

Gly Phe Pro Glx Val Asp Pro Gly Arg Pro Ser Pro Arg Leu Pro Leu
            195                 200                 205

Leu Glu Cys Thr Pro Gln
            210

<210> SEQ ID NO 70
<211> LENGTH: 215

```
<212> TYPE: PRT
<213> ORGANISM: Hepatitis D virus

<400> SEQUENCE: 70

Met Ser Gln Ser Glu Ser Arg Lys Ser Arg Gly Thr Arg Glu Glu
1               5                   10                  15

Thr Leu Glu Arg Trp Ile Ile Ile Arg Arg Lys Ala Glu Glu Leu Glu
            20                  25                  30

Lys Asp Leu Arg Lys Ala Arg Lys Thr Ile Lys Lys Leu Glu Glu Glu
                35                  40                  45

Asn Pro Trp Leu Gly Asn Ile Leu Gly Ile Ile Arg Lys Gly Lys Asp
        50                  55                  60

Gly Glu Gly Ala Pro Pro Ala Lys Arg Ser Arg Thr Asp Gln Met Glu
65                  70                  75                  80

Val Asp Ser Gly Thr Gly Lys Arg Pro His Arg Ser Gly Phe Thr Asp
                    85                  90                  95

Lys Glu Arg Glu Asp His Arg Arg Lys Ala Leu Glu Asn Lys Arg
                100                 105                 110

Lys Gln Leu Ser Ser Gly Gly Lys Ser Leu Ser Arg Glu Glu Glu Glu
            115                 120                 125

Glu Leu Arg Arg Leu Thr Val Glu Asp Glu Glu Arg Lys Arg Arg Val
    130                 135                 140

Ala Gly Pro Arg Val Gly Val Val Asn Pro Ser Gly Gly Pro Arg
145                 150                 155                 160

Gly Ala Pro Gly Gly Phe Val Pro Gln Met Glu Gly Val Pro Glu
                165                 170                 175

Ser Pro Phe Ala Arg Thr Gly Glu Gly Leu Asp Ile Arg Ala Gly Asn
                180                 185                 190

Gln Gly Phe Pro Trp Val His Pro Ser Pro Pro Gln Gln Arg Leu Pro
            195                 200                 205

Leu Leu Glu Cys Thr Pro Gln
        210                 215

<210> SEQ ID NO 71
<211> LENGTH: 213
<212> TYPE: PRT
<213> ORGANISM: Hepatitis D virus

<400> SEQUENCE: 71

Met Ser Gln Ser Glu Thr Arg Gly Arg Gly Arg Gly Thr Arg Glu Glu
1               5                   10                  15

Thr Leu Glu Lys Trp Ile Thr Ala Arg Arg Arg Ala Glu Glu Leu Glu
            20                  25                  30

Lys Asp Leu Arg Lys Thr Arg Thr Ile Lys Lys Leu Glu Glu Glu
                35                  40                  45

Asn Pro Trp Leu Gly Asn Ile Val Gly Ile Ile Arg Lys Gly Lys Asp
        50                  55                  60

Gly Glu Gly Ala Pro Pro Ala Lys Arg Pro Arg Thr Asp Gln Met Glu
65                  70                  75                  80

Val Asp Ser Gly Pro Gly Lys Arg Pro His Lys Ser Gly Phe Thr Asp
                    85                  90                  95

Lys Glu Arg Glu Asp His Arg Arg Lys Ala Leu Glu Asn Lys Lys
                100                 105                 110

Lys Gln Leu Ser Ala Gly Gly Lys Ile Leu Lys Glu Glu Glu Glu
            115                 120                 125
```

```
Leu Arg Arg Leu Thr Asp Glu Asp Glu Arg Lys Arg Arg Val Ala
        130                 135                 140
Gly Pro Arg Val Gly Asp Val Asn Pro Ser Arg Gly Pro Arg Gly
145                 150                 155                 160
Ala Pro Gly Gly Phe Val Pro Gln Met Ala Gly Val Pro Glu Ser
                165                 170                 175
Pro Phe Ser Arg Thr Gly Glu Gly Leu Asp Ile Arg Gly Thr Gln Gly
            180                 185                 190
Phe Pro Glx Val Ser Pro Ser Pro Gln Gln Arg Leu Pro Leu Leu
            195                 200                 205
Glu Cys Thr Pro Gln
        210

<210> SEQ ID NO 72
<211> LENGTH: 215
<212> TYPE: PRT
<213> ORGANISM: Hepatitis D virus

<400> SEQUENCE: 72

Met Ser Gln Ser Glu Ser Arg Lys Ser Arg Gly Gly Arg Glu Asp
1               5                   10                  15
Ile Leu Glu Lys Trp Val Ser Thr Arg Lys Ala Glu Glu Leu Glu
            20                  25                  30
Arg Asp Leu Arg Lys Ala Arg Lys Thr Ile Lys Arg Leu Glu Asp Asp
        35                  40                  45
Asn Pro Trp Leu Gly Asn Ile Leu Gly Ile Ile Arg Lys Gly Lys Asp
    50                  55                  60
Gly Glu Gly Ala Pro Pro Ala Lys Arg Ala Arg Thr Asp Gln Met Glu
65                  70                  75                  80
Val Asp Ser Gly Pro Arg Lys Lys Pro His Lys Ser Gly Phe Thr Asp
                85                  90                  95
Lys Glu Arg Gln Asp His Arg Arg Lys Ala Leu Gln Asn Lys Asn
                100                 105                 110
Lys Gln Leu Ser Ala Gly Gly Lys Ser Leu Ser Lys Glu Glu Glu
            115                 120                 125
Glu Leu Arg Arg Leu Thr Ile Glu Asp Asp Glu Arg Gln Arg Arg Val
        130                 135                 140
Ala Gly Pro Arg Val Gly Asp Val Asn Pro Gly Gly Ser Pro Arg
145                 150                 155                 160
Gly Ala Pro Gly Gly Phe Val Pro Gln Met Thr Gly Val Pro Glu
                165                 170                 175
Ser Pro Phe Ser Arg Thr Gly Glu Gly Leu Asp Ile Arg Ala Gly Asp
            180                 185                 190
Arg Gly Phe Pro Trp Val Asn Pro Ala Gly Gln Pro Pro Arg Leu Pro
            195                 200                 205
Leu Leu Glu Cys Thr Pro Gln
    210                 215

<210> SEQ ID NO 73
<211> LENGTH: 215
<212> TYPE: PRT
<213> ORGANISM: Hepatitis D virus

<400> SEQUENCE: 73

Met Ser Gln Pro Glu Ser Arg Lys Gly Arg Gly Gly Arg Glu Glu
1               5                   10                  15
```

-continued

```
Ile Leu Glu Lys Trp Ile Ser Thr Arg Arg Lys Ala Glu Glu Leu Glu
         20                  25                  30

Arg Asp Leu Arg Lys Ala Arg Lys Thr Ile Lys Arg Leu Glu Asp Glu
         35                  40                  45

Asn Pro Trp Leu Gly Asn Ile Leu Gly Ile Ile Arg Lys Gly Lys Asp
     50                  55                  60

Gly Glu Gly Ala Pro Pro Ala Lys Arg Ala Arg Thr Asp Gln Met Glu
 65              70                  75                  80

Val Asp Ser Gly Pro Met Lys Arg Pro His Lys Ser Gly Phe Thr Asp
                 85                  90                  95

Lys Glu Arg Glu Asp His Arg Arg Lys Ala Leu Glu Asn Lys Arg
                100                 105                 110

Lys Gln Leu Ser Ala Gly Gly Lys Asn Leu Ser Arg Glu Glu Glu
            115                 120                 125

Glu Leu Arg Arg Leu Thr Glu Glu Asp Glu Arg Arg Glu Arg Val
        130                 135                 140

Ala Gly Pro Arg Val Gly Asp Val Asn Pro Pro Gly Gly Ser Pro Arg
145                 150                 155                 160

Gly Ala Pro Gly Gly Phe Val Pro Gln Met Thr Gly Val Pro Glu
                165                 170                 175

Ser Pro Phe Thr Arg Thr Gly Glu Gly Leu Asp Ile Arg Thr Gly Thr
            180                 185                 190

Gln Gly Phe Pro Trp Val Asn Pro Val Pro Gly Gln Arg Leu Pro
        195                 200                 205

Leu Leu Glu Cys Thr Pro Gln
    210                 215

<210> SEQ ID NO 74
<211> LENGTH: 215
<212> TYPE: PRT
<213> ORGANISM: Hepatitis D virus

<400> SEQUENCE: 74

Met Ser Gln Ser Glu Ser Lys Lys Ala Arg Arg Gly Gly Arg Glu Glu
1               5                   10                  15

Ile Leu Glu Lys Trp Val Gln Ala Arg Lys Asp Ser Glu Asp Leu Glu
         20                  25                  30

Lys Lys Leu Arg Lys Thr Lys Arg Thr Ile Lys Lys Leu Glu Asp Glu
         35                  40                  45

Asn Pro Trp Leu Gly Asn Ile Leu Gly Ile Ile Arg Lys Gly Lys Asp
     50                  55                  60

Gly Glu Gly Ala Pro Pro Ala Lys Arg Ala Arg Thr Asp Gln Met Glu
 65              70                  75                  80

Val Asp Ser Gly Pro Arg Lys Arg Thr Arg Ala Gly Asp Phe Thr Asp
                 85                  90                  95

Gln Glu Arg Lys Asp His Arg Arg Lys Ala Leu Glu Asn Lys Lys
                100                 105                 110

Asn Gln Leu Ser Ala Gly Gly Lys Ser Leu Ser Arg Glu Glu Glu
            115                 120                 125

Glu Leu Arg Lys Leu Thr Glu Glu Asp Glu Arg Arg Glu Arg Val
        130                 135                 140

Ala Gly Pro Arg Val Gly Asp Val Asn Pro Pro Glu Gly Gly Pro Arg
145                 150                 155                 160

Gly Ala Pro Gly Gly Phe Val Pro Gln Met Leu Asp Val Pro Glu
                165                 170                 175
```

Ser Pro Phe Ser Arg Thr Gly Ser Gly Leu Asp Val Arg Ala Gly Asn
            180                 185                 190

Gln Gln Phe Pro Trp Val Asp Pro Gly Arg Pro Pro Arg Leu Pro
        195                 200                 205

Leu Leu Glu Cys Thr Pro Gln
    210                 215

<210> SEQ ID NO 75
<211> LENGTH: 215
<212> TYPE: PRT
<213> ORGANISM: Hepatitis D virus

<400> SEQUENCE: 75

Met Ser Gln Ser Glu Gln Arg Lys Pro Arg Gly Gly Arg Glu Asp
1               5                   10                  15

Val Leu Glu Lys Trp Ile Gln Ala Arg Lys Asp Ala Glu Asp Leu Glu
            20                  25                  30

Lys Arg Leu Arg Lys Ala Lys Arg Thr Ala Lys Lys Leu Glu Asp Glu
        35                  40                  45

Asn Pro Trp Leu Gly Asn Ile Leu Gly Ile Ile Arg Lys Gly Lys Asp
    50                  55                  60

Gly Glu Gly Ala Pro Pro Ala Lys Arg Ala Arg Thr Asp Gln Met Glu
65                  70                  75                  80

Val Asp Ser Gly Pro Arg Lys Arg Thr Arg Ala Gly Asp Phe Thr Asp
                85                  90                  95

Lys Glu Arg Arg Asp His Arg Arg Lys Ala Leu Glu Asn Lys Lys
            100                 105                 110

Lys Gln Leu Ser Ala Gly Gly Lys Ser Leu Ser Lys Glu Glu Glu
        115                 120                 125

Glu Leu Arg Lys Leu Thr Glu Glu Asp Glu Arg Arg Glu Arg Arg Val
    130                 135                 140

Ala Gly Pro Arg Val Gly Asp Val Asn Pro Pro Gly Thr Ser Pro Arg
145                 150                 155                 160

Gly Ala Pro Gly Gly Phe Val Pro Gln Met Leu Gly Val Pro Glu
                165                 170                 175

Ser Pro Phe Ser Arg Thr Gly Glu Gly Leu Asp Val Arg Ala Gly Asn
            180                 185                 190

Gln Gln Tyr Pro Trp Val Asn Pro Gly Pro Arg Pro Arg Leu Pro
        195                 200                 205

Leu Leu Glu Cys Thr Pro Gln
    210                 215

<210> SEQ ID NO 76
<211> LENGTH: 216
<212> TYPE: PRT
<213> ORGANISM: Hepatitis D virus

<400> SEQUENCE: 76

Met Ser Gln Ser Glu Gln Lys Lys Ser Arg Gly Gly Arg Glu Glu Thr
1               5                   10                  15

Leu Glu Lys Trp Ile Gln Ala Arg Lys Asp Ala Glu Asp Leu Glu Lys
            20                  25                  30

Arg Leu Arg Lys Thr Lys Arg Thr Ile Lys Arg Leu Glu Asp Glu Asn
        35                  40                  45

Pro Trp Leu Gly Asn Val Leu Gly Ile Ile Arg Lys Gly Lys Asp Gly
    50                  55                  60

```
Glu Gly Ala Pro Pro Ala Lys Arg Ala Arg Thr Asp Gln Met Glu Val
 65                  70                  75                  80

Asp Ser Gly Pro Arg Lys Arg Thr Arg Ala Gly Asp Phe Thr Asp Lys
                 85                  90                  95

Glu Gln Glu Arg Arg Asp His Arg Arg Arg Lys Ala Leu Glu Asn Lys
            100                 105                 110

Lys Lys Gln Leu Ser Ala Gly Gly Lys Ser Leu Ser Lys Glu Glu
        115                 120                 125

Glu Glu Leu Lys Arg Leu Thr Glu Glu Asp Glu Arg Arg Glu Arg Arg
    130                 135                 140

Val Ala Gly Pro Arg Val Gly Asp Val Asn Pro Pro Gln Gly Gly Pro
145                 150                 155                 160

Arg Gly Ala Pro Gly Gly Gly Phe Val Pro Gln Met Leu Asn Val Pro
                165                 170                 175

Glu Ser Pro Phe Thr Thr Arg Gly Glu Gly Leu Asp Ile Arg Ala Gly
                180                 185                 190

Asn Gln Gln Phe Pro Trp Val Ser Pro Gly Ala Pro Ser Pro Arg Leu
                195                 200                 205

Pro Leu Leu Glu Cys Thr Pro Gln
    210                 215

<210> SEQ ID NO 77
<211> LENGTH: 215
<212> TYPE: PRT
<213> ORGANISM: Hepatitis D virus

<400> SEQUENCE: 77

Met Ser Gln Ser Asp Ala Lys Arg Glu Arg Gly Gly Arg Glu Asp
1                5                  10                  15

Val Leu Ser Lys Trp Val Glu Ala Arg Lys Asp Leu Glu Asp Leu Glu
                 20                  25                  30

Lys Arg Ile Arg Lys Thr Arg Arg Asn Ile Lys Arg Leu Glu Asp Glu
             35                  40                  45

Asn Pro Trp Leu Gly Asn Ile Leu Gly Ile Ile Arg Lys Gly Lys Ala
 50                  55                  60

Gly Glu Gly Ala Pro Pro Ala Lys Arg Ala Arg Thr Asp Gln Met Glu
 65                  70                  75                  80

Val Asp Ser Gly Gly Gly Lys Lys Ser Arg Lys Gly Gly Phe Thr Asp
                 85                  90                  95

Glu Glu Arg Arg Asp His Arg Arg Arg Lys Ala Leu Glu Asn Lys Lys
            100                 105                 110

Lys Gln Leu Ser Ser Gly Lys Lys Leu Ser Glu Glu Glu Gly
         115                 120                 125

Glu Leu Arg Arg Leu Thr Val Glu Asp Glu Lys Arg Glu Arg Ala Val
    130                 135                 140

Ala Gly Pro Gln Asp Gly Gly Val Asn Pro Gly Gly Ser Pro Arg
145                 150                 155                 160

Gly Ala Pro Gly Gly Gly Phe Val Pro Arg Met Leu Gly Val Pro Glu
                165                 170                 175

Ser Pro Phe Thr Arg Arg Gly Asp Gly Leu Asp Ile Arg Ala Gly Asp
                180                 185                 190

Gln Gln Phe Pro Trp Gly Gln Arg Pro Pro Pro Arg Leu Pro
        195                 200                 205

Leu Leu Glu Cys Thr Pro Gln
```

<210> SEQ ID NO 78
<211> LENGTH: 214
<212> TYPE: PRT
<213> ORGANISM: Hepatitis D virus

<400> SEQUENCE: 78

Met Ser His Ala Asp Thr Lys Arg Ser Arg Lys Gly Arg Glu Glu Thr
1               5                   10                  15

Leu Ser Lys Trp Asp Lys Ala Arg Glu Asp Ala Glu Glu Leu Glu Arg
            20                  25                  30

Arg Leu Arg Lys Thr Lys Lys Thr Ile Lys Lys Leu Glu Asp Asp Asn
        35                  40                  45

Pro Trp Leu Gly Asn Ile Lys Gly Ile Ile Gly Lys Val Gly Thr Gly
50                  55                  60

Glu Gly Ala Pro Pro Ala Lys Arg Pro Arg Thr Asp Arg Met Glu Val
65                  70                  75                  80

Asp Ser Gly Pro Gly Lys Lys Ser Asn Lys Gly Gly Phe Thr Asp Glu
                85                  90                  95

Glu Arg Arg Ala His Arg Arg Lys Ala Leu Glu Asn Lys Lys Lys
            100                 105                 110

Gln Leu Ser Ala Gly Lys Ser Leu Ser Lys Glu Glu Glu Glu
            115                 120                 125

Leu Arg Lys Leu Ala Asp Glu Asp Glu Gln Arg Ala Arg Ile Ala
        130                 135                 140

Gly Pro Arg Val Gly Asp Val Asn Pro Glu Gly Gly Pro Arg Gly
145                 150                 155                 160

Ala Pro Gly Gly Gly Phe Val Pro Gln Leu Leu Gly Val Pro Glu Ser
                165                 170                 175

Pro Phe Ser Arg Thr Gly Glu Gly Leu Asp Ile Arg Ala Gly Asp Arg
            180                 185                 190

Gln Phe Pro Trp Gly Pro Ser Pro Thr Pro Pro Arg Leu Pro Leu
        195                 200                 205

Leu Glu Cys Thr Pro Gln
    210

<210> SEQ ID NO 79
<211> LENGTH: 216
<212> TYPE: PRT
<213> ORGANISM: Hepatitis D virus

<400> SEQUENCE: 79

Met Gly Pro Ala Glu Gln Lys Arg Pro Lys Gly Gly Arg Glu Glu
1               5                   10                  15

Ile Leu Glu Lys Trp Ile Val Glu Leu Arg Lys Asn Arg Glu Asp Leu
            20                  25                  30

Glu Arg Asp Leu Arg Lys Thr Gln Lys Gly Leu Lys Lys Leu Glu Asp
        35                  40                  45

Asp Asn Pro Trp Leu Gly Asn Ile Ile Gly Ile Ile Arg Lys Gly Lys
50                  55                  60

Asp Gly Glu Gly Ala Pro Pro Thr Lys Lys Ala Arg Thr Asp Gln Met
65                  70                  75                  80

Glu Val Asp Ser Gly Pro Arg Gly Lys Pro His Lys Ser Gly Phe Thr
                85                  90                  95

Asp Glu Glu Arg Arg Asp His Arg Arg Arg Lys Ala Leu Glu Asn Lys

```
            100                 105                 110
Lys Lys Gln Leu Ala Ala Gly Gly Lys Asn Leu Ser Arg Glu Glu
        115                 120                 125

Glu Glu Leu Gly Arg Leu Thr Gly Glu Asp Glu Gln Arg Lys Arg
        130                 135                 140

Thr Ala Gly Pro Arg Val Gly Asp Val Asn Pro Pro Gly Asp Pro
145                 150                 155                 160

Arg Gly Ala Pro Gly Gly Phe Val Pro Thr Met Leu His Val Pro
                165                 170                 175

Glu Ser Pro Phe Ser Arg Thr Gly Glu Gly Leu Asp Val Arg Ala Gly
        180                 185                 190

Thr Gln Gln Phe Pro Trp Gly Asn Thr Pro Arg Pro Pro Arg Leu
        195                 200                 205

Pro Leu Leu Glu Cys Thr Pro Gln
        210                 215

<210> SEQ ID NO 80
<211> LENGTH: 215
<212> TYPE: PRT
<213> ORGANISM: Hepatitis D virus

<400> SEQUENCE: 80

Met Ser Arg Thr Glu Ser Lys Lys Asn Arg Gly Gly Arg Glu Asp Ala
1               5                   10                  15

Leu Glu Gln Trp Val Asn Gly Arg Arg Arg Ile Glu Glu Leu Glu Arg
                20                  25                  30

Asp Leu Arg Lys Ala Lys Lys Ile Lys Lys Leu Glu Asp Asp Asn
            35                  40                  45

Pro Trp Leu Gly Asn Ile Lys Gly Ile Leu Gly Lys Lys Asp Lys Asp
        50                  55                  60

Gly Glu Gly Ala Pro Pro Ala Lys Arg Ala Arg Thr Asp Gln Met Glu
65                  70                  75                  80

Val Asp Ser Gly Pro Arg Lys Arg Pro Leu Arg Gly Gly Phe Thr Asp
                85                  90                  95

Lys Glu Arg Gln Asp His Arg Arg Arg Lys Ala Leu Glu Asn Lys Lys
            100                 105                 110

Lys Gln Leu Ser Ala Gly Gly Lys His Leu Ser Arg Glu Glu Glu
        115                 120                 125

Glu Leu Lys Arg Leu Thr Glu Glu Asp Glu Arg Arg Glu Arg Arg Ala
        130                 135                 140

Ala Gly Pro Pro Val Gly Gly Val Asn Pro Leu Glu Gly Gly Gln Arg
145                 150                 155                 160

Gly Ala Pro Gly Gly Gly Phe Val Pro Ser Met Gln Gly Val Pro Glu
                165                 170                 175

Ser Pro Phe Thr Arg His Gly Glu Gly Leu Asp Val Arg Ala Gly Thr
        180                 185                 190

Gly Gly Phe Pro Glx Asp Ile Leu Phe Pro Pro Ser Asp Pro Phe Ser
        195                 200                 205

Pro Gln Ser Cys Arg Pro Gln
        210                 215

<210> SEQ ID NO 81
<211> LENGTH: 215
<212> TYPE: PRT
<213> ORGANISM: Hepatitis D virus
```

```
<400> SEQUENCE: 81

Met Ser Arg Ser Glu Ser Arg Lys Asn Arg Gly Gly Arg Glu Glu Ile
1               5                   10                  15

Leu Glu Gln Trp Val Ala Gly Arg Lys Lys Leu Glu Glu Leu Glu Arg
            20                  25                  30

Asp Leu Arg Lys Thr Lys Lys Lys Leu Lys Lys Ile Glu Asp Glu Asn
        35                  40                  45

Pro Trp Leu Gly Asn Ile Lys Gly Ile Leu Gly Lys Lys Asp Lys Asp
    50                  55                  60

Gly Glu Gly Ala Pro Pro Ala Lys Arg Ala Arg Thr Asp Gln Met Glu
65                  70                  75                  80

Val Asp Ser Gly Pro Arg Lys Arg Pro Leu Arg Gly Gly Phe Thr Asp
                85                  90                  95

Lys Glu Arg Gln Asp His Arg Arg Lys Ala Leu Glu Asn Lys Lys
            100                 105                 110

Lys Gln Leu Ser Ala Gly Gly Lys Asn Leu Ser Lys Glu Glu Glu
            115                 120                 125

Glu Leu Arg Arg Leu Thr Glu Glu Asp Glu Arg Arg Glu Arg Arg Val
            130                 135                 140

Ala Gly Pro Pro Val Gly Gly Val Ile Pro Leu Glu Gly Gly Ser Arg
145                 150                 155                 160

Gly Ala Pro Gly Gly Gly Phe Val Pro Ser Leu Gln Gly Val Pro Glu
                165                 170                 175

Ser Pro Phe Ser Arg Thr Gly Glu Gly Leu Asp Ile Arg Ala Gly Asn
            180                 185                 190

Arg Gly Phe Pro Trp Asp Ile Leu Phe Pro Ala Asp Arg Pro Phe Ser
            195                 200                 205

Pro Gln Ser Cys Arg Pro Gln
    210                 215

<210> SEQ ID NO 82
<211> LENGTH: 214
<212> TYPE: PRT
<213> ORGANISM: Hepatitis D virus

<400> SEQUENCE: 82

Met Ser Arg Ser Glu Gln Lys Lys Asn Arg Gly Gly Arg Glu Asp Thr
1               5                   10                  15

Leu Glu Lys Trp Val Asn Glu Arg Lys Lys Ala Glu Glu Leu Glu Lys
            20                  25                  30

Glu Leu Arg Lys Ala Lys Lys Lys Ile Lys Lys Leu Glu Glu Glu Asn
        35                  40                  45

Pro Trp Leu Gly Asn Ile Lys Gly Ile Leu Gly Lys Lys Asp Lys Asp
    50                  55                  60

Gly Glu Gly Ala Pro Pro Ala Lys Arg Pro Arg Thr Asp Gln Met Glu
65                  70                  75                  80

Ile Asp Ser Gly Pro Arg Lys Lys Pro Leu Arg Gly Gly Phe Thr Asp
                85                  90                  95

Lys Glu Arg Glu Asp Pro Arg Arg Lys Ala Leu Glu Asn Lys Lys
            100                 105                 110

Lys Gln Leu Ser Ala Gly Gly Lys Asn Leu Ser Lys Glu Glu Glu
            115                 120                 125

Glu Leu Arg Arg Leu Ala Arg Glu Asp Glu Glu Arg Ser Arg Arg Ile
            130                 135                 140
```

-continued

```
Ala Gly Pro Ser Ala Gly Gly Val Asn Pro Leu Glu Gly Gly Ser Arg
145                 150                 155                 160

Gly Ala Pro Gly Gly Gly Phe Val Pro Ser Met Gln Gly Ile Pro Glu
                165                 170                 175

Ser Pro Phe His Arg Arg Gly Glu Gly Leu Asp Val Thr Ala Gly Thr
            180                 185                 190

Gly Gly Phe Pro Glx Asp Ile Leu Phe Pro Ser Asp Pro Pro Phe Ser
        195                 200                 205

Pro Gln Ser Thr Arg Gln
    210

<210> SEQ ID NO 83
<211> LENGTH: 216
<212> TYPE: PRT
<213> ORGANISM: Hepatitis D virus

<400> SEQUENCE: 83

Met Ser Gln Thr Val Ala Arg Leu Thr Ser Lys Glu Arg Glu Glu Ile
1               5                   10                  15

Leu Glu Gln Trp Val Glu Glu Arg Lys Asn Arg Arg Lys Leu Glu Lys
            20                  25                  30

Asp Leu Arg Arg Ala Asn Lys Lys Ile Lys Lys Leu Glu Asp Glu Asn
        35                  40                  45

Pro Trp Leu Gly Asn Val Val Gly Leu Leu Arg Arg Arg Lys Lys Asp
    50                  55                  60

Glu Asp Gly Ala Pro Pro Pro Lys Gln Glu Thr Thr Asp Gln Met Glu
65                  70                  75                  80

Val Asp Ser Gly Pro Gly Arg Lys Pro Lys Ala Arg Gly Phe Thr Asp
                85                  90                  95

Gln Glu Arg Arg Asp His Arg Arg Arg Lys Ala Leu Glu Asn Lys Lys
            100                 105                 110

Lys Gln Leu Ala Gly Gly Gly Lys His Leu Ser Gln Glu Glu Glu Glu
        115                 120                 125

Glu Leu Arg Arg Leu Ala Arg Asp Asp Asp Glu Arg Glu Arg Arg Thr
    130                 135                 140

Ala Gly Pro Arg Pro Gly Gly Val Asn Pro Met Asp Gly Pro Pro Arg
145                 150                 155                 160

Gly Ala Pro Gly Gly Gly Phe Val Pro Ser Leu Gln Gly Val Pro Glu
                165                 170                 175

Ser Pro Phe Ser Arg Thr Gly Glu Gly Ile Asp Ile Arg Ala Gly Thr
            180                 185                 190

Gln Gln Phe Pro Trp Tyr Gly Phe Thr Pro Pro Pro Pro Gly Tyr Tyr
        195                 200                 205

Trp Val Pro Gly Cys Thr Gln Gln
    210                 215
```

HDV NUCLEIC ACID MOLECULES AND APPLICATIONS THEREOF

CROSS-REFERENCE TO RELATED APPLICATIONS

The present application is a 371 application of PCT/FR02/03239 filed Sep. 23, 2002 and which also claims the benefit of FR 01/12285 filed on Sep. 24, 2001.

The present invention relates nucleic acid molecules derived from novel hepatitis D virus strains or isolates constituting genotypes different from the known genotypes I, II and III, and to their fragments, to the corresponding proteins, and also to their uses as diagnostic reagents.

The present invention also relates to a method for sensitive diagnosis of the hepatitis D virus (or delta hepatitis virus) and to a method for epidemiological monitoring of HDV infections.

The hepatitis D virus (HDV) or delta hepatitis virus is a hepatitis B satellite virus. This virus has a specific structure: chimeric structure associating with the specific HDV components (viral RNA and HD proteins), an envelope comprising the three HBV glycoproteins: large (preS1-preS2-S), medium (preS2-S) and small (S). The average diameter of HDV particles is between that of mature HBV particles (Dane particles: 42 nm) and that of HBV empty envelopes (spherical or filamentous form: 22 nm) and the flotation density is 1.24-1.25 g/cm$^3$.

In the virions, the HDV RNA is circular and of negative polarity. This closed circular single strand, the smallest known genome of viruses which infect mammals, has a high GC percentage (60%).

The HDV RNA replicates independently of HBV, the role of which is limited to providing the envelope of HDV. The only proteins found (sHD and LHD) are encoded by the antigenomic RNA which, in the infected cell, is complete, circular and pseudo-double-stranded, serves as a replication intermediate and is the target for editing.

The HDV RNA belongs to a specific type of ribozyme. The self-cleavage reaction requires the RNA and a divalent cation (Mg$^{++}$). The cleavage creates a 2',3'-cyclic phosphate end and a hydroxyl 5' end. Delta ribozymes (genomic and antigenomic) have a similar pseudoknot secondary structure. The sequences involved include mainly or exclusively sequences located 3' of the self-cleavage site (approximately 84 nucleotides).

During the viral cycle the HDV mRNA encodes a protein, two forms of which exist: a 194-195 amino acids protein ('s' form for small) of 24 kilodaltons (kDa) and a 214 amino acids protein ('L' form for large) of 27 kDa, which exist in varying proportions. These proteins carry the 'delta' antigenicity and are detected in the liver or the serum of infected patients or animals (chimpanzee, marmot). These two viral proteins sHD and LHD are initiated at the first ATG of the open reading frame located at position 1598 (according to the numbering of Wang et al., 1986 or 1987) of the antigenomic RNA. During replication, a mutation, dependent on a cellular enzyme, 'double-stranded RNA-dependent adenosine deaminase' appears at position 1012, converting the amber stop codon (UAG) into a tryptophan codon (UGG), extending the reading frame by 19 or 20 codons in the 3' direction, and conferring different properties on the two forms sHD and LHD.

The mRNA terminates with a poly(A) tail, 15 nucleotides after the polyadenylation consensus signal AAUAAA (positions 954-959).

In the replication cycle, the functions of the 24 and 27 Kd proteins are opposite: sHD activates viral replication, whereas LHD suppresses it and plays a role in assembly of the viral particles. These proteins are phosphorylated on serine residues but not glycosylated (Table I). They consist of common functional domains and of a domain specific to the large protein LHD.

TABLE I

Summary and comparison of the functions of the two forms p24 and p27

| Biochemical and biological activities | p24 (S) | p27 (L) |
|---|---|---|
| amino acids | 195 | 214 |
| transactivation of replication | + | − |
| transinhibition of replication | − | + |
| dimerization and polymerization | + | + |
| RNA binding | + | + |
| RNA stabilization | + | + |
| nuclear localization | + | + |
| assembly | − | + |
| phosphorylation | + | + (×6) |
| 19 specific carboxy-terminal aa | − | + |
| farnesylation | − | + |

Briefly, the various domains of these two proteins are as follows:

Common Domains

The polymerization domain, which comprises the sequence between amino acid residues 13 and 48, made up of an arrangement of leucine or isoleucine, organized in a "leucine zipper"-type α-helix, involved in protein polymerization, essential for (i) transactivation of viral replication by the sHD-Ag, (ii) inhibition of replication by the LHD-Ag and (iii) assembly of the sHD-LHD complexes in HBV envelopes.

The nuclear localization signal (NLS), which involves two nuclear localization sequences identified in the 67-88 region, essential for translocating the sHD-Ag synthesized in the cytoplasm, and perhaps the ribonucleoprotein after its entry into the cell, to the nucleus.

The RNA-binding site which is based on two arginine-rich sequences located between residues 97 and 163, which allow binding of the sHD proteins to the genomic or antigenomic RNA. This binding is essential for the sHD-Ag to activate replication.

Specific Domains

The 19-20 amino acids located at the COOH end of the large protein have an important role in the HDV cycle. Specifically, these amino acids (aa 195-214) are involved in assembly of the viral particles (Chang et al., 1991). This activity could be partly linked to the presence of a cysteine at position 211 (Glenn et al., 1992), which is conserved for all viral genomes characterized to date. This cysteine, located 4 amino acids before the COOH end of the protein, forms a "CXXX" box and attaches a farnesyl group (Glenn et al., 1992), a 15 carbon chain derived from mevalonic acid, through the action of a farnesyltransferase. This post-translational maturation directs the proteins to the cell membranes.

The small and the large protein have, moreover, been differentiated with monoclonal antibodies (clone 9E4) (Hwang and Lai, 1993a). These antibodies only recognise sHD (Lai et al., 1993). Since the amino acid sequence of the small protein is included in the large protein, these results suggest a difference in conformation between sHD and LHD within the 30 carboxy-terminal amino acids of the small protein sHD, suggesting that the epitope recognised on sHD is masked in LHD under non-denaturing conditions.

HDV is transmitted especially via contaminated needles and blood, and therefore via HDV or HBV carriers.

In North America and in Western Europe, hepatitis D is therefore found especially in intravenous drug users, hemophiliacs and individuals who have received multiple transfusions.

The epidemiology and the methods of contamination partially superimpose one another. It is estimated overall that the proportion of HBs-Ag carriers infected with HDV is 5%. However, disparities in geographical and epidemiological prevalence are noted.

A high prevalence of this disease, in hepatitis B virus carriers, exists in certain regions of the world, including the Amazon Basin of South America, central Africa and southern Italy, and in the countries of the Middle East.

In the Mediterranean region, most particularly in southern Italy, in Greece and in the Middle East, where the frequency of chronic HBV carriers is intermediate (1% to 5%), infection with HDV is high. In these regions, intrafamily transmission has been suggested, argued on the basis of phylogenetic studies of virus infecting members of the same family (Niro et al., 1999). In southern Italy, the prevalence in HBS-Ag-positive individuals is decreasing, dropping from 23% in 1987 to 8% in 2000 (Gaeta et al., 2000).

In Africa and in Asia, where the frequency of chronic HBV carriers is high (10% to 20%), and also in South America and in the Pacific Islands, where this frequency is intermediate (1% to 5%), the distribution of HDV is paradoxically disparate. In Africa, seroprevalence studies show a very heterogeneous distribution of patients having anti-HD antibodies, whereas the overall prevalence of HBV infection, estimated by detecting HBs-Ag, stabilizes between 12 and 14% (Roingeard et al., 1992). Thus, varying levels of 4% (northern region of Senegal) to 44% (Dakar suburbs) reveal probable socioeconomic factors involved in transmission.

HDV prevalence studies should be interpreted carefully. This is because, in the populations studied, there is a preferential inclusion of patients suffering from hepatopathies. In patients suffering from acute to chronic hepatitis, the prevalence of HDV infection is greater than in chronic asymptomatic HBV carriers. In addition, the serological investigation of an HDV infection is based on the detection of HD-Ag and of total anti-HD antibodies in the serum. As a result, acute benign infections, during which an isolated transient production of anti-HD IgM would develop, would not be registered.

HDV is responsible for acute and chronic forms of hepatitis. These infections are particularly serious and evolve more rapidly to cirrhosis than hepatitis B alone. This is one of the reasons for which the reliable diagnosis of HDV associated with HBV is crucial.

Infection with an HDV is dependent on HBV. HDV isolates from different geographical regions show genetic variability. Currently, three genotypes have been identified and named genotype-I, -II and -III.

The genotype is used for the viral transmission epidemiology, makes it possible to study the geographic distribution and might be correlated with the pathogenic potency.

HDV only develops in patients also infected with HBV. This double infection ensues either from a co-infection or from a superinfection:

Co-infection is the cause of an acute hepatitis. The diagnosis, invoked during hepatic cytolysis, is based on the detection of markers for HDV associated with the presence of anti-HBc IgM. The HBs-Ag, which is generally present, is exceptionally negative, justifying repetition of the samples in order to monitor the kinetic of evolution of the markers. It is conventional to observe an inhibition of HBV replication by HDV. The anti-HBc IgMs reflect the recent infection with HBV. The HD-Ag, which is very early, is rarely detected given its transient nature. The antibodies appear 2 to 3 weeks after the beginning of symptoms: anti-HD IgMs are predominant, but the titer thereof remains moderate (<1:1000). Two transaminase elevation peaks, separated by two to five weeks, are observed in 10 to 20% of co-infections, probably reflecting different viral replication kinetics. Co-infection is therefore characterized by the acute hepatitis often being more severe than that caused by HBV alone. Thus, fulminant hepatitis is described in South America and in sub-Saharan Africa or in certain populations. The progression is generally marked by resolution of the hepatitis after the acute phase and, in the image of the natural history of HBV, only 5% of co-infected patients progress to a chronic form of the disease.

Superinfection is characterized by the appearance of an HDV seroconversion in a patient who is a chronic HBs-Ag carrier. The HDV viremia precedes the appearance of anti-HDV antibodies in the absence of detection of anti-HBc IgMs. The detection of these markers may precede an increase in transaminases by several months. In the acute phase, the superinfection results in fulminant hepatitis in more than 10% of cases. In addition, once the acute phase has passed, the superinfection frequently (60 to 70%) results in chronic active hepatitis with rapid progression to cirrhosis. In the acute phase of the superinfection, detection of the HD-Ag is rapidly followed by the appearance of antibodies, which persist at high levels. Unlike the conventional models of viral infection, anti-HD IgG and anti-HD IgM are simultaneously detected in chronic hepatitis B-delta.

Table II below summarizes the evolution of the B and delta markers during co-infections and superinfections.

|  | Evolution | | |
| --- | --- | --- | --- |
|  | Acute phase | Chronic | Recovery |
| Co-infection with HDV | | | |
| HBs-Ag | + | + | − |
| anti-HBc IgM | + | − | − |
| HD-Ag | +/− | − | − |
| anti-HD IgM | +/− | + | − |
| anti-HD IgG | +/− | + | + |
| HDV RNA | + | + | − |
| intrahepatic HD-Ag | + | + | − |
| Superinfection with HDV | | | |
| HBs-Ag | + | + | − |
| anti-HBc IgM | − | − | − |
| HD-Ag | +/− | − | − |
| anti-HD IgM | + | + | − |
| anti-HD IgG | + | + | + |
| HDV RNA | + | + | − |
| intrahepatic HD-Ag | + | + | − |

Co-infection and superinfection are clinically indistinct. The virological diagnosis is usually based on the various serum markers. More rarely, the HD-AG can be detected on the anatomical/pathological liver biopsy sections.

The markers make it possible to follow the progression of the disease to recovery or to a chronic form, to decide upon what treatment should be given to a patient and to evaluate the effectiveness thereof.

HDV cannot be isolated in cell culture and the diagnosis is therefore based essentially on the search for HD-Ag (ELISA, IF) or for the viral genome (hybridization, PCR, real-time PCR) for direct techniques and on the detection of anti-HD IgM and anti-HD IgG antibodies for indirect methods (ELISA).

The search for intrahepatic HD-Ag can be questioned in fulminant hepatitis given the kinetics of appearance of the seromarkers. This examination is of value as a reference for studying HDV replication, but cannot be used routinely.

Serum HD-Ag is sought in the serum in the presence of a dissociating agent which exposes the HD-Ag, included in the viral envelope bearing the HBs-Ag. The presence of a high titer of anti-HD antibodies (Abs) (chronic hepatitis) which bind the serum antigens impairs the detection. Western blotting techniques have been developed for research purposes. The presence of the virus in the blood is transient and limited to the early phase of infection, and the possibility of detecting the HD-Ag decreases over the days following the appearance of symptoms.

Immunocapture is used to detect anti-HD IgMs and competition for anti-HD IgGs. The ELISA techniques first used as antigen the HD-Ag from serum or from liver of infected patients or animals. The new assays are based on recombinant HD-Ags or synthetic peptides.

Hybridization or RT-PCR techniques make it possible to detect the genomic RNA after extraction of the nucleic acids and denaturation of the secondary structures. Several primer systems have been described: the choice thereof is determinant since the genetic variability in "conserved" regions can result in false negatives if the primers chosen are not suitable for the circulating viral strains. The choice of PCR primers should take into account the local epidemiology of the genotypes described, and it is essential to be fully aware of the distribution of these genotypes throughout the world.

However, both in the case of co-infection and in the case of superinfection, the HD-Ag is in fact difficult to detect, although the viremia precedes the appearance of antibodies.

In this context, and in particular due to the demonstration of new genotypes, nucleic acid and protein reagents for diagnosing HDV, whatever the genotype, are needed.

In fact, the study of the nucleotide sequences of HDV by various teams around the world has made it possible to differentiate, until now, only three distinct genotypes:

genotype-I, which is the most common and the most widespread throughout the world. Since the initial description (experimentally infected chimpanzee) by Wang (Wang et al., 1986; Wang et al., 1987), several groups have sequenced the genome of HDV from different geographical isolates. The first sequence of an HDV in humans was described in 1987, in the United States, by S. Makino et al., in a patient who was a drug addict (Makino et al., 1987). Genotype-I is very widespread in Italy, in the United States, Taiwan, Nauru, France, the Lebanon, China (Makino et al., 1987; Chao et al., 1991b; Imazeki et al., 1991; Lee et al., 1992; Niro et al., 1997; and Shakil et al., 1997). Within genotype-I, a percentage of nucleotide similarity of greater than 85% is described.

A Japanese isolate (Imazeki et al., 1990; Imazeki et al., 1991) is the prototype of a $2^{nd}$ subgroup of HDV. This genotype-II, which has initially only been described in Japan and in Taiwan (Imazeki et al., mentioned above; Lee et al., 1996b), appears to have much wider geographical distribution. In particular, genotype-I and genotype-II sequences originating from Yakutia (Russia) have also been characterized. Finally, some authors use an intragenotypic diversity as a basis for dividing genotype-II into subtypes IIA (Imazeki et al., 1990; Imazeki et al., 1991; Lee et al., 1996b), IIB (Wu et al., 1998; Sakugawa et al., 1999) and IIC. In some countries, infection with genotype-II viruses is thought to be associated with forms of hepatitis which are less severe than those caused by genotype-I or -III HDVs (Wu et al., 1995b).

In 1993, a $3^{rd}$ group was described for Peruvian and Colombian virus genomes (Casey et al., 1993a). Genotype-III has only been described in South America, and more particularly in the Amazon Basin, associated with severe hepatitis, or even with epidemic fulminant hepatitis with microvesicular steatosis (Casey et al., 1993a; Casey et al., 1996b) and with high morbidity and mortality. In this geographical region, it is observed that HDV genotype III is preferentially associated with HBV genotype F. Other isolates of this group have recently been isolated in Venezuela (Nakano et al., 2001).

When comparing all the genomes, two to four conserved regions are described (Chao et al., 1991b). Two are consistently found and are centered around the self-cleavage sites of the genomes and antigenomes involved in the autocatalytic activity. The other two conserved regions are located in the reading frame encoding the HD protein (Chao et al., 1991b).

However, the detection techniques are dependent on the genetic variability of the virus sought; the known reagents, in particular based on the sequences specific for genotype-I, -II or -III, do not make it possible to detect infections with a variant HDV and in particular HDVs with a genotype different from those mentioned above.

Consequently, the detection techniques specified above risk giving negative results both at the nucleic acid level and in terms of the antibody response.

The revealing and the taking into account of novel variants are important for developing reagents for detecting and diagnosing hepatitis D (serodiagnosis, PCR, hybridization) which are sufficiently sensitive and specific, i.e. which do not produce falsely negative or falsely positive results: in fact, a positive anti-HD IgM/negative HDV RNA dissociation can, at the current time, be observed in the context of a severe hepatopathy.

In the context of their studies, the inventors have now demonstrated, surprisingly, that the genetic diversity of HDV is significantly greater than previously described, which has consequences for diagnostic reliability.

They have in particular demonstrated nine novel complete HDV sequences (three originating from Yakutia and six originating from Africa), which are also being passed around in the Ile de France region and which do not belong to any of the known genotypes.

Analysis of these novel isolates:

confirms the existence of a much greater variability of HDV than that described to date, calls into question the classifying of the HDVs in only three genotypes, has led the inventors to propose a PCR-RFLP algorithm based on a partial region of the genome for HDV genotyping and has led the inventors to develop reagents suitable for reliable diagnosis of HDV infections, whatever the genotype, whereas previously, many falsely negative results were observed (existence of new genotypes).

The inventors have therefore given themselves the aim of providing HDV nucleic acid molecules capable of allowing the detection of a variant HDV with respect to the three genotypes previously described.

The subject of the present invention is therefore isolated nucleic acid molecules, characterized in that they are selected from the group consisting of:

the genome of an HDV, which in molecular terms exhibits, over its entire genome, a genetic divergence or distance $\geq 20\%$ (less than 80% similarity) with respect to the sequences of an HDV genotype I, of an HDV genotype II or of an HDV genotype III, the genome of an HDV, which in molecular terms exhibits a genetic divergence or distance $\geq 25\%$ (less than 75% similarity), over a region referred to as R0, delimited by positions 889 to 1289 of the HDV genome, with respect to the corresponding R0 sequences of an HDV genotype I, of an HDV genotype II or of an HDV genotype III, the complete genomes of the HDV isolates or variants referred to as dFr45, dFr47, dFr73, dFr910, dFr48 and dFr644, which exhibit, respectively, the sequences SEQ ID NOS: 1, 6, 11, 16, 21 and 26, and the genome of an HDV which exhibits a genetic divergence or distance $\leq 15\%$ with at least one of the sequences SEQ ID NOS: 1, 6, 11, 16, 21 and 26.

According to an advantageous embodiment of said molecules, the R0 region is preferably obtained by amplification of the HDV RNA with the primers 900S (SEQ ID NO: 33) and 1280AS (SEQ ID NO: 34).

For the purpose of the present invention, the term "nucleic acid molecule" is intended to mean a cDNA or RNA molecule exhibiting one of the HDV genomic sequences as defined above and the sense and antisense sequences complementary thereto.

A subject of the present invention is also nucleic acid molecules which comprise at least one of the fragments of the sequences of a variant HDV as defined above, selected from the group consisting of:

a) the R0 fragments of the following isolated variant HDVs: dFr45, dFr47, dFr48, dFr69, dFr73, dFr644, dFr910, dFr1843, dFr1953, dFr2020 and dFr2066 which exhibit, respectively, the following sequences: SEQ ID NO: 48 to SEQ ID NO: 58, b) the R1 fragment which extends from position 307 to position 1289 of the HDV genome, c) the R2 fragment which extends from position 889 to position 328 of the HDV genome, d) the R3 fragment which extends from position 1486 to position 452 of the HDV genome, e) the R'1 fragment which extends from position 305 to position 1161 of the HDV genome, f) the R'2 fragment which extends from position 984 to position 331 of the HDV genome, g) the R644 fragment which extends from position 889 to position 446 of the HDV genome, h) the G910 fragment which extends from position 1206 to position 929 of the HDV genome, i) the p910 fragment which extends from position 553 to position 1550 of the HDV genome, j) the cDNAs encoding the sHD protein, of sequences SEQ ID NOS: 4, 9, 14, 19, 24 and 29, k) the cDNAs encoding the LHD protein, of sequences SEQ ID NOS: 2, 7, 12, 17, 22 and 27, and l) the primers of sequence SEQ ID NO: 33 to SEQ ID NO: 47.

For the purposes of the present invention, the positions of the fragments in the HDV genome are indicated on the circular genome in genomic orientation, according to the numbering of Wang et al., 1986 or 1987.

The invention also encompasses nucleotide fragments complementary to the above, and also fragments which have been modified with respect to the above, by deletion or addition of nucleotides in a proportion of approximately 15% with respect to the length of the above fragments and/or modified in terms of the nature of the nucleotides, provided that the modified nucleotide fragments conserve an ability to hybridize with the genomic or antigenomic RNA sequences of the isolates as defined above.

In fact, these various viral strains, in the same patient, at a given time, show a heterogeneous population of HDV RNA molecules; in addition, in the course of a chronic infection, in addition to the heterogeneities observed at the editing site (position 1012), mutations may appear. Viral sequences appear to evolve within viral populations with a variable substitution rate of $3 \times 10^{-2}$ to $3 \times 10^{-3}$ per nucleotide and per year.

Some of these fragments are specific and are used as probes or as primers; they hybridize specifically to a variant HDV strain as defined above or to a related strain; the expression "HDV related to a variant as defined above" is intended to mean an HDV exhibiting a genetic divergence $\leq 15\%$.

Such fragments are used for the detection and the epidemiological monitoring of HDV infections. For example, the R0 fragment is used for the detection (RT-PCR) and the genotyping (PCR-RFLP) of HDV. The other fragments which cover the entire HDV genome are used for the molecular characterization of the variant HDVs; phylogenetic analysis of the complete sequence of the genome or of fragments thereof corresponding in particular to R0 or to R2 make it possible to link the profiles observed by PCR-RFLP to a given genotype or to characterize new genotypes.

Consequently, a subject of the present invention is also a method for detection of a variant HDV according to the invention, by hybridization and/or amplification, carried out from a biological sample, which method is characterized in that it comprises:

(1) a step consisting in extracting the nucleic acid to be detected, belonging to the genome of the virus possibly present in the biological sample, (2) carrying out at least one gene amplification using a pair of primers selected from the group consisting of the primers capable of amplifying one of the following regions of the HDV genomic RNA: R0, R1, R2, R3, R644, G910, p910, R'1 and R'2, and (3) analyzing the amplified product by comparison with one of the molecules of sequences SEQ ID NOS: 1, 6, 11, 16, 21 and 26, corresponding respectively to the complete genomes of the isolates or variants referred to as dFr45, dFr47, dFr73, dFr910, dFr48 and dFr644.

Advantageously, the analytical step (3) can be carried out by restriction, sequencing or hybridization; in the latter case, the probe used (in particular in DNA chips) would advantageously be a fragment of 15 to 20 nucleotides, specific for said amplified fragments.

According to an advantageous embodiment of said method, the specific primers for amplifying the regions R0, R1, R2, R3, R644, G910, p910, R'1 and R'2, used in step (2), are selected from the group consisting of:

the primers 900S (SEQ ID NO:33) and 1280AS (SEQ ID NO:34), for the amplification of R0 (approximately 400 pb), the primers 320S (SEQ ID NO:39) and 1280AS (SEQ ID NO:34), for the amplification of the R1 fragment (approximately 960 pb), the primers 900S (SEQ ID NO:33) and 320AS (SEQ ID NO:45), for the amplification of R2 (approximately 1100 pb), which contains the sHD gene corresponding to positions 1598-950, the primers 1480S (SEQ ID NO:46) and 440AS (SEQ ID NO:47), for the amplification of R3 (approximately 650 pb), the primers 900S (SEQ ID NO:33) and 420AS (SEQ ID NO:40), for the amplification of the region R644 (approximately 1250 pb) of the isolate dFr644, the primers 318S (SEQ ID NO:35) and 1150AS (SEQ ID NO:36), for the amplification of R'1 (approximately 850 pb), the primers 960S (SEQ ID NO:37) and 345AS (SEQ ID NO:38), for the amplification of R'2 (approximately 1050 pb), the primers R910S (SEQ ID NO:41) and R910AS (SEQ ID NO:42), for the amplification of the region G910 (approximately 1400 pb) of the isolate dFr910, the primers S1910R (SEQ ID NO:43) and AS1910R (SEQ ID NO:44), for the amplification of the region p910 (approximately 650 pb) of the isolate dFr910.

A subject of the present invention is also a method for detection and for genotyping of HDV from a biological sample, which method is characterized in that it comprises:

(a) a step consisting in extracting the nucleic acid belonging to the genome of the HDV virus, (b) a step consisting in amplifying the region R0 delimited by position 889 to position 1289 of the HDV genome, (c) a first treatment of the amplified nucleic acid molecules with the SmaI and XhoI restriction enzymes, so as to produce a first set of restriction fragments, and (d) a second treatment of nucleic acid molecules with the SacII restriction enzyme, so as to produce a second set of restriction fragments, (e) the combined analysis of the two sets of restriction fragments produced by RFLP (Restriction Fragment Length Polymorphism), so as to detect the presence and/or to determine the type of HDV present in said biological sample.

According to an advantageous embodiment of said method, the amplification step (b) is advantageously carried out with the primers 900S (SEQ ID NO:33) and 1280AS (SEQ ID NO:34).

The method according to the invention makes it possible to define new restriction profiles and to classify the HDVs into seven distinct genotypes.

According to another advantageous embodiment of said method, it also comprises:

(f) amplification of the nucleic acid molecules of said sample by RT-PCR with the primers 900S (SEQ ID NO:33) and 320AS (SEQ ID NO:45), so as to amplify the R2 region, and (g) direct sequencing of the amplified R2 region and comparison with one of the RNA molecules of sequences SEQ ID NOS: 1, 6, 11, 16, 21 and 26, corresponding respectively to the complete genomes of the isolates or variants referred to, respectively, as dFr45, dFr47, dFr73, dFr910, dFr48 and dFr644, for example by phylogenetic analysis.

When unusual profiles are observed, this additional step makes it possible to characterize new genotypes. Specifically, these analyses complementary to the PCR-RFLP make it possible to link the new profile observed to a given genotype, or to characterize a new genotype, by phylogenetic analysis.

A subject of the present invention is also a recombinant vector, in particular a plasmid, comprising an insert consisting of a nucleic acid molecule as defined above.

A subject of the present invention is also a cell transformed with a nucleic acid molecule as defined above.

A subject of the present invention is also translation products encoded by one of the RNA molecules of sequences SEQ ID NOS: 1, 6, 11, 16, 21 and 26 corresponding respectively to the complete genomic RNAs of the isolates or variants referred to, respectively, as dFr45, dFr47, dFr73, dFr910, dFr48 and dFr644, or by the sense or antisense sequences complementary thereto.

A subject of the present invention is also the proteins encoded by the genome of a variant HDV as defined above.

According to an advantageous embodiment of the invention, said protein is selected from the group consisting of:

the LHD protein of dFr45, dFr47, dFr73, dFr910, dFr48 and dFr644 which exhibit, respectively, the sequences SEQ ID NOS: 3, 8, 13, 18, 23 and 28, and the sHD protein of dFr45, dFr47, dFr73, dFr910, dFr48 and dFr644 which exhibit, respectively, the sequences SEQ ID NOS: 5, 10, 15, 20, 25 and 30.

A subject of the present invention is also a peptide characterized in that it consists of a fragment of a protein as defined above, selected from the group consisting of:

peptide A consisting of the 19 amino acids of the carboxy-terminal end of the sequences SEQ ID NOS:3, 8, 13, 18, 23 and 28, peptide B of sequence (one-letter code) RLPLLECTPQ (SEQ ID NO:59) consisting of the 10 amino acids of the carboxy-terminal end of the sequences SEQ ID NOS:3, 8, 13, 18, 23 and 28, and peptide C consisting of the 9 amino acids preceding the sequence SEQ ID NO:59 (SEQ ID NO:60 to SEQ ID NO:65).

Such peptides are useful for the indirect diagnosis (serology) of an HDV infection, in particular by an immunoenzymatic method (ELISA):

peptide B, which is conserved, makes it possible to detect all the variants according to the invention and HDV genotype II, and peptide C is specific for the various HDV variants according to the invention.

A subject of the present invention is also the use of a nucleic acid molecule as defined above or of a protein as defined above, for preparing a kit for detecting and genotyping an HDV.

Besides the above arrangements, the invention also comprises other arrangements which will emerge from the following description, which refers to examples of implementation of the present invention and also to the attached drawings in which:

FIG. 1 represents the phylogenetic tree of the R0 region, obtained by the neighbor-joining method. The numbers in italics indicate the bootstrapping values (BVs) on $10^4$ re-samplings and the sign π indicates the BVs<50%. The scale represents the number of nucleotide substitutions per site.

Figure 2:
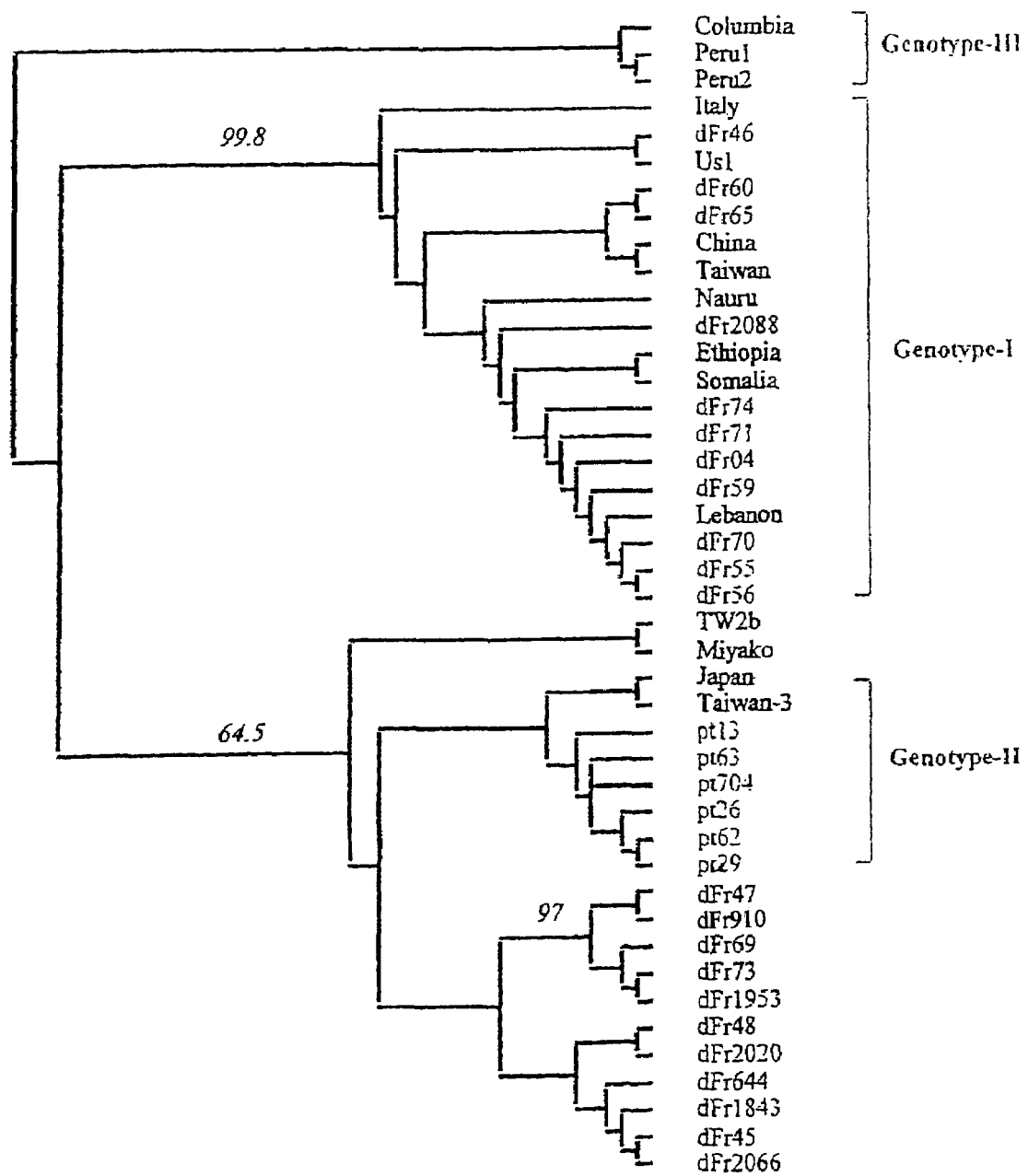
Figure 4:
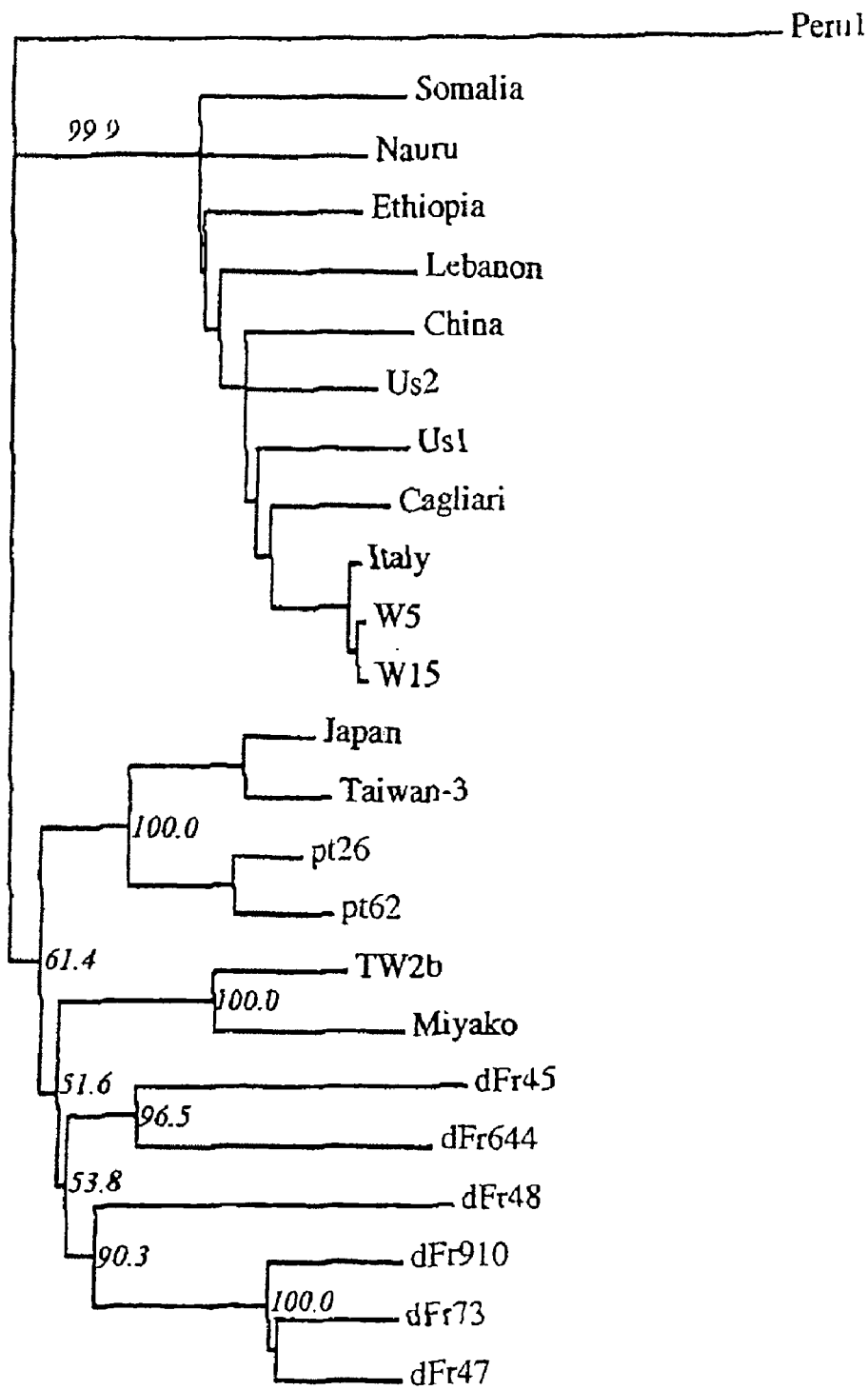

FIG. 2 represents the phylogenetic tree of the R0 regions of HDV, obtained by the maximum parsimony method. The Peru1, Peru2 and Columbia isolates are chosen as "outgroup". The figures in italics indicate the bootstrapping values (BVs) on $10^4$ re-samplings, FIG. 3 illustrates the clinical data from each of the six patients infected with the HDV isolates of African origin. * indicates, respectively, the 6S/6As PCR and R0 PCR, FIG. 4 represents the phylogenetic tree of the complete genomes of HDV, obtained by the neighbor-joining method. The numbers in italics, at each node, indicate bootstrapping values (BVs) on $10^4$ re-samplings. The scale represents the number of nucleotide substitutions per site.

Figure 5:
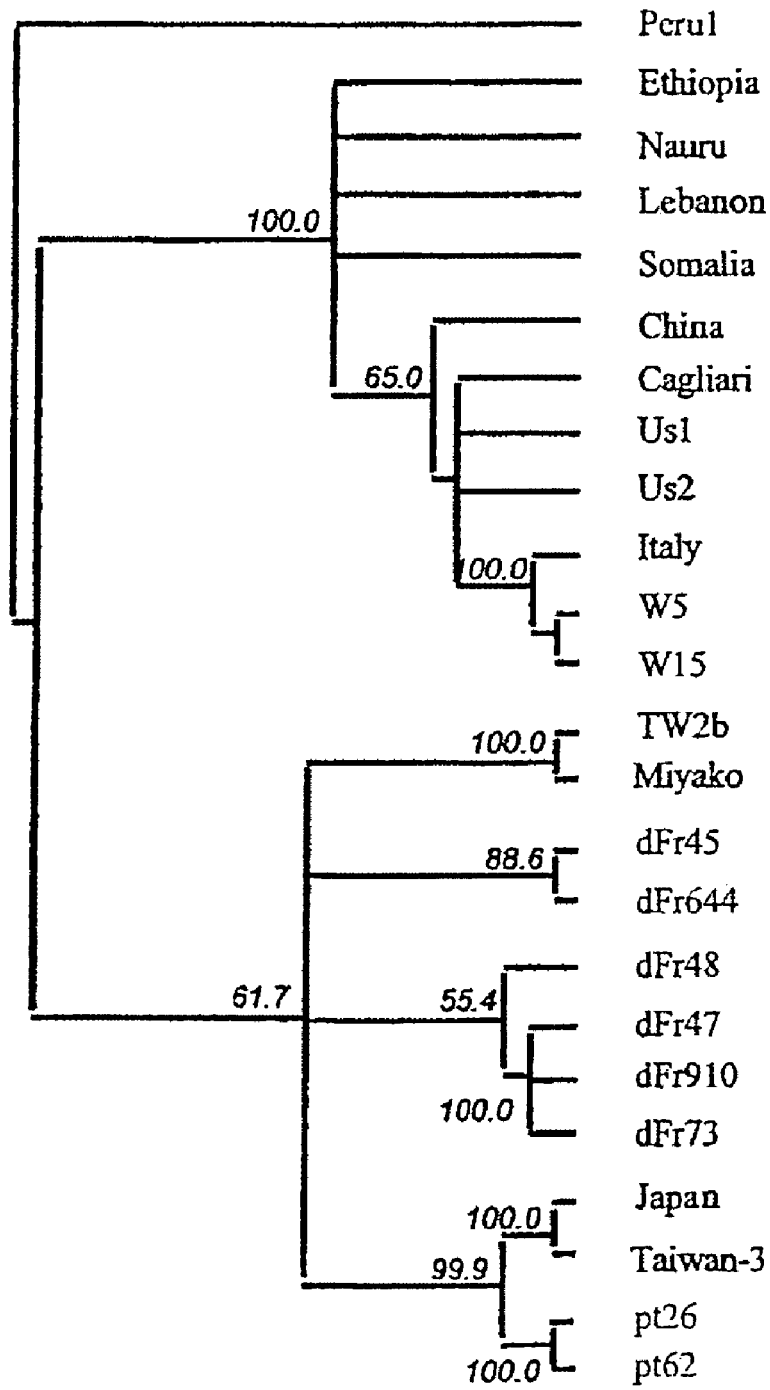

FIG. 5 represents the phylogenetic tree of the complete genomes of HDV, obtained by the maximum parsimony method. The numbers in italics, at each node, indicate the bootstrapping values (BVs) on $10^4$ re-samplings, FIG. 6 represents alignment of the amino acid sequences of the delta proteins of the six isolates of African origin (lines 7, 8, 9, 10, 11 and 12-SEQ ID NOS:74-79) with the known sequences of genotype I (lines 13, 14 and 15-SEQ ID NOS:80-82), genotype II (lines 3, 4, 5 and 6-SEQ ID NOS:70-73), genotype III (line 16-SEQ ID NO:83) and TW2b/Miyako (lines 1 and 2SEQ ID NOS:68-69), using the Clustal program (version 1.8). The amino acid at position 196 of the p27 protein corresponds to the termination codon of the p24 protein (Z) or to the tryptophan codon (W) which results in the synthesis of the p27 protein which extends from amino acids 1 to 215.

It should be clearly understood, however, that these examples are given only by way of illustration of the subject of the invention, of which they in no way constitute a limitation.

EXAMPLE 1

Materials and Methods

1—Patients and Samples 22 sera originating from individuals monitored in various hospital centers of the parisian region were analyzed. The patients were chronic HBs-Ag carriers. Diagnosis of the delta infection was performed by searching for serological markers (HD-Ag, IgM- and IgG-type anti-HD-Ag) and detection of the HDV viral genome by RT-PCR. HD-Ag was not detected in any of the sera analyzed. IgM-type anti-HD-Ag antibodies, reflecting the chronic nature of the delta infection, and IgG-type antibodies were found in all the patients. The entire HDV genome was characterized in six of the patients. All the sera were conserved at −80° C. until extraction of the viral RNA.

2—HDV RNA Extraction

To extract the HDV RNA, a 250 µl volume of serum was added to 75 µl of TRIzol LS Reagent (Gibco BRL, Life Technologies). After homogenization for 30 seconds, the mixture was incubated for 5 min at ambient temperature. Lipid extraction was carried out by adding 200 µl of chloroform cooled to +4° C. After a further homogenization with a vortex, the tubes were incubated and then centrifuged at 14 000 rpm for 10 min at +4° C. The aqueous phase was transferred into extraction tubes and the RNAs were precipitated with 500 µl of cold isopropanol, in the presence of 1 µg of glycogen. After homogenization for 15 min, the samples were centrifuged at 14 000 rpm for 10 min at +4° C. After rinsing with 70% ethanol, the tubes were again centrifuged at 14 000 rpm for 10 min at +4° C. The pellets were dried under a hood at ambient temperature, and then taken up in 100 µl of sterile water comprising a ribonuclease inhibitor (RNasin, Promega). At this stage, precautions were taken to avoid possible contamination of the buffers and of the samples with ribonucleases.

3—Synthesis of a Complementary DNA (cDNA)

This step consists in synthesizing a DNA strand complementary to the HDV RNA by reverse transcription.

In order to eliminate the secondary structure of the HDV RNA, 5 µl of previously extracted RNA were added to a reaction mixture containing 5 µl (or 0.5 pmol) of deoxynucleotide triphosphates (dNTPs) and 1 µl (0.4 pmol) of random hexanucleotides. The RNAs were then denatured for 3 min at 95° C. In order to fix the denatured RNAs, the tubes were immediately frozen in ethanol cooled to −20° C. Ten µl of a reaction mixture, containing 2.5 µl of dithiothreitol (DTT), 100 units (U) of Superscript II reverse transcriptase (Gibco BRL, Life Technologies) and its reaction buffer and also 20 U of ribonuclease inhibitor (RNasin, Promega) were added to the denatured RNA. The reverse transcripion reaction was carried out at 42° C. for 45 min and then stopped by incubation at 94° C. for 5 min. The cDNAs were then conserved at −80° C.

4—Gene Amplification

The cDNA amplification is carried out, exponentially, by PCR (Polymerase Chain Reaction). Two types of polymerases were used: AmpliTaq Gold polymerase (Thermophilus aquaticus) (PE Applied Biosystems) and Pwo polymerase (*Pyrococcus woesi*) or the Expand™ High Fidelity PCR system (Roche).

The amplification was carried out using 5 µl of cDNA, which are added to a PCR reaction mixture containing: 0.25 pmol/µl of sense and antisense primer (Table III), 200 µmol of each dNTP, 1.5 mM of $MgCl_2$, 1 U of AmpliTaq Gold or 2.6 U of Expand™ polymerase in the presence of the corresponding PCR buffers. The PCR reaction was carried out in a thermocycler (PCR Sprint, Hybaid, Coger), according to the following protocol: denaturation of the cDNA—RNA hybrids at 94° C. for 9 min, followed by 40 successive cycles, each comprising denaturation of the DNAs at 94° C. for 45 sec, hybridization of primers (900S/1280As or 6S/6As) at 58° C. for 30 sec, synthesis of the complementary strand, using the polymerase, by elongation at 72° C. for 45 sec. Finally, a final elongation at 72° C. for 4 min 30 sec at 72° C.

TABLE III

Sequences of the primers used for the PCR reactions and their position on the HDV genome

| Primers | 5' → 3' sequence | identification number | positions * |
|---|---|---|---|
| 6S | gaggaaagaaggacgcgagacgcaa | SEQ ID NO:31 | 904-929 |
| 6AS | accccctcgaaggtggatcga | SEQ ID NO:32 | 1141-1121 |
| 900S | catgccgacccgaagaggaaag | SEQ ID NO:33 | 889-911 |
| 1280AS | gaaggaaggccctcgagaacaaga | SEQ ID NO:34 | 1289-1265 |
| 318S | ctccagaggacccttcagcgaac | SEQ ID NO:35 | 305-328 |
| 1150AS | cccgcgggttggggatgtgaaccc | SEQ ID NO:36 | 1161-1138 |
| 960S | gtacactcgaggagtggaaggcg | SEQ ID NO:37 | 962-984 |
| 345AS | tctgttcgctgaaggggtcct | SEQ ID NO:38 | 331-311 |
| 320S | ccagaggacccttcagcgaac | SEQ ID NO:39 | 307-328 |
| 420AS | aacaccctcctgctagcccc | SEQ ID NO:40 | 446-427 |
| R910S | ccggagttcctcttcctcctcc | SEQ ID NO:41 | 1206-1227 |
| R910AS | gttcgcgtccgagtccttettte | SEQ ID NO:42 | 929-907 |
| S1910R | gagctttcttcgattcggac | SEQ ID NO:43 | 1531-1550 |
| AS1910R | gactggtcccctcatgttcc | SEQ ID NO:44 | 572-553 |

* According to the numbering of Wang et al. (Nature, 1986, 323, 508-514; Nature, 1987, 328, 456)

4.1—Strategy for Amplifying the HDV Viral Genome

The pair of primers 6S and 6AS makes it possible to amplify a DNA fragment corresponding to the carboxy-terminal end of the gene encoding the delta antigen.

The R0 region comprising the carboxy-terminal end of the gene encoding the HD-Ag and a portion of the noncoding region was amplified for all the samples using the primers 900S (SEQ ID NO:33) and 1280AS (SEQ ID NO:34). The primer 900S used had 7 nucleotides deleted at the 5' end, compared to that used by Casey et al., 1993a, mentioned above for the classification of the HDV genotypes.

The selection of these primers makes it possible, surprisingly, to amplify a fragment which makes it possible to distinguish the known genotypes (I, II and III) from new genotypes.

The complete sequences of the HDV viral genome of four samples (dFr45, dFr47, dFr48 and dFr73) were obtained by amplification of two overlapping regions R'1 (850 bases) and R'2 (1050 bases), respectively, using the pairs of primers 318S/1150AS and 960S/345AS. For the dFr644 sample, the variability observed in the region corresponding to the primers described above led to the 644 region (R644) being amplified using a specific pair of primers: 900S and 480AS.

For the dFr910 sample, the R0 nucleotide sequence made it possible to define new primers specific for the sample in order to amplify the complete genome. Two pairs of primers were chosen: the primers R910S and R910AS, which amplify a 1400 base fragment corresponding to the G910 region. Another pair of primers, S 1910R and AS 1910R, which amplify a 650 base fragment (p910 region), was essential for covering the entire genome.

The amplification of the various regions (R1, R2, R3, R644, R'1, R'2, G910 and p910) was carried out as described above. The hybridization and elongation temperatures and also the elongation time used for each of the PCRs are indicated in Table IV.

TABLE IV

Amplification of the various fragments of the genome

| Amplified regions | Fragment size (bases) | Hybridization temperature (° C.) | Elongation temperature (° C.) | Elongation time |
|---|---|---|---|---|
| R1 | 960 | 62 | 72 | 1 min 15 s |
| R2 | 1100 | 56 | 72 | 1 min 30 s |
| R3 | 650 | 50 | 72 | 1 min |
| R644 | 1250 | 58 | 72 | 40 s |
| G910 | 1400 | 58 | 72 | 1 min 40 s |
| p910 | 650 | 58 | 72 | 1 min |
| R'1 | 850 | 63 | 72 | 1 min |
| R'2 | 1050 | 60 | 72 | 1 min 20 s |

5—Analysis of the Amplification Products

An 8 µl volume of the PCR product was loaded, in the presence of 2 µl of loading solution, onto a 1.3% agarose gel prepared in 0.5× Tris-borate/EDTA buffer containing 0.5 µg/ml of ethidium bromide (ETB). Electrophoresis was carried out in 0.5× TBE buffer. The migration was carried out in the presence of a size marker (Raoul™, Appligene). The amplified fragment was visualized under ultraviolet rays at 312 nm and photographed.

6—Cloning and Sequencing of the HDV Genomes

Before the cloning and sequencing step, the amplification products are purified in order to remove all traces of salts and enzymes.

6.1—Elongation with Standard Taq Polymerase

This step is performed when the amplification of the product has been carried out with Pwo polymerase. It makes it possible to add deoxyadenosine (A) residues to the 3' ends of the PCR products, due to the fact that Pwo polymerase, which has 5'→3' exonuclease activity, decreases the incorporation of the deoxyadenosines.

A 10 µl volume of purified DNA was added to a 70 µl reaction mixture containing: 0.2 mM of dNTP, 1.5 mM of MgCl$_2$, 1× buffer and 2.5 U of Taq polymerase (Perkin Elmer). The elongation was carried out at 72° C. for 30 minutes. The PCR products then underwent further purification with phenol-chloroform and precipitation with ethanol, and were then taken up in 10 µl of sterile water.

6.2—Cloning in the pCRII-TA-Cloning Vector (Invitrogen)

Cloning is used to confirm the nucleotide sequence of the amplified DNA. It is carried out using the pCRII vector (Invitrogen).

The pCRII vector is in linear form. It has deoxythymidine (T) residues which allow the amplified product to be cloned by virtue of the complementary deoxyadenosine (A) residues added by the Taq polymerase. It also has the Sp6 and T7 promoter sequences, two EcoRI restriction sites which border the site for insertion of the PCR product, and the ampicillin resistance and kanamycin resistance genes. A fraction of the lacZα gene, encoding β-galactosidase, facilitates the selection of the recombinants by virtue of the color of the colonies. Specifically, the plasmids which have integrated the insert do not express the lacZα gene. The bacterial colonies are then white in the presence of β-galactosidase substrate (X-Gal or 5-bromo-4-chloro-3-indolyl-β-galactoside, Roche) and of an inducer of the gene (IPTG or isopropyl-thio-β-D-galactoside, Roche). Thus, the recombinant bacteria are selected by virtue of their ampicillin resistance and of a blue-white screen.

The chosen insert/vector molecular ratio is 3/1 and the volume of PCR product used is variable, depending on the amount of DNA estimated by agarose gel electrophoresis as described above. The 10 µl reaction mixture contains 50 ng of pCRII vector, the corresponding amount of insert, 4 U of T4 DNA ligase, and the 1× ligase buffer. The ligation reaction is carried out for 18 hours at 14° C. The tubes are then conserved at +4° C.

*Escherichia coli* TOP10F' bacteria (Invitrogen), made competent by treatment with calcium chloride are conserved at −80° C., ready for use. A 50 µl volume of competent bacteria is brought into contact with 3 µl of the ligation solution for 30 minutes, in ice. A heat shock (30 sec at 42° C.) causes the plasmid DNA to penetrate into the bacteria, which are immediately placed on ice again for a few minutes, before being incubated for 1 hour at 37° C. in 250 µl of SOC medium (2% tryptone; 10 mM NaCl; 2.5 mM KCl; 10 mM MgCl$_2$; 20 mM glucose, 5 g/l yeast extract). The colonies are then isolated on Petri dishes containing LB agar (Luria-Bertani medium), supplemented with ampicillin (50 µl/ml), and 40 µl of X-Gal (40 mg/ml) and 40 µl of IPTG (100 mM) are distributed.

6.3—Plasmid Extraction and Insert Analysis

The white colonies are seeded in LB broth-ampicillin (50 µl/ml) and incubated for 18 hours at 37° C., with shaking. A blue colony, i.e. a colony which has not inserted a fragment, is selected as a negative control for ligation.

The plasmid extraction is carried out using a commercial QIAprep® Spin Miniprep kit (Qiagen). Briefly, after centrifugation (3000 rpm at +4° C.) and removal of the supernatant, the bacterial pellet is suspended in 250 µl of buffer (50 mM Tris-HCl, pH 8, 10 mM EDTA, 100 µl/ml RNase A) and lysed by adding 250 µl of alkali buffer (200 mM NaOH, 1% SDS). After homogenization for 5 min, 350 µl of buffer (3M potassium acetate, pH 5.5) are added. The supernatant containing the plasmid DNA is then transferred into a QIAprep column. A centrifugation eliminates the eluate into the collecting tube.

The column is washed with an ethanol buffer and dried, and the DNA is then eluted in 50 µl of sterile water.

To verify the insertion of the fragment of interest, the plasmid is then digested with the EcoRI restriction enzyme. The digestion is carried out in a 30 µl reaction mixture containing: 2 µl of the plasmid solution, 10 U of EcoRI enzyme (Appligene) and 1× reaction buffer. The digestion lasts 2 hours at 37° C. and the result is visualized by agarose gel electrophoresis.

6.4—Sequencing by the BigDye Terminator Method

The sequencing is carried out on the PCR products purified beforehand on Microcon 50 columns (Amicon) or on the plasmid DNA. The fragments are either sequenced directly with the PCR primers (R0 fragment sequenced with the primers 900S and 1280AS), or after cloning in the PCRII vector using universal primers (Sp6 and T7).

Two different clones were selected for each of the amplified regions, in order to remove any possible ambiguities during reading of the nucleotide sequences.

The sequencing was carried out using the BigDye Terminator reagent (PE, Applied Biosystems). The sequencing principle consists of vertical electrophoresis, in a polyacrylamide gel, of the DNA labeled with four different fluorochromes. The DNA matrices are loaded onto the gel and separated according to their size, before subjecting the gel to a laser beam continuously. The laser excites the fluorochromes, which each emit at a different wavelength, detected by a spectrograph. Computer software, coupled to the sequencer, enables automatic analysis and conversion of the data to nucleotide sequences.

The 10 µl reaction mixture comprises: 4 µl of the labeling solution (deoxynucleoside triphosphates (dATP, dCTP, dGTP, dUTP), AmpliTaq DNA polymerase, MgCl$_2$, Tris-HCl buffer pH 9), 20 pmol of primer (sense or antisense) and 500 ng of plasmid purified on Centricon columns. The (sense and antisense) sequence reactions are carried out in a Perkin 9600 thermocycler, with 25 cycles (96° C. for 10 sec; 50° C. for 5 sec; 60° C. for 4 min). The products are then precipitated in 40 µl of 70% ethanol, loaded onto gel and analyzed using an automatic sequencer of the ABI PRISM 377 type.

The crude sequences obtained are in the form of electrophoregrams. The sequences are validated and exploited using the Sequence Navigator program (PE, Applied Biosystems). They are the subject of at least one double reading, with two different sequencing primers (sense and antisense), in order to minimize errors.

These sequences are then directly captured on a computer using the DNA Strider 1.3 software for rapid sequence analysis.

7—Computer Analysis of the Nucleotide and Protein Sequences

The read and corrected sequences are compared and subjected to the various phylogenetic algorithms.

The sequences obtained (22 sequences) were compared to 21 complete genomic sequences of HDV available in GenBank (Table V).

TABLE V

Accession numbers of the various isolates

| | Accession number (GenBank) | Isolate name | Geographical origin |
|---|---|---|---|
| 1 | X04451 | Italy 1 (A20) | Italy |
| 2 | M84917 | Lebanon I | Lebanon |
| 3 | X85253 | PatientA. | Cagliari (Italy) |
| 4 | X60193 | Jul. 18, 1983 (patient s) | (patient S) Japan |
| 5 | M92448 | Taiwan | Taiwan |
| 6 | L22061 | Columbia | Columbia |
| 7 | X77627 | Chinese human serum | Central China |
| 8 | L22064 | Peru-2 | Peru |
| 9 | L22063 | Peru-1 | Peru |
| 10 | L22066 | US-2 | United States |
| 11 | M58629 | Nauru | Island of Nauru |
| 12 | U81988 | Somalia | Somalia |
| 13 | U81989 | Ethiopia 1 | Ethiopia |
| 14 | AF098261 | Canada | Canada (Quebec) |
| 15 | U19598 | Taiwan 3 | Taiwan |
| 16 | AF018077 | TW2b | Taiwan |
| 17 | L22062 | Japan 3 | Japan |
| 18 | AF309420 | Miyako | Island of Miyako (Okinawa, Japan) |
| 19 | D01075 | US-1 | United States |
| 20 | M21012 | W15 | Experimental transmission (marmot) |
| 21 | AJ307077 | W5 | Experimental transmission (marmot) |
| 22 | AJ309868 to AJ309881 | Yakutia isolates | Yakutia (Russia) |

The first step consists overall in aligning the sequences of interest with the reference HDV sequences described and listed in the databank (Genbank), using the CLUSTAL W1.8 program (Thompson et al., N.A.R., 1994, 22, 4673-4680). Minor manual corrections were sometimes necessary using the SeqPup program in order to optimize the alignment.

Two approaches were followed: the use of protein alignment for the HD gene and the study of the stability of the aligned positions using an appropriate alignment program.

Based on this nucleotide sequence alignment, phylogenetic trees are constructed using various algorithms. The analyses are based on the distance matrices (phenetic approach), calculations of maximum parsimony (MP; cladistic approach) and calculations of maximum likelihood (ML; statistical approach).

Phenetic Approach (Genetic Distance)

The principle of this method is to find pairs of neighboring sequences, minimizing the total length of the branches of the tree. This approach makes it possible to reconstruct a phylogeny on the basis of calculating the overall similarity between the sequences compared two by two, which is expressed by virtue of a distance. It is a method which makes it possible to convert the sequence data into numerical values of distances, arranged in a matrix. The topology of the tree is constructed so as to group together the sequences which have most characters in common using one of the grouping methods such as the neighbor-joining method (Saitou et al., 1987).

Cladistic Approach (Maximum Parsimony)

The principle of this method consists in establishing whether sequences are related by searching for shared nucleotide bases, minimizing genetic events. The maximum parsimony algorithm constructs a phylogenetic tree in such a way that it involves a minimum of mutations. The tree selected is that which requires the least change. This method is sensitive to the differences in degree of mutation along the branches. The "clades" or "monophyletic groups" consist of the groups of sequences sharing a common ancestor, excluding any other sequence.

Statistical Approach

The maximum likelihood method is considered to be a statistical approach. The program calculates the probability that a sequence will evolve toward another over time. In other words, it consists in considering the changes at each site or character as independent probability events. This likelihood algorithm is cumulative over all the sites, and the sum is maximized in order to estimate the branch length of the tree. This method requires a long calculation period in order to search for the most likely phylogenetic tree corresponding to the sequences observed, due to the fact that it takes into account the probability of change of each character.

All the phylogenetic analyses were carried out using the Phylip 3.75 (PHY Logenetic Inference Package) (Felsenstein et al., 1989) and Paup * version 4.0beta6 (Phylogenetic Analysis Using Parsimony)(Swofford et al., 1998) computer programs.

The distance analysis was calculated by the two-parameter Kimura method, which considers the transition rate (mutations T<->C and G<->A) at each site and the transversion rate (mutations "A or G"<-->"T or C") at each site to be different.

The reliability and the robustness of the sequence groups (or of the topologies) are evaluated statistically by the resampling (or bootstrap) approach on $10^3$ and $10^4$ resamplings.

The results obtained are in the form of a phylogenetic tree visualized using the Treeview program (version 1.6.5), proposing various presentations of the tree (cladogram, radial and phylogram). It also makes it possible to visualize the bootstrap values at each node and to determine a taxon as an outgroup (sequences of genotype III).

Translation of the delta gene to amino acids is carried out using the DNAStrider version 1.3 program. The protein sequence alignment is carried out as described above.

8—Genotypic Analysis of HDV by Restriction Polymorphism (RFLP)

The HDV is genotyped by PCR-RFLP of the R0 region, according to the following steps:

Step 1: The PCR products are digested with the two restriction enzymes SmaI and XhoI (New England Biolabs): 10 µl of amplified product are digested separately in two tubes with 5 U of SmaI or XhoI enzyme, respectively at 30° C. and at 37° C., for 3 hours in a final volume of 50 µl in the presence of the appropriate buffer and of sterile water. The digestion products are visualized under ultraviolet rays as described above and the fragment sizes are determined by comparison with a size marker (50 pb DNA ladder, or the V and VI. markers, Life Technologies GibcoBRL).

Step 2: The samples exhibiting a profile other than the genotype I profile are digested with another enzyme, SacII (New England Biolabs), for 3 hours at 37° C. and the digestion products are visualized as in step 1.

Step 3: The genotype of the virus is determined based on analysis of the combination of the SmaI, XhoI and SacI restriction profiles.

9—Algorithm for Genotyping HDV by PCR-RFLP

The algorithm for genotyping HDV by PCR-RFLP comprises at least two steps:

the first consists of cleavage, with two restriction enzymes, SmaI and XhoI, of the R0 fragment amplified by RT-PCR from the RNAs extracted from the sera of the patients;

the second for the patients of "non-I profile", consists of cleavage of R0 with the SacII enzyme;

sequencing of the R0 region or of the region encoding p24 (or, if necessary, of the entire genome), followed by phylogenetic analyses will only be carried out as a backup if unusual restriction profiles are obtained.

EXAMPLE 2

Demonstration of New HDV Genotypes

1—Phylogenetic Analysis of the R0 Region 22 samples from patients infected with HBV and HDV were analyzed. The R0 region was amplified by PCR and the fragment obtained was then sequenced using the primers 900S and 1280AS.

The phylogenetic study was carried out using alignment of 336-base sequences of R0 (the ambiguous regions are eliminated), including therein, in addition to the 22 sequences studied, 15 reference sequences and 6 R0 sequences from Yakutia HDV (Pt13, 26 (SEQ ID NO:66), 29, 62 (SEQ ID NO:67), 63 and 704). The name given to the sequences corresponds to dFr (for "delta France") followed by the patient serum number.

a) Genetic Distance Analysis

The phylogenetic tree obtained by reconstruction using genetic distances of the R0 region is given in FIG. 1.

The topology of the tree individualizes genotypes I and III, represented respectively by seven and three reference nucleotide sequences. The other reference sequences are represented by the type II sequences (Japan, Taiwan-3 and Yakutia sequences), and a group of two sequences (TW2b, Miyako) each described respectively as prototype of "subtypes IIB and IIC".

This tree shows that the viral sequences originating from the 22 samples analyzed correspond to two situations:

11 sequences are affiliated with the genotype I sequences, with the exception of the sequence dFr46, which appears to be related to the sequence US-1 described by Makino (Makino et al., 1987); all these sequences are distributed heterogeneously within genotype I;

the remaining 11 sequences are very far removed from genotype I and from genotype III. In addition, none of these sequences is directly grouped together with the type II sequences (Japan, Taiwan-3, Yakutia 13, 26, 29, 62, 63, 704) or with the (TW2b, Miyako) sequence group; these reference sequences form on their own two distinct groups.

The topology of the tree obtained by reconstruction using the genetic distances of the R0 region shows that the nucleic acid molecules isolated from the various variant HDVs are distributed within four subgroups (FIG. 1):

the dFr644 molecule, which appears to be isolated; it possesses, however, with a group of three molecules (dFr45, dFr2066 and dFr1843), a node which is supported for a bootstrap value of only 66.7%;

on the other hand, the branch which unites the dFr45, dFr2066 and dFr1843 molecules is robust, since it is supported by a bootstrap value (BV) of 99.9%;

a set of five molecules: dFr47, dFr910, dFr69, dFr73 and dFr1953 is supported by a BV of 100% and a pair of molecules dFr48 and dFr2020, which is also supported by a BV of 100%.

b) Maximum Parsimony Analysis

The phylogenetic tree obtained by reconstruction using the maximum parsimony of the R0 region is given in FIG. 2.

The maximum parsimony analysis supports the same topology as the genetic distance analysis. The reconstruction demonstrates the existance, within the 11 variant sequences, of the same three monophyletic groups; for example, with this approach, the group of five molecules dFr47, dFr910, dFr69, dFr73 and dFr1953 is also supported by a BV of 97% (FIG. 2).

The 11 variant molecules, the genotype II molecules and the [TW2b, Miyako] set appear to derive from a common branch which could, by comparison with the genotype I and genotype III sequences, individualize all the genotype II sequences. However, the bootstrap values supporting this branch are relatively moderate: 88.5% by NJ and 64.5% by MP (resampling carried out on $10^4$ samples) compared with those of genotype I (BV=99.8%) and genotype III (BV=100%). In addition, the average distance between the various subgroups defined within the 11 variant HDVs or between these variants and the genotype II sequences appears to be higher than between all the genotype I isolates or within the three molecules defining genotype III.

All these results emphasize the characterization of new HDV genotypes.

2—Phylogenetic Analysis of all the Genomes a) Reconstruction of the Complete Genome from Amplified Fragments In order to study the complete genome of these variants, and with the aim of specifying their affiliation, several regions of the HDV genome were amplified (Table II) from 6 samples including at least one member of each of the 4 subgroups and three representative of the major group were selected: dFr45, dFr47, dFr48, dFr73, dFr644 and dFr910.

More precisely, the following fragments were amplified by PCR (Table IV):

fragments of 850 pb (R'1) and 1050 pb (R'2) overlapping at their ends for dFr45, dFr47, dFr48 and dFr73, two overlapping fragments of 960 bp and of 1250 bp for dFr644, and two fragments of 1400 pb and 650 pb for dFr910.

All these amplified genomic regions were cloned into a vector PCRII™ (Table VI). Two clones corresponding to each of the amplified fragments were sequenced. Reconstruction of complete consensus HDV cDNA sequences was carried out after alignment of the overlapping regions and alignment with the reference sequences.

TABLE VI

| pCRII clones containing the various inserts | | | | |
|---|---|---|---|---|
| | R0 | R'1 | R'2 | G910 | R1 |
| dFr45 | — | dFr45R'1 clone 2 dFr45R'1 clone 4 | dFr45R2 clone 8 dFr45R2 clone 10 | — | — |
| dFr47 | — | dFr47R'1 clone 13 dFr47R'1 clone 16 | dFr47R2 clone 19 dFR47R2 clone 22 | — | — |
| dFr48 | — | dFr48R'1 clone 23 | dFr48R2 clone 19 | — | — |

TABLE VI-continued pCRII clones containing the various inserts

|  | R0 | R'1 | R'2 | G910 | R1 |
|---|---|---|---|---|---|
| dFr73 | — | dFr48R'1 clone 28 dFr73R'1 clone 36 dFr73R'1 clone 39 | dFr48R2 clone 22 dFr73R2 clone 29 dFr48R2 clone 33 | — | — |
| dFr644 | — | — | — | — | 644R1 clone 4 644R1 clone 8 |
| dFr910 | 910R0 clone 4 910R0 clone 4 | | | R910 clone 29 R910 clone 31 | 910R1 clone 4 910R1 clone 5 | b) Analysis of Six New Complete HDV Genomic Sequences of African Origin b$_1$) Clinical Characterization of 6 Patients Five patients originate from West Africa, and one patient has spent time in Cameroon. At the time samples were taken, these patients had been residing in the parisian region for at least two years. All these patients were suffering from severe hepatitis and the clinical data are summarized in FIG. 3.

b$_2$) Genomic Organization of the New HDV Sequences

Comparative analysis of the R0 regions of 22 patients infected with HDV and HBV with those available in the databases demonstrated the great genetic diversity of the HDV viral genome.

The size of the complete genomes is different for the six sequences of the six HDV isolates of African origin, which confirms the variability of HDV:

the viral genome of the dFr910, dFr47 and dFr73 isolates, comprising 1697 nucleotides, is the longest ever described for HDV;

the genome of the dFr45 isolate appears to be among the smallest (1672 nt), and the genomic sequences of the dFr644 and dFr48 viruses are, respectively, 1680 nt and 1687 nt.

The analysis after alignment of the various sequences studied reveals a high degree of conservation in the regions of the HDV genome corresponding to the ribozymes responsible for cleavage of the genomic and antigenomic RNAs. Similarly, the reading frame encoding the delta antigen is found on the antigenomic strand. A tryptophan codon (UGG) is the only one to be characterized for two sequences (dFr47, dFr910), and an ambiguity (G/A) found for the other four sequences indicates that the small delta protein and the large delta protein are very probably synthesized. The variable regions comprise the noncoding portion and also the 5' and 3' ends of the LHD gene. Notably, an insertion of 7 nucleotides exists in the dFr48 sequence. This insertion is present in a loop corresponding to one of the ends of the genome in its pseudo-double-stranded form (at position 797 of the Italy reference sequence (Wang et al., 1987)).

c) Comparison of the Six HDV Sequences of African Origin with the Sequences Representative of the Various Genotypes Comparison of the six new molecules with the known molecules, representative of the three known genotypes, indicates a nucleotide similarity of between 71.7% (dFr45 versus Lebanon) and 80.0% (dFr73 versus Yakutia p26) with regard to the genotype I and II molecules and the TW2b and Miyako molecules. Specifically, for each of the six isolates, the mean nucleotide similarity is of the order of 73.3% to 74.6% with the genotype I molecules, of 74.5% to 78.8% with those of genotype II and of the order of 74.6% to 77.8% with the Tw2b/Miyako molecules. On the other hand, the nucleotide similarity with the Peru isolate (genotype III) is only 63.9% to 66.0%, confirming the particularly distant nature of this molecule (Table VII). In addition, when the six molecules corresponding to these complete genomes and defining the six variants dFr4S, dFr47, dFr48, dFr73, dFr644 and dFr910 are compared with one another, only the group of molecules dFr73, dFr910 and dFr47 exhibits a sequence similarity of the order of 90%. The dFr45, dFr48 and dFr644 molecules are as distant from one another as they are from genotypes I and II, from the TW2b/Miyako sequences and from the group of molecules dFr73, dFr910 and dFr47 (of the order of 73.2% to 78%) (Table VIII).

TABLE VII

Percentage similarity of the complete African HDV sequences with the various known genotypes (calculation of the mean)

| HDV isolate* | Type I | Type II | TW2b/Miyako | Type III |
|---|---|---|---|---|
| dFr45 | 73.3 71.7-74.6 | 74.5 73.2-75.5 | 74.6 | 66 |
| dFr47 | 74.2 73.0-75.0 | 78.6 78.2-79.9 | 77.4 | 65.5 |
| dFr48 | 73.3 72.0-74.0 | 77.1 76.6-77.7 | 75.5 74.4-76.6 | 65.4 |
| dFr73 | 74.1 73.0-75.0 | 78.8 77.7-80.0 | 77.8 77.5-78.0 | 65.9 |
| dFr644 | 73.6 72.2-74.6 | 76.8 76.2-77.2 | 77.0 76.9-77.2 | 63.9 |
| dFr910 | 74.6 73.0-75.8 | 77.9 77.0-78.6 | 77.2 77.0-77.5 | 64.6 |

*The reference HDV isolates correspond to the complete genomes studied in Example 2.1.

TABLE VIII

Percentage similarity of the new HDV molecules with one another

|  | dFr47 | dFr48 | dFr73 | dFr644 | dFr910 |
|---|---|---|---|---|---|
| dFr45 | 74.8 | 73.2 | 75 | 78 | 74.7 |
| dFr47 |  | 77.1 | 90 | 76.3 | 89 |
| dFr48 |  |  | 77.7 | 75.5 | 76.1 |
| dFr73 |  |  |  | 76.3 | 89 |
| dFr644 |  |  |  |  | 76.1 | d) Phylogenetic Analysis of the Six HDV Molecules of African Origin and of the Molecules Representative of the Various Genotypes The phylogenetic analysis was carried out on the six complete sequences of African origin, sixteen reference sequences and two Yakutia sequences (Pt26 and Pt62). FIG. 4 illustrates the results obtained by distance analysis. The phylogenetic tree reconstructed by neighbor joining (NJ) shows that none of the six sequences studied (dFr45, dFr47, dFr48, dFr73, dFr644 and dFr910) is grouped together with the genotype I or genotype III reference sequences. The affiliation of these African sequences with the genotype II sequences (with the TW2b and Miyako sequences described, respectively, as subtypes IIB and IIC) is not supported by high bootstrap values (<70%) (Wu et al., 1998). In addition, the TW2b and Miyako sequences appear to form a distinct and monophyletic group with a BV of 100%. These two sequences appear to constitute on their own a "clade" representing a genotype different from type II.

In the distance analyses, the six African sequences are subdivided into 3 distinct subgroups (supported by BVs of greater than 90.3% for $10^4$ resamplings). The dFr47, dFr73 and dFr910 sequences constitute a group whose branch is based on a bootstrap value of 100%. To support these results, the maximum parsimony study was carried out on the same set of sequences (FIG. 5). By routing the tree artificially using the "Peru-1" sequence, all the sequences of genotype I are individualized (BV=100%), as in all the analyses carried out above. The topology of the other sequences supports distribution of the African and Asian isolates in several groups; this shows the value of using the R0 region. Genotype II groups together the Yakutia, Taiwan-3 and Japan sequences with a BV of 99.9% on $10^4$ resamplings. Similarly, the individualization of TW2b and Miyako is confirmed (BV=100%). Finally, the African sequences indicate the existence of at least 3 subgroups. The monophilicity of the dFr47, dFr73 and dFr910 sequences (BV=100%) supports the affiliation of these sequences in a subgroup. On the other hand, the dFr48 sequence, which possesses, with the isolates of the preceding group (dFr910, dFr47, dFr73), a respective nucleotide similarity of 76.1, 77.1 and 77.7%, is grouped together with these sequences in only 55.4% of resamplings, suggesting its possible individualization. Although appearing to be distant from one another, the dFr45 and dFr644 group is observed with a high BV (NJ=96.5/MP=88.6) in the context studied.

Consequently, the phylogenetic analyses of both the R0 regions and the complete sequences of the African sequences indicate that the groups differ from one another and could constitute three (or even four) distinct genotypes; these results thus demonstrate the existence of at least seven HDV genotypes.

3—Analysis of the Amino Acid (aa) Sequence of the Delta Antigen (HD-Ag)

The HD-Ag is represented by the two forms p24 (sHD) and p27 (LHD) of the delta protein. The protein sequence of 1 to 194-195 amino acids corresponds to the small delta protein (sHD) or p24 form. The large delta protein (LHD) or p27 form has the same amino-terminal end and an extension of 19 to 20 amino acids at its carboxy-terminal end.

The alignment of the sequence of the HD antigen of the six African sequences with the known HD protein sequences is given in FIG. 6.

Analysis of the sequences shows that the six isolates of African origin have an amino acid identity of the order of 69 to 77% with the genotype I sequences, of 71 to 79% with the genotype II isolates, of 72 to 78% with the TW2b/Miyako sequences, and of 63% with the Peru isolate (genotype III).

The size of the proteins corresponding to the new isolates ranges between 213 and 214 amino acids. All these proteins have the same hydrophobicity profile. The p24 form has two small hydrophobic regions, one located in the region of amino acids 50-60 (between the polymerization site and the NLS) and the other between positions 160 and 172 (opposite an extremely conserved unit). Two other domains are well conserved in the various genotypes: they are the RNA-binding domain and the nuclear localization domain. Just like what has been described in the literature, the carboxy-terminal end of the delta protein (between amino acids 195 and 215) constitutes a hypervariable region. Only two amino acids out of the 19-20 are conserved. They are the cysteine (C) corresponding to the farnesylation site of the large form of the HD protein, and the carboxy-terminal glycine (G). In addition, the signature sequences specific for the isolates of the same genotype, for example the 19 amino acids specific for the large protein of genotype I or the 20 amino acids of genotype III, are found.

On the other hand, for the protein sequences of the isolates of African origin, and of the genotype II and TW2b/Miyako isolates, the carboxy-terminal end appears to be subdivided into two domains. The variable domain is represented by amino acids 197 to 205 and the conserved domain ranges from amino acids 206 to 215 (RLPLLECT-PQ)(FIG. 5).

4—Definition of 7 HDV Clades

Analysis of the complete sequences of the six African isolates makes it possible to define seven HDV clades corresponding to the following genotypes (Table IX):

TABLE IX

Clade/genotype correspondance

| Clade | Genotype | Isolate |
|---|---|---|
| 1 | I | Italy, W5, W15, US1, US2, Lebanon, Ethiopia, Somalia, Island of Nauru, China, Cagliari, Canada, etc. |
| 2 | IIA | Japan, Taiwan3, Yakutia26, Yakutia 62 |
| 3 | III | Peru 1 |
| 4 | IIB, IIC | TW2b, Miyako |
| 5 | ? | dFr910, dFr73, dFr47 |
| 6 | ? | dFr48 |
| 7 | ? | dFr45, dFr644 |

EXAMPLE 3

Method for Genotyping HDV-1 to HDV-7 by PCR-RFLP

The genotyping is carried out according to the protocol described in Example 1.8.

1—Lack of Sensitivity of the 6A/6S PCR

Initially, three HB-Ag-positive patients posed a delta infection diagnostic problem. In fact, in these patients, severe hepatitis associated with the presence of anti-HDV IgM is observed, but a lack of HDV replication by RT-PCR using the primers 6A-6S described in Deny et al. (1991, 1993, 1994, mentioned above) for the routine diagnosis of HDV infection. The 6A/6S PCR amplifies 234 pb cDNA fragment corresponding to the carboxy-terminal end portion of the LHD gene (position 904 to position 1141 on the viral genome).

The RNAs extracted from the serum of these same patients were reamplified using the pair of primers 900S and 1280AS defining the R0 region.

The results obtained using the samples from these three patients demonstrated the reproducible presence of a 400 pb band (R0) with the primers 900S and 1280AS, whereas the 6A-6S PCR remained negative.

These results were confirmed on a series of serum samples from patients which were analyzed in parallel with the pairs of primers 6A-6S and 900S-1280AS. Out of 286 samples, 14 were positive only with the R0 PCR.

These results demonstrate greater specificity and better sensitivity of the primers 900S and 1280AS, compared with the primers 6S and 6A, for detecting HDV RNA in the serum of infected patients.

2—Restriction Profiles Expected for HDV-1 to HDV-7

The PCR-RFLP methods conventionally used (Wu et al., 1995a; Wu et al., 1995b; Casey et al., 1996) make it possible to distinguish three different delta genotypes. Use of the SmaI restriction enzyme does not differentiate all the genotypes I, IIA and IIB recognised to date, and the XhoI enzyme was used to differentiate "subtype IIA" from "subtype IIB" (Wu et al., 1995b).

Combining the two enzymes SmaI and XhoI in a first step reveals seven distinct profiles (from P1 to P7) (Table X). These seven profiles do not superimpose exactly on the seven clades (HDV-1 to HDV-7). Consequently, the samples of "non-P1" profile are cleaved in a second step with the SacII enzyme, thus resulting in the obtaining, in a combined manner, of ten distinct delta profiles (from D1 to D10)(Table XI) which can be linked specifically to the various clades described, by virtue of the phylogenetic analyses.

TABLE X

Restriction profiles, cleavage of the R0 region with the SmaI and XhoI enzymes

| STEP 1 Genotypes described | SmaI fragments Size (pb) | SmaI profile | XhoI fragments Size (pb) | XhoI profile | SmaI-XhoI combined profile | |
|---|---|---|---|---|---|---|
| I | 220, 179 | S1 | 383, 16 | X1 | S1 X1 | P1 |
| IIA | 397 | S2 | 303, 78, 16 | X2 | S2 X2 | P2 |
| IIB | 397 | S2 | 319, 79 | X3 | S2 X3 | P3 |
| IIC (Miyako) | 397 | S2 | 157, 162, 79 | X4 | S2 X4 | P4 |
| III | 298, 107 | S3 | 405 | X5 | S3 X5 | P5 |
| II Yakutia | 178, 117, 110 | S4 | 303, 78, 16 | X2 | S4 X2 | P6 |
| dFr45 | 217, 179 | S1 | 303, 78, 16 | X2 | S1 X2 | P7 |
| dFr644 | 217, 179 | S1 | 303, 78, 16 | X2 | S1 X2 | P7 |
| dFr47, 73 910 | 179, 111, 107 | S4 | 303, 78, 16 | X2 | S4 X2 | P6 |
| dFr48 | 397 | S2 | 303, 78, 16 | X2 | S2 X2 | P2 |

TABLE XI

Restriction profiles expected after cleavage of the R0 region with the SmaI, XhoI and SacII enzymes

| STEP 2 Genotypes described | SacII fragments Size (pb) | SacII profile | SmaI-XhoI/SacII combined profile | |
|---|---|---|---|---|
| I | 362, 38 | Sc1 | S1 X1 Sc1 | D1 |
| IIA | 266, 92, 38 | Sc2 | S2 X2 Sc2 | D2 |
| IIB | 268, 130 | Sc3 | S2 X3 Sc3 | D3 |
| IIC (Miyako) | 268, 130 | Sc3 | S2 X4 Sc3 | D4 |
| III | 405 | Sc4 | S3 X5 Sc4 | D5 |
| II Yakutia | 266, 92, 38 | Sc2 | S4 X2 Sc2 | D6 |
| dFr45 | 268, 130 | Sc3 | S1 X2 Sc3 | D7 |
| dFr644 | 397 | Sc4 | S1 X2 Sc4 | D8 |
| dFr47, 73 910 | 268, 130 | Sc3 | S4 X2 Sc3 | D9 |
| dFr48 | 268, 130 | Sc3 | S2 X2 Sc3 | D10 |

3—Genotyping of the Samples from Patients by PCR-RFLP

Based on the PCR-RFLP analysis of samples (more than 50):

no genotype II or III was found.

89.7% of the patients exhibited a D1 profile (genotype I) and 10.3% exhibited a "non-I" profile, two new XhoI profiles (X6 and X7) resulting in three new additional combinations (D11, D12 and D13) were detected (Tables XII and XIII).

TABLE XII

New XhoI restriction profiles obtained from five patients originating from West Africa

| STEP 1 PATIENTS | SmaI fragments Size (pb) | SmaI profile | XhoI fragments Size (pb) | XhoI profile | SmaI-XhoI combined profile | |
|---|---|---|---|---|---|---|
| dFr1843 | 218, 179 | S1 | 303, 78, 16 | X2 | S1 X2 | P7 |
| dFr1953 | 218, 179 | S1 | 303, 78, 16 | X2 | S1 X2 | P7 |
| dFr2020 | 392 | S1 | 303, 73, 16 | X2 | S2 X2 | P2 |
| dFr2088 | 220, 179 | S1 | 242, 171, 16 | X6 | S1 X6 | P8 |
| dFr2066 | 217, 179 | S1 | 237, 66, 16 | X7 | S1 X7 | P9 |

TABLE XIII

New XhoI, SmaI, SacII restriction profiles obtained in five patients originating from West Africa

| STEP 2 PATIENTS | SacII fragments Size (pb) | SacII profile | SmaI-XhoI/SacII combined profile | |
|---|---|---|---|---|
| dFr1843 | 267, 130 | Sc3 | S1 X2 Sc3 | D7 |
| dFr1953 | 267, 92, 38 | Sc2 | S1 X2 Sc2 | D11 |
| dFr2020 | 262, 130 | Sc3 | S2 X2 Sc3 | D10 |
| dFr2088 | 396 | Sc4 | S1 X6 Sc4 | D12 |
| dFr2066 | 396 | Sc4 | S1 X7 Sc4 | D13 |

The correspondance between the combined profiles and the genotypes identified by the phylogenetic analysis is given in Table XIV.

TABLE XIV

Summary of the various results based on the phylogenetic analyses and the various corresponding profiles

| Clades | Genotypes | Isolates | Combined profiles (SmaI-XhoI/SacII) |
|---|---|---|---|
| HDV-1 | I | Italy | D1A |
| | | dFr2088 | D1B |
| HDV-2 | IIA | Japan | D2A |
| | | Yakutia isolates | D2B |
| HDV-3 | III | Peru 1 | D3 |
| HDV-4 | IIB | TW2b | D4A |
| | IIC | Miyako | D4B |
| HDV-5 | V | dFr47, dFr73 and dFr910 | D5A |
| | | dFr1953 | D5B |
| HDV-6 | VI | dFr48, dFr2020 | D6 |
| HDV-7 | VII | dFr45, dFr1843 | D7A |
| | | dFr2066 | D7B |
| | | dFr644 | D7C |

Bibliographical References

Casey J. L. et al., *Proc. Natl. Acad. Sci. USA,* 1993a, 90, 9016-20.
Casey J. L. et al., *J. Infect. Dis.,* 1996b, 174, 920-6.
Chang F. L. et al., *Proc. Natl. Acad. Sci. USA,* 1991, 88, 8490-8494.
Chao Y. C. et al., *Hepatology,* 1991b, 13, 345-52.
Deny P. et al., *Res. Virol.,* 1994, 145, 287-95.
Deny P. et al., *J. Med. Virol.,* 1993, 39, 214-8.
Deny P. et al., *J. Gen. Virol.,* 1991, 72, 735-9.
Felsenstein J. et al., *Cladistics,* 1989, 5, 164-166.
Gaeta G. B. et al., *Hepatology,* 2000, 32, 824-7.

Glenn J. S. et al., *Science*, 1992, 256, 1331-3.
Hwang S. et al., *Virology*, 1993a, 193, 924-931.
Imazeki F. et al., *J. Virol.*, 1990, 64, 5594-5599.
Imazeki F. et al., *Nucl. Acid. Res.*, 1991, 19, 5439-5440.
Lai M. M. C. et al., S. Hadziyannis, J. Taylor and F. Bonino (ed.), *Hepatitis delta virus. Molecular biology, Pathogenis, and Clinical aspects*, 1993, 382, 21-27. Wiley-Liss, New York.
Lee C. M. et al., *Virology*, 1992, 188, 265-273.
Lee C. M. et al., *J. Med. Virol.*, 1996b, 49, 145-54.
Makino S. et al., *Nature*, 1987, 329, 343-6.
Nakano T. et al., *J. Gen. Virol.*, 2001, 82, 2183-2189.
Niro G. A. et al., *J. Hepatol.*, 1999, 30, 564-9.
Niro G. A. et al., *Hepatology*, 1997, 25, 728-34.
Roingeard P. et al., *Clin. Infect. Dis.*, 1992, 14, 510-14.
Saitou N. et al., *Mol. Biol. Evol.*, 1987, 4, 406-25.
Sakugawa H. et al., *J. Med. Virol.*, 1999, 58, 366-72.
Shakil A. O. et al., *Virology*, 1997, 234, 160-7.
Swofford D. et al., *PAUP\*: Phylogenetic Analysis Using Parsimony (and other methods)*, version 4.0d64.
Thompson J. D. et al., *Nuc. Acid. Res.*, 1994, 22, 4673-80.
Wang K. S. et al., *Nature*, 1986, 323, 508-514.
Wang K. S. et al., *Nature*, 1987, 328, 456.
Wu J. C. et al., *Hepatology*, 1995a, 22, 1656-60.
Wu J. C. et al., *J. Gen. Virol.*, 1998, 79, 1105-13.
Wu J. C. et al., *Lancet*, 1995b, 346, 939-41.

The invention claimed is:

1. An isolated nucleic acid molecule comprising a complete genome of an hepatitis D virus (HDV) selected from the group consisting of SEQ ID NO:1, SEQ ID NO:6, SEQ ID NO:11, SEQ ID NO:16, SEQ ID NO:21, and SEQ ID NO:26.

2. A recombinant vector comprising the isolated nucleic acid molecule of claim 1.

3. A cell transformed with the isolated nucleic acid molecule of claim 1.

4. A translation product encoded by at least one of the isolated nucleic acid molecules of claim 1.

5. A kit comprising at least one of the isolated nucleic acid molecules of claim 1 and one or more suitable reagents for detecting and genotyping HDV.

* * * * *